US012697277B2

(12) United States Patent
Pipkin et al.

(10) Patent No.: US 12,697,277 B2
(45) Date of Patent: Aug. 4, 2026

(54) MATERIALS AND METHODS FOR MITIGATING THE PRESENCE OF NITROSAMINES IN PACKAGING USING AN ACTIVE AGENT

(71) Applicant: CSP TECHNOLOGIES, INC., Auburn, AL (US)

(72) Inventors: Madison Pipkin, Auburn, AL (US); Jason Pratt, Auburn, AL (US); Matthew Riccio, Auburn, AL (US); Sharmila Kurapati, Auburn, AL (US); James S. Hollinger, Auburn, AL (US); Jonathan R. Freedman, Atlanta, GA (US); Ivy Comer, Auburn, AL (US); Amanda Murph, Auburn, AL (US); John Belfance, Auburn, AL (US); Jean Daou, Mulhouse (FR)

(73) Assignee: CSP TECHNOLOGIES, INC, Auburn, AL (US)

(*) Notice: Subject to any disclaimer, the term of this patent is extended or adjusted under 35 U.S.C. 154(b) by 0 days.

(21) Appl. No.: 19/410,618

(22) Filed: Dec. 5, 2025

(65) Prior Publication Data

US 2026/0165912 A1 Jun. 18, 2026

Related U.S. Application Data

(63) Continuation of application No. PCT/US2024/060828, filed on Dec. 18, 2024.

(51) Int. Cl.

| | |
|---|---|
| ***A61J 1/03*** | (2023.01) |
| ***A61J 1/14*** | (2023.01) |
| ***A61K 45/06*** | (2006.01) |

(52) U.S. Cl.

CPC ............. *A61J 1/035* (2013.01); *A61J 1/1431* (2015.05); *A61J 1/1468* (2015.05); *A61K 45/06* (2013.01)

(58) Field of Classification Search

CPC ........ A61J 1/035; A61J 1/1431; A61J 1/1468; A61K 45/06

See application file for complete search history.

(56) References Cited

U.S. PATENT DOCUMENTS

| | | | |
|---|---|---|---|
| 4,681,756 | A | 7/1987 | Mergens et al. |
| 8,951,549 | B2 | 2/2015 | Steimecke et al. |
| 11,285,430 | B2 | 3/2022 | Lail et al. |
| 11,833,485 | B2 | 12/2023 | Alhooshani et al. |
| 2017/0319433 | A1 | 11/2017 | Hosoi et al. |
| 2022/0079894 | A1 | 3/2022 | Saldanha et al. |
| 2023/0190762 | A1 | 6/2023 | He et al. |
| 2024/0024312 | A1 | 1/2024 | Kannan et al. |

FOREIGN PATENT DOCUMENTS

| | | | |
|---|---|---|---|
| EP | 4169516 | A1 | 4/2023 |
| WO | 2022182778 | A1 | 1/2022 |
| WO | 2022023213 | A1 | 2/2022 |
| WO | 2022034450 | A1 | 2/2022 |
| WO | 2022079287 | A1 | 4/2022 |
| WO | 2023119100 | A1 | 6/2023 |
| WO | 2024009248 | A1 | 1/2024 |
| WO | 2024263560 | A1 | 12/2024 |
| WO | 2025224654 | A1 | 10/2025 |

OTHER PUBLICATIONS

Bian, Yongning, Chuang Wang, Guocheng Zhu, Bozhi Ren, Peng Zhang, and Andrew S. Hursthouse. "Occurrence and control of N-nitrosodimethylamine in water engineering systems." Environmental Engineering Research 24(1), 1-16, published May 11, 2018.

Borths, Christopher J., Tracey Burr, Aude Figuccia, J. Gair Ford, Bing Guan, Michael T. Jones, Didier Klingeleers, Susanne Lochner, Andrew A. Rodriguez, and Christian Wetter. "Nitrosamine risk assessments in oligonucleotides." Organic Process Research & Development 27(10) (2022), 1693-1702, published Dec. 6, 2022.

Moser, Justin, Jörg Schlingemann, and Christoph Saal. "N-Nitrosamines Impurities in Pharmaceuticals The Abrupt Challenges that Resulted, the Evolving Science, and the Regulatory Framework." Journal of Pharmaceutical Sciences 112(5), 1161-1162, published May 1, 2023.

Moser, Justin, et al. "N-nitrosamine formation in pharmaceutical solid drug products: experimental observations." Journal of Pharmaceutical Sciences 2023, 112(5), 1255-1267, published May 1, 2023.

Beard, Jesicca C. et al. "An Organic Chemist's Guide to N-Nitrosamines: Their Structure, Reactivity, and Role as Contaminants" J. Org. Chem. 2021, 86(3), 2037-2057, published Jan. 21, 2021.

Mitigating N-Nitrosamine Risks with Novel Active Material Science Innovations, Abstract, Aptar CSP Technologies, Baertschi, S.; Daou, J.; Pratt, J.; May 26, 2023.

Mitigating N-Nitrosamine Risks with Novel Active Material Science Innovations, Aptar CSP Technologies, Baertschi, S.; Daou, J.; Pratt, J.; available online May 1, 2023.

(Continued)

*Primary Examiner* — Robert A Wax
*Assistant Examiner* — William Craigo
(74) *Attorney, Agent, or Firm* — Debora Plehn-Dujowich; Eckert Seamans Cherin and Mellott, LLC

(57) ABSTRACT

Disclosed herein are materials, articles of manufacture, and methods for decreasing, mitigating, removing or precluding formation of an amount of a nitrosating agent and/or an N-nitroso compound, including an N-nitrosamine, in an enclosure of a pharmaceutical drug package to inhibit a potential adverse health effect on a patient associated with the nitrosating agent or N-nitroso compound. The package contains an active agent and a pharmaceutical dosage form in an enclosure of the package. The active agent, consisting essentially of sodium bicarbonate in a granular, particulate or powdered form, is effective to decrease, mitigate, remove or preclude the formation of an amount of the nitrosating agent and/or N-nitroso compound in the enclosure and/or in the pharmaceutical dosage form. Also provided are drug delivery systems including a blister pack configured to house multiple pharmaceutical dosage forms, the blister pack including an active agent as discussed above.

30 Claims, 16 Drawing Sheets

(56) References Cited

OTHER PUBLICATIONS

Mitigating N-Nitrosamine Risks with Novel Active Material Science Innovations. White Paper, Aptar CSP Technologies, May 2023 Baertschi, S., Daou, J., & Pratt, J May 31, 2023.
International Search Report for PCT/US2024/060828, mailed Mar. 17, 2025.
Written Opinion for PCT/US2024/060828, mailed Mar. 17, 2025.
Committee for Medicinal Products for Human Use (chmp), "Procedure under Article 5(3) of Regulation EC (No) 726/2004 Nitrosamine impurities in human medicinal products", p. 1-90, Jun. 25, 2020.
International Search Report for PCT/US2024/034462, mailed Nov. 12, 2024.
Written Opinion for PCT/US2024/034462, mailed Nov. 12, 2024.

MATERIALS AND METHODS FOR MITIGATING THE PRESENCE OF NITROSAMINES IN PACKAGING USING AN ACTIVE AGENT

CROSS-REFERENCE TO RELATED APPLICATIONS

The present application is a continuation of International Application No. PCT/US2024/060828; titled "MATERIALS AND METHODS FOR MITIGATING THE PRESENCE OF NITROSAMINES IN PACKAGING USING AN ACTIVE AGENT" and filed Dec. 18, 2024, which claims priority to International Application No. PCT/US2024/034462, titled "MATERIALS AND METHODS FOR MITIGATING THE PRESENCE OF NITROSAMINES IN PACKAGING USING AN ACTIVE AGENT" and filed on Jun. 18, 2024, which claims the benefit of U.S. Provisional Application No. 63/509,158, titled "OXYGEN SCAVENGING MATERIALS FOR REDUCTION OF CONTAMINATION BY N-NITROSO COMPOUNDS IN PACKAGING" and filed on Jun. 20, 2023, U.S. Provisional Application No. 63/645,648, titled "MATERIALS AND METHODS FOR MITIGATING THE PRESENCE OF NITROSAMINES IN PACKAGING USING AN ACTIVATED AGENT" and filed on May 10, 2024 and U.S. Provisional Application No. 63/660,805, titled "MATERIALS AND METHODS FOR MITIGATING THE PRESENCE OF NITROSAMINES IN PACKAGING USING AN ACTIVE AGENT" and filed on Jun. 17, 2024. Each of the aforementioned applications is hereby incorporated by reference in its entirety.

FIELD OF THE INVENTION

The disclosed concept includes materials, articles of manufacture, and methods for scavenging N-nitroso compounds, such as N-nitrosamines, from packaging that contains a quantity of a product that is susceptible to contamination by a N-nitroso compound, to decrease the amount of, or preclude the formation of, N-nitroso compounds, such as N-nitrosamines.

BACKGROUND OF THE INVENTION

The group of compounds termed N-nitroso compounds (NOCs) bears the common >N—N=O moiety. This group can be further divided into two subgroups: (i) N-nitrosamines and (ii) N-nitrosamides and related compounds. N-Nitrosamines are N-nitroso derivatives of secondary amines; N-nitrosamides and their related compounds are those of substituted ureas, amides, carbamates, guanidines, and similar compounds.

The group is of interest due to evidence of the mutagenic and carcinogenic properties of its members. Most NOCs induce cancer in laboratory animals and may be involved in the etiology of several human cancers. The wide range of human exposure sources (exogenous and endogenous) have led to regulatory and legislative action and the development of advanced and sensitive methods of analysis.

Reaction of primary and secondary amines with nitrites or nitrous acid can lead to the production of NOCs, in which an N—H moiety is replaced with an N—N=O moiety.

Pharmaceuticals and foodstuffs containing primary and secondary amines are therefore susceptible to N-nitrosamine contamination due to the reaction, over time, with nitrites or nitrous acid. Thus, strategies to decrease or preclude formation of NOCs can decrease or minimize the health risk from consumption of these products. In turn, materials and methods for decreasing or eliminating the amount of N-nitrosamines and nitrosating agents, such as nitrites and $NO_x$, from packaging for these goods, as well as decreasing or eliminating the amount of N-nitrosamines present in the good itself, can serve to minimize the health risk due to exposure to NOC contaminants in these products.

In general, pharmaceutical compositions are expected to be safe and in compliance with requirements of governmental regulatory rules, such as the United States FDA (Food and Drug Administration) regulations. In addition, the level of impurities present in the pharmaceutical composition should comply with requirements outlined in by the U.S. FDA. The FDA has been investigating the presence of N-nitrosamine impurities in some types of medications.

The FDA has identified the following seven nitrosamine impurities that could be present in drug products: NDMA, NDEA, NMPA, NDIPA, NIPEA, NDBA, and NMBA. It is known that NDMA, NDEA, NMBA, NIPEA and NMPA have been detected in drug substances or drug products.

According to the ICH M7 Guideline, nitrosamines are classified as probable human carcinogens. Nitrosamine impurities have been found at unacceptable levels in drug products such as ARBs (-sartans), ranitidine, nizatidine and metformin, for example. NDMA was identified in certain anti-hypertensive drugs initially, followed by identification of N-nitrosamines in other categories of drugs, such as heartburn products (ranitidine, nizatidine), antidiabetic drugs (metformin), and medicines to treat and prevent tuberculosis (rifampicin, rifapentine). The "acceptable level" of N-nitrosamines is measured according to an "acceptable intake" (AI) level. A method for determining AI is set by the international standard ICH M7 Guideline. The ICH M7 recommends calculating a compound-specific AI based on rodent carcinogenicity potency data such as TD50 values, which refers to the doses giving a 50% tumor incidence in rodents. The calculated AI is then converted into a measure of parts per million (ppm). The conversion of AI to PPM varies by product and is calculated based on a drug's maximum daily dose (MDD). The conversion of AI into ppm provides a measure of an acceptable N-nitrosamine concentration in a drug that can be monitored.

The FDA has set acceptable daily intake limits for N-nitrosamines. See "Recommended Acceptable Intake Limits for Nitrosamine Drug Substance-Related Impurities", U.S. Department of Health and Human Services Food and Drug Administration, Center for Drug Evaluation and Research, Pharmacology/Toxicology, Aug. 4, 2023. The FDA has identified acceptable intake (AI) limits as follows:

| Nitrosamines | AI Limit (ng/day) |
| --- | --- |
| NDMA | 96 |
| NDEA | 26.5 |
| NMBA | 96 |
| NMPA | 26.5 |
| NIPEA | 26.5 |
| NDIPA | 26.5 |

The AI limit is a daily exposure to a compound such as those above that approximates a 1:100,000 cancer risk after 70 years of exposure. See "Control of Nitrosamine Impurities in Human Drugs/Guidance for Industry", Pharmaceutical Quality/Manufacturing Standards/Current Good Manufacturing Practice/Rev. 1, February 2021.

There are multiple reasons why N-nitrosamines can be present in drugs. It has been found that the source of N-nitrosamines can be related to the drug's manufacturing process or its chemical structure or even the conditions in which the drug is stored or packaged. N-nitrosamine impurities may increase the risk of cancer if people are exposed to them above an acceptable level and over long periods of time.

Potential root causes for nitrosamine impurities in drugs can include (i) the presence of secondary, tertiary, or quaternary amines and nitrite salts under acidic reaction conditions, (ii) use of sodium nitrite or other nitrosating agents, (iii) contaminants present in raw materials during API manufacturing, (iv) recovered solvents, catalysts, and reagents, (v) cross-contamination, (vi) use of quenching processes, (vii) lack of process optimization and control, and (viii) degradation processes/stability in starting materials, intermediates and drug substances or storage thereof.

It is necessary to decrease the amount of N-nitrosamines in pharmaceutical and medicament compositions and their packaging to meet safety standards, and reduce the risk of N-nitrosamine exposure to patients taking the drugs. Thus, there remains a need for materials, articles of manufacture, and methods that can scavenge nitrosamines and nitrosating agents, such as nitrites and $NO_x$, from packaging and/or the goods enclosed therein, wherein the goods comprise a quantity of a product, e.g., pharmaceutical or foodstuff, that is susceptible to contamination by N-nitroso compounds, to decrease the amount of N-nitroso compounds in the goods and/or the packaging, or preclude the formation of N-nitroso compounds in the goods and/or the packaging. There is also a need for a solution that does not require reformulating a pharmaceutical composition (e.g., by putting a mitigant in the composition itself) or changing the process by which the pharmaceutical composition is manufactured. The desired materials, articles of manufacture and methods would decrease the levels of, or formation of, free N-nitroso compounds in products (e.g., pharmaceutical compositions) and/or their packaging, thereby reducing the hazards associated with these compounds on a patient.

SUMMARY OF THE INVENTION

Optionally provided herein is a method of decreasing, mitigating, removing or precluding formation of an amount of nitrosating agent and/or an N-nitroso compound in an enclosure of a pharmaceutical drug package to inhibit a potential adverse health effect on a patient associated with the nitrosating agent or N-nitroso compound, the method comprising: a.) providing at least one pharmaceutical dosage form in the enclosure of the pharmaceutical drug package, thereby forming a headspace in the enclosure in a portion of the enclosure not occupied by the at least one pharmaceutical dosage form, the at least one pharmaceutical dosage form having in it, on it, or having a propensity to form, emit, or react with the nitrosating agent and/or N-nitroso compound that is associated with the potential adverse health effect on the patient; and b.) providing an entrained polymer component within the headspace, the entrained polymer component comprising a blended form of a base polymer and an ascorbic acid active agent; wherein the entrained polymer component is effective to decrease, mitigate, remove or preclude the formation of the amount of nitrosating agent and/or N-nitroso compound in the headspace and/or in the at least one pharmaceutical dosage form, thereby inhibiting the potential adverse health effect on the patient associated with the nitrosating agent or N-nitroso compound.

Also optionally provided herein is a method of decreasing, mitigating, removing or precluding formation of an amount of nitrosating agent and/or an N-nitroso compound in an enclosure of a pharmaceutical drug package to inhibit a potential adverse health effect on a patient associated with the nitrosating agent or N-nitroso compound, the method comprising: a.) providing at least one pharmaceutical dosage form in the enclosure of the pharmaceutical drug package, thereby forming a headspace in the enclosure in a portion of the enclosure not occupied by the at least one pharmaceutical dosage form, the at least one pharmaceutical dosage form having in it, on it, or having a propensity to form, emit, or react with the nitrosating agent and/or N-nitroso compound that is associated with the potential adverse health effect on the patient; and b.) providing an entrained polymer component within the headspace, the entrained polymer component comprising a blended form of a base polymer and a sodium chloride active agent, optionally wherein the entrained polymer component is free from or substantially free from a metallic material, optionally wherein the metallic material is iron; wherein the entrained polymer component is effective to decrease, mitigate, remove or preclude the formation of the amount of nitrosating agent and/or N-nitroso compound in the headspace and/or in the at least one pharmaceutical dosage form, thereby inhibiting the potential adverse health effect on the patient associated with the nitrosating agent or N-nitroso compound.

Also optionally provided herein is a method of decreasing, mitigating, removing or precluding formation of an amount of nitrosating agent and/or an N-nitroso compound in an enclosure of a pharmaceutical drug package to inhibit a potential adverse health effect on a patient associated with the nitrosating agent or N-nitroso compound, the method comprising: a.) providing at least one pharmaceutical dosage form in the enclosure of the pharmaceutical drug package, thereby forming a headspace in the enclosure in a portion of the enclosure not occupied by the at least one pharmaceutical dosage form, the at least one pharmaceutical dosage form having in it, on it, or having a propensity to form, emit, or react with the nitrosating agent and/or N-nitroso compound that is associated with the potential adverse health effect on the patient; and b.) providing an entrained polymer component within the headspace, the entrained polymer component comprising a blended form of a base polymer and a sodium bicarbonate active agent; wherein the entrained polymer component is effective to decrease, mitigate, remove or preclude the formation of the amount of nitrosating agent and/or N-nitroso compound in the headspace and/or in the at least one pharmaceutical dosage form, thereby inhibiting the potential adverse health effect on the patient associated with the nitrosating agent or N-nitroso compound.

Also optionally provided herein is a method of decreasing, mitigating, removing or precluding formation of an amount of nitrosating agent and/or an N-nitroso compound in an enclosure of a pharmaceutical drug package to inhibit a potential adverse health effect on a patient associated with the nitrosating agent or N-nitroso compound, the method comprising: a.) providing at least one pharmaceutical dosage form in the enclosure of the pharmaceutical drug package, thereby forming a headspace in the enclosure in a portion of the enclosure not occupied by the at least one pharmaceutical dosage form, the at least one pharmaceutical dosage form having in it, on it, or having a propensity to form, emit, or react with the nitrosating agent and/or N-nitroso compound that is associated with the potential adverse health effect on the patient; and b.) providing an entrained polymer component within the headspace, the entrained polymer component comprising a blended form of a base polymer and a vitamin E active agent; wherein the entrained polymer component is effective to decrease, mitigate, remove or preclude the formation of the amount of nitrosating agent and/or N-nitroso compound in the headspace and/or in the at least one pharmaceutical dosage form, thereby inhibiting the potential adverse health effect on the patient associated with the nitrosating agent or N-nitroso compound.

Also optionally provided herein is a method of decreasing, mitigating, removing or precluding formation of an amount of nitrosating agent and/or an N-nitroso compound in an enclosure of a pharmaceutical drug package to inhibit a potential adverse health effect on a patient associated with the nitrosating agent or N-nitroso compound, the method comprising: a.) providing at least one pharmaceutical dosage form in the enclosure of the pharmaceutical drug package, thereby forming a headspace in the enclosure in a portion of the enclosure not occupied by the at least one pharmaceutical dosage form, the at least one pharmaceutical dosage form having in it, on it, or having a propensity to form, emit, or react with the nitrosating agent and/or N-nitroso compound that is associated with the potential adverse health effect on the patient; and b.) providing an entrained polymer component within the headspace, the entrained polymer component comprising a blended form of a base polymer and a calcium carbonate active agent; wherein the entrained polymer component is effective to decrease, mitigate, remove or preclude the formation of the amount of nitrosating agent and/or N-nitroso compound in the headspace and/or in the at least one pharmaceutical dosage form, thereby inhibiting the potential adverse health effect on the patient associated with the nitrosating agent or N-nitroso compound.

Also provided herein is a method of decreasing, mitigating, removing or precluding formation of an amount of nitrosating agent and/or an N-nitroso compound in an enclosure of a pharmaceutical drug package to inhibit a potential adverse health effect on a patient associated with the nitrosating agent or N-nitroso compound, the method comprising: a.) providing at least one pharmaceutical dosage form in the enclosure of the pharmaceutical drug package, thereby forming a headspace in the enclosure in a portion of the enclosure not occupied by the at least one pharmaceutical dosage form, the at least one pharmaceutical dosage form having in it, on it, or having a propensity to form, emit, or react with the nitrosating agent and/or N-nitroso compound that is associated with the potential adverse health effect on the patient; and b.) providing an entrained polymer component within the headspace, the entrained polymer component comprising a blended form of a base polymer and a magnesium carbonate active agent; wherein the entrained polymer component is effective to decrease, mitigate, remove or preclude the formation of the amount of nitrosating agent and/or N-nitroso compound in the headspace and/or in the at least one pharmaceutical dosage form, thereby inhibiting the potential adverse health effect on the patient associated with the nitrosating agent or N-nitroso compound.

Also provided herein is a method of decreasing, mitigating, removing or precluding formation of an amount of nitrosating agent and/or an N-nitroso compound in an enclosure of a pharmaceutical drug package to inhibit a potential adverse health effect on a patient associated with the nitrosating agent or N-nitroso compound, the method comprising: a.) providing at least one pharmaceutical dosage form in the enclosure of the pharmaceutical drug package, thereby forming a headspace in the enclosure in a portion of the enclosure not occupied by the at least one pharmaceutical dosage form, the at least one pharmaceutical dosage form having in it, on it, or having a propensity to form, emit, or react with the nitrosating agent and/or N-nitroso compound that is associated with the potential adverse health effect on the patient; and b.) providing an entrained polymer component within the headspace, the entrained polymer component comprising a blended form of a base polymer and a silica gel active agent; wherein the entrained polymer component is effective to decrease, mitigate, remove or preclude the formation of the amount of nitrosating agent and/or N-nitroso compound in the headspace and/or in the at least one pharmaceutical dosage form, thereby inhibiting the potential adverse health effect on the patient associated with the nitrosating agent or N-nitroso compound.

Also provided herein is a method of decreasing, mitigating, removing or precluding formation of an amount of nitrosating agent and/or an N-nitroso compound in an enclosure of a pharmaceutical drug package to inhibit a potential adverse health effect on a patient associated with the nitrosating agent or N-nitroso compound, the method comprising: a.) providing at least one pharmaceutical dosage form in the enclosure of the pharmaceutical drug package, thereby forming a headspace in the enclosure in a portion of the enclosure not occupied by the at least one pharmaceutical dosage form, the at least one pharmaceutical dosage form having in it, on it, or having a propensity to form, emit, or react with the nitrosating agent and/or N-nitroso compound that is associated with the potential adverse health effect on the patient; and b.) providing an entrained polymer component within the headspace, the entrained polymer component comprising a blended form of a base polymer and a polymer-based oxygen scavenging active agent; wherein the entrained polymer component is effective to decrease, mitigate, remove or preclude the formation of the amount of nitrosating agent and/or N-nitroso compound in the headspace and/or in the at least one pharmaceutical dosage form, thereby inhibiting the potential adverse health effect on the patient associated with the nitrosating agent or N-nitroso compound.

BRIEF DESCRIPTION OF THE DRAWINGS

The foregoing summary, as well as the following detailed description of the presently disclosed technology, will be better understood when read in conjunction with the appended drawings, wherein like numerals designate like elements throughout. For the purpose of illustrating the presently disclosed technology, there are shown in the drawings various illustrative embodiments. It should be understood, however, that the presently disclosed technology is not limited to the precise arrangements and instrumentalities shown. In the drawings.

DETAILED DESCRIPTION OF PREFERRED EMBODIMENTS

Figure 1:
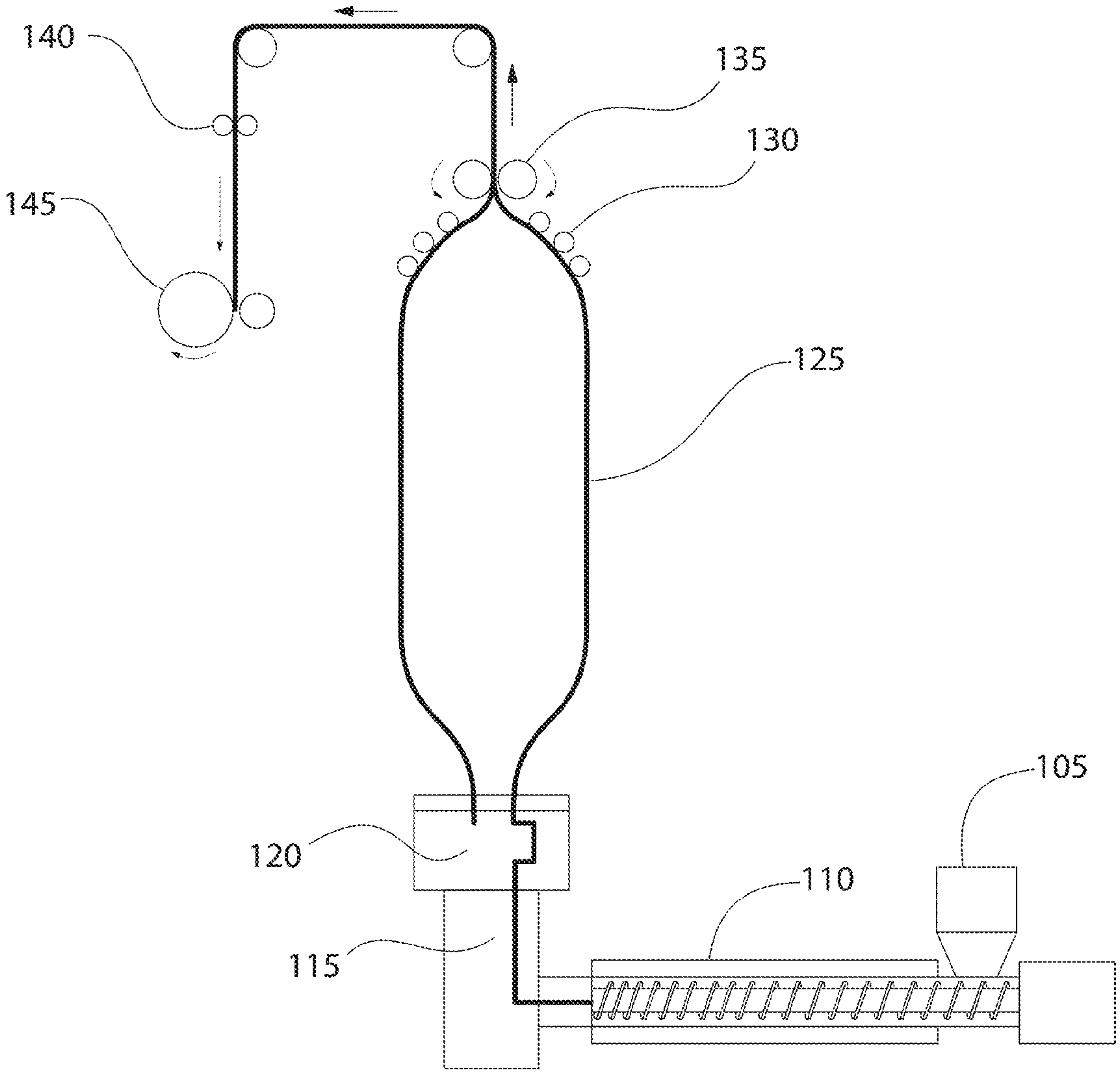
FIG. 1 is a schematic illustration of a representative apparatus and process for forming blown film according to an optional embodiment of the disclosed concept.

While systems, devices and methods are described herein by way of examples and embodiments, those skilled in the art recognize that the systems, devices and methods of the presently disclosed technology are not limited to the embodiments or drawings described. Rather, the presently disclosed technology covers all modifications, equivalents and alternatives falling within the spirit and scope of the appended claims. Any headings used herein are for organizational purposes only and are not meant to limit the scope of the description or the claims.

Accordingly, provided herein is a container comprising an active agent that is capable of decreasing, mitigating, removing or precluding a nitrosating agent and/or an N-nitroso compound from a headspace within the container and/or from the goods enclosed in the container. Also provided herein is a method for using an active agent for scavenging a nitrosating agent and/or an N-nitroso compound in order to decrease or mitigate the formation of, or remove a nitrosating agent and/or an N-nitroso compound from the container and/or the goods enclosed therein. Optionally, the scavenging material decreases the amount of an N-nitroso compound. Optionally, the scavenging material decreases the amount of a nitrosating agent, such as nitrite or $NO_x$. Optionally, the scavenging material is an oxygen scavenging material.

Optionally, the disclosed concept includes a system for reducing the presence of a nitrosating agent and/or an N-nitroso compound from a drug product, and mitigating a potential adverse effect on a patient that uses the drug product. The system comprises a package that includes an enclosure and one or more pharmaceutical dosage forms having in it, on it, or having a propensity to form or emit, a nitrosating agent and/or an N-nitroso compound. A headspace is formed within a volume of the enclosure that is not occupied by the one or more pharmaceutical dosage forms. Disposed within the headspace is an effective amount of an active agent to mitigate formation of and/or decrease the presence of the nitrosating agent and/or N-nitroso compound in or on the one or more pharmaceutical dosage forms and/or in the headspace. Optionally, the package can include a blister pack, a vial or a bottle.

Optionally, the disclosed concept includes a method of decreasing, mitigating, removing or precluding formation of and/or the amount of a nitrosating agent and/or an N-nitroso compound in an enclosure of a pharmaceutical drug package to inhibit a potential adverse health effect on a patient associated with the nitrosating agent or N-nitroso compound. The method includes providing at least one pharmaceutical dosage form in the enclosure of the pharmaceutical drug package, thereby forming a headspace in the enclosure in a portion of the enclosure not occupied by the pharmaceutical dosage form having in it, on it, or having a propensity to form, emit, or react with the nitrosating agent and/or N-nitroso compound that is associated with the potential adverse health effect on the patient, and providing an entrained polymer component within the headspace, the entrained polymer component comprising a blended form of a base polymer and an active agent. The active agent being at least one member selected from the group consisting of sodium chloride, ascorbic acid, sodium bicarbonate, vitamin E, calcium carbonate, magnesium carbonate, silica gel, and polymer-based oxygen scavenger. Optionally, when the active agent is sodium chloride, the entrained polymer component is free from or substantially free from a metallic material, optionally wherein the metallic material is iron. Optionally, one or both of the headspace and the pharmaceutical dosage form includes a nitrosating agent and/or an N-nitroso compound. The entrained polymer component is effective to decrease, mitigate, remove or preclude the formation and/or the amount of the nitrosating agent and/or N-nitroso compound in the headspace and/or in the pharmaceutical dosage form, thereby inhibiting the potential adverse health effect on the patient associated with the nitrosating agent or N-nitroso compound.

Optionally, the entrained polymer component or active agent is effective to decrease, mitigate, remove or preclude the formation of an amount of the N-nitroso compound in the headspace to less than 1500 ppm, optionally less than 400 ppm, optionally less than 100 ppm, optionally less than 95 ppm, optionally less than 90 ppm, optionally less than 85 ppm, optionally less than 80 ppm, optionally less than 75 ppm, optionally less than 70 ppm, optionally less than 65 ppm, optionally less than 60 ppm, optionally less than 55 ppm, optionally less than 50 ppm, optionally less than 45 ppm, optionally less than 40 ppm, optionally less than 35 ppm, optionally less than 25 ppm, optionally less than 20 ppm, optionally less than 15 ppm, optionally less than 14 ppm, optionally less than 13 ppm, optionally less than 12 ppm, optionally less than 11 ppm, optionally less than 10 ppm, optionally less than 9 ppm, optionally less than 8 ppm, optionally less than 7 ppm, optionally less than 6 ppm, optionally less than 5 ppm, optionally less than 4 ppm, optionally less than 3 ppm, optionally less than 2 ppm, optionally less than 1 ppm, optionally less than 0.9 ppm, optionally less than 0.8 ppm, optionally less than 0.7 ppm, optionally less than 0.6 ppm, optionally less than 0.5 ppm, optionally less than 0.4 ppm, optionally less than 0.3 ppm, optionally less than 0.2 ppm, or optionally less than 0.1 ppm.

Optionally, the entrained polymer component or active agent is effective to decrease, mitigate, remove or preclude the formation of an amount of the N-nitroso compound in the pharmaceutical dosage form to less than 1500 ppm, optionally less than 400 ppm, optionally less than 100 ppm, optionally less than 95 ppm, optionally less than 90 ppm, optionally less than 85 ppm, optionally less than 80 ppm, optionally less than 75 ppm, optionally less than 70 ppm, optionally less than 65 ppm, optionally less than 60 ppm, optionally less than 55 ppm, optionally less than 50 ppm, optionally less than 45 ppm, optionally less than 40 ppm, optionally less than 35 ppm, optionally less than 25 ppm, optionally less than 20 ppm, optionally less than 15 ppm, optionally less than 14 ppm, optionally less than 13 ppm, optionally less than 12 ppm, optionally less than 11 ppm, optionally less than 10 ppm, optionally less than 9 ppm, optionally less than 8 ppm, optionally less than 7 ppm, optionally less than 6 ppm, optionally less than 5 ppm, optionally less than 4 ppm, optionally less than 3 ppm, optionally less than 2 ppm, optionally less than 1 ppm, optionally less than 0.9 ppm, optionally less than 0.8 ppm, optionally less than 0.7 ppm, optionally less than 0.6 ppm, optionally less than 0.5 ppm, optionally less than 0.4 ppm, optionally less than 0.3 ppm, optionally less than 0.2 ppm, or optionally less than 0.1 ppm.

Optionally, the entrained polymer component or active agent is effective to decrease, mitigate, remove or preclude the formation of an amount of the nitrosating agent in the headspace to less than 1500 ppm, optionally less than 400 ppm, optionally less than 100 ppm, optionally less than 95 ppm, optionally less than 90 ppm, optionally less than 85 ppm, optionally less than 80 ppm, optionally less than 75 ppm, optionally less than 70 ppm, optionally less than 65 ppm, optionally less than 60 ppm, optionally less than 55 ppm, optionally less than 50 ppm, optionally less than 45 ppm, optionally less than 40 ppm, optionally less than 35 ppm, optionally less than 25 ppm, optionally less than 20 ppm, optionally less than 15 ppm, optionally less than 14 ppm, optionally less than 13 ppm, optionally less than 12 ppm, optionally less than 11 ppm, optionally less than 10 ppm, optionally less than 9 ppm, optionally less than 8 ppm, optionally less than 7 ppm, optionally less than 6 ppm, optionally less than 5 ppm, optionally less than 4 ppm, optionally less than 3 ppm, optionally less than 2 ppm, optionally less than 1 ppm, optionally less than 0.9 ppm, optionally less than 0.8 ppm, optionally less than 0.7 ppm, optionally less than 0.6 ppm, optionally less than 0.5 ppm, optionally less than 0.4 ppm, optionally less than 0.3 ppm, optionally less than 0.2 ppm, or optionally less than 0.1 ppm.

Optionally, the entrained polymer component or active agent is effective to decrease, mitigate, remove or preclude the formation of an amount of the nitrosating agent in the pharmaceutical dosage form to less than 1500 ppm, optionally less than 400 ppm, optionally less than 100 ppm, optionally less than 95 ppm, optionally less than 90 ppm, optionally less than 85 ppm, optionally less than 80 ppm, optionally less than 75 ppm, optionally less than 70 ppm, optionally less than 65 ppm, optionally less than 60 ppm, optionally less than 55 ppm, optionally less than 50 ppm, optionally less than 45 ppm, optionally less than 40 ppm, optionally less than 35 ppm, optionally less than 25 ppm, optionally less than 20 ppm, optionally less than 15 ppm, optionally less than 14 ppm, optionally less than 13 ppm, optionally less than 12 ppm, optionally less than 11 ppm, optionally less than 10 ppm, optionally less than 9 ppm, optionally less than 8 ppm, optionally less than 7 ppm, optionally less than 6 ppm, optionally less than 5 ppm, optionally less than 4 ppm, optionally less than 3 ppm, optionally less than 2 ppm, optionally less than 1 ppm, optionally less than 0.9 ppm, optionally less than 0.8 ppm, optionally less than 0.7 ppm, optionally less than 0.6 ppm, optionally less than 0.5 ppm, optionally less than 0.4 ppm, optionally less than 0.3 ppm, optionally less than 0.2 ppm, or optionally less than 0.1 ppm.

Optionally, the entrained polymer component or active agent or scavenging material comprises a base. Optionally, the base is an organic amine. Optionally, the organic amine comprises at least one hydroxyl group. Optionally, the organic amine contains at most 8 carbons, optionally at most 6 carbons, optionally at most 4 carbons. Optionally, the organic amine contains at most 3 nitrogens, optionally at most 2 nitrogens, optionally 1 nitrogen. Optionally, the organic amine contains 3 oxygens or fewer, optionally 2 oxygens or fewer, optionally at most 1 oxygen. Optionally, all of the nitrogens in the organic amine are amino nitrogens. Optionally, all of the oxygens in the organic amine are hydroxyl oxygens. Optionally, the pKa for the conjugate acid of the organic amine is between 6 and 11, optionally between 6 and 10, optionally between 6.5 and 10, optionally between 6.5 and 9.5, optionally between 6.5 and 9, optionally between 6.5 and 8.5. Optionally, the organic amine is chosen from ethanolamine, diethanolamine, triethanolamine, and tris(hydroxymethyl)aminomethane. Optionally, the organic base is a monoacidic base. Optionally, the entrained polymer component or active agent or scavenging material further comprises the conjugate acid of the monoacidic base. Optionally, the monoacidic base and the conjugate acid of the monoacidic base are provided in a ratio between 30:70 and 70:30, optionally between 35:65 and 65:35, optionally between 40:60 and 60:40, optionally between 45:55 and 55:45.

Also provided herein is a method for the manufacture of a container comprising an entrained polymer component or active agent or scavenging material that is capable of removing an N-nitroso compound and/or a nitrosating agent, such as nitrite or $NO_x$, from a headspace within the container.

The disclosed concept also includes a drug delivery system that includes a blister pack configured to house one or more pharmaceutical dosage forms. The blister pack includes a backing and a cover attached to the backing. In combination, the cover and backing form at least one enclosure configured to contain a single pharmaceutical dosage form. The single pharmaceutical dosage form is housed within at least one enclosure, and a headspace is formed within a volume of the at least one enclosure that is not occupied by the single pharmaceutical dosage form. Additionally, an entrained polymer component comprising a blended form of a base polymer and an active agent effective for decreasing, mitigating, removing or precluding the formation and/or amount of a nitrosating agent and/or an N-nitroso compound in the headspace and/or in the pharmaceutical dosage form, the active agent being at least one member selected from the group consisting of sodium chloride, ascorbic acid, sodium bicarbonate, vitamin E, calcium carbonate, magnesium carbonate, silica gel, and polymer-based oxygen scavenger. Optionally, when the active agent is sodium chloride, the entrained polymer component is free from or substantially free from a metallic material, optionally wherein the metallic material is iron.

The disclosed concept also includes a drug delivery system that includes a bottle configured to house pharmaceutical dosage forms in a solid (e.g., capsules or tablets) or liquid format. An active agent in a drop-in configuration, such as a film, sachet, puck or cannister, can be positioned inside the bottle. Optionally, the active agent film can form a liner/lining inside the bottle. Optionally, the bottle itself can be at least partially composed of a material that includes the active agent. Optionally, the active agent is effective for reducing, mitigating, removing or precluding the formation and/or concentration level of an N-nitroso compound and/or nitrosating agent, such as nitrite and $NO_x$, in a headspace formed within a volume of the bottle that is not occupied by the pharmaceutical dosage form.

Optionally, the product susceptible to contamination by an N-nitroso compound and/or a nitrosating agent is a foodstuff Optionally, the product susceptible to contamination by an N-nitroso compound and/or a nitrosating agent is a medicament, such as a pharmaceutical dosage form.

Optionally, the period of product storage is no less than 1 week, optionally no less than 2 weeks, optionally no less than 3 weeks, optionally no less than 6 weeks, optionally no less than 13 weeks, optionally no less than 26 weeks, optionally no less than 1 year, optionally from 26 weeks to 3 years, optionally from 1 year to 3 years, optionally from 1 year to 2 years, optionally from 2 years to 3 years, optionally about 2 years.

Optionally, the period of product storage is no more than 1 year, optionally no more than 26 weeks, optionally no more than 13 weeks, optionally no more than 6 weeks, optionally no more than 3 weeks, optionally no more than 2 weeks, optionally no more than 1 week, optionally from 1 week to 1 year, optionally from 13 weeks to 1 year.

Optionally, the product itself contains an N-nitroso compound and/or a nitrosating agent, such as nitrite and $NO_x$, prior to packaging, i.e., formed during product synthesis or formulation prior to placement or storage in a container or package. Optionally, the product emits a nitrosating agent, such as nitrite and $NO_x$, in the package, i.e., when stored in the container or package, that reacts with a primary or secondary amine to form an N-nitroso compound in the product and/or in the headspace of the container or package in the absence of any preventative measures.

Optionally, the initial rate for uptake of the N-nitroso compound and/or nitrosating agent by the scavenging material is less than the rate of formation of the N-nitroso compound and/or nitrosating agent in the container or package. Optionally, the initial rate for uptake of the N-nitroso compound and/or nitrosating agent by the scavenging material is greater than the rate of formation of the N-nitroso compound and/or nitrosating agent in the container or package. Optionally, essentially no N-nitroso compound and/or nitrosating agent is formed during the period of product storage.

The disclosed concept also includes a method for treating a patient having a medical condition with a pharmaceutical dosage form that includes or forms an N-nitroso compound and/or a nitrosating agent. The method is configured to mitigate a potential adverse effect on a patient associated with an N-nitroso compound and/or a nitrosating agent. The method includes providing a package comprising an enclosure and one or more pharmaceutical dosage forms housed within the enclosure, with a headspace being formed within a volume of the enclosure that is not occupied by the one or more pharmaceutical dosage forms. The method further includes providing an amount of an active agent, e.g., a scavenging material, in the headspace, that is effective in scavenging a nitrosamine and nitrosating agent or in decreasing or mitigating formation of a an N-nitroso compound and/or a nitrosating agent in a headspace and/or in the pharmaceutical dosage form within the container. The amount of active agent is separate and apart from the one or more pharmaceutical dosage forms. The active agent being at least one member selected from the group consisting of sodium chloride, ascorbic acid, sodium bicarbonate, vitamin E, calcium carbonate, magnesium carbonate, silica gel, and polymer-based oxygen scavenger. Optionally, when the active agent is sodium chloride, the entrained polymer component is free from or substantially free from a metallic material, optionally wherein the metallic material is iron. Optionally, an entrained polymer component comprises a blended form of a base polymer and the active agent. The one or more pharmaceutical dosage forms is removed from the enclosure for administering a therapeutically effective amount of drug to the patient for treating the medical condition with improved patient safety by reducing the potential adverse effect associated with the pharmaceutical dosage form through decreasing the N-nitroso compound and/or nitrosating agent by the amount of the active agent or entrained polymer component.

Optionally, the entrained polymer component or active agent is effective to decrease, mitigate, remove or preclude the formation of an amount of N-nitroso compound, such that the N-nitroso compound ingested by the patient, as a result of ingesting the pharmaceutical dosage form, does not exceed the daily acceptable intake limit established by the United States Food and Drug Administration. Optionally, the entrained polymer component or active agent is effective such that the amount of N-nitroso compound ingested by the patient does not exceed 96 ng/day for NDMA or NMBA, or 26.5 ng/day for NDEA, NMPA, NIPEA or NDIPA.

Optionally, the N-nitroso compound has a formula weight of 300 g/mol or less, optionally 200 g/mol or less, optionally 160 g/mol or less, optionally 120 g/mol or less.

Optionally, the N-nitroso compound has a vapor pressure at 20° C. of 0.2 Torr or higher, optionally 0.5 Torr or higher, optionally 1 Torr or higher, optionally 2 Torr or higher, optionally 3 torr or higher, optionally 4 torr or higher, or optionally 5 Torr or higher.

Optionally, the N-nitroso compound has a boiling point at atmospheric pressure of 250° C. or lower, optionally 225° C. or lower, optionally 200° C. or lower, optionally 190° C. or lower, optionally 180° C. or lower, optionally 170° C. or lower, or optionally 160° C. or lower.

Optionally, the N-nitroso compound is the N-nitroso derivative of a aliphatic secondary amine. Optionally, the aliphatic secondary amine is a cyclic amine. Optionally, the aliphatic secondary amine is an acyclic amine.

Optionally, the aliphatic secondary amine is composed of elements chosen from C, H, N, and O.

Optionally, the aliphatic secondary amine is composed of elements chosen from C, H and N.

Optionally, the aliphatic secondary amine has 10 carbons or fewer, optionally 8 carbons or fewer, optionally 6 carbons or fewer, optionally 4 carbons or fewer. Optionally, the aliphatic secondary amine has 1, 2, or 3 nitrogens, optionally 1 or 2 nitrogens, optionally 1 nitrogen. Optionally, the aliphatic secondary amine has zero, 1, or 2 oxygens, optionally zero or 1 oxygens, optionally zero oxygens.

Optionally, the N-nitroso compound has the formula $R^1R^2N—N{=}O$, wherein $R^1$ and $R^2$ are independently chosen from $C_{1-6}$alkyl, $C_{3-7}$cycloalkyl, and 4- to 7-membered heterocycloalkyl.

Optionally, the N-nitroso compound has the formula $R^1R^2N—N{=}O$, wherein $R^1$ and $R^2$ combine to form a 4- to 7-membered heterocycloalkyl optionally substituted with an $R^3$ chosen from $C_{1-6}$alkyl and $C_{3-7}$cycloalkyl. Optionally, the 4- to 7-membered heterocycloalkyl is chosen from pyrrolidine, piperidine, and piperazine.

Optionally, the N-nitroso compound is chosen from N-nitrosodimethylamine (NDMA), N-nitrosodiethylamine (NDEA), N-nitrosodi-1-propylamine (NDPA), N-nitrosodi-2-propylamine (NDIPA), N-nitrosodi-1-butylamine (NDBA), N-nitroso-N-ethyl-2-propylamine (NEIPA), N-nitroso-N-methylpiperazine (NMP), N-nitroso-N-cyclopentylpiperazine (CPNP), and N-nitrosopyrrolidine (NPYR). Optionally, the N-nitroso compound is N-nitrosodimethylamine. Optionally, the N-nitroso compound is neither of 1-methyl-4-nitrosopiperazine, 1-cyclopentyl-4-nitrosopiperazine, or N-nitroso-3-azabicyclo[3.3.0]octane.

Optionally, the pharmaceutical dosage form of the methods, materials and systems disclosed herein may include one or more of the following or a pharmaceutically acceptable salt thereof: Almotriptan, Metformin, Ranitidine, Amitriptyline, Nortriptyline, Betahistine, Chloropyramine, Citalopram, Sumatriptan, Lamisil, Terbisil, Zostavax, Bedaquiline, Brompheniramine, Cabergoline, Carbinoxamine, Chlophedianol, Chlorpheniramine, Chlorpromazine, Clarithromycin, Clomipramine, Clozapine, Cyclobenzaprine, Demeclocycline, Dexbrompheniramine, Dexchlorpheniramine, Diltiazem, Diphenhydramine, Doxepin, Doxycycline, Doxylamine, Eravacycline, Erythromycin, Escitalopram, Imipramine, Maralixibat, Masitinib, Methadone, Methylene Blue, Mifepristone, Minocycline, Olopatadine, Omadacycline, Padimate O, Pheniramine, Phenyltoloxamine, Promethazine, Propoxyphene, Pyrilamine, Quinupristin, Rivastigmine, Rizatriptan, Sarecycline, Sildenafil, Spinosad, Tamoxifen, Tapentadol, Telithromycin, Tetracycline, Thonzylamine, Tigecycline, Tramadol, Trimethobenzamide, Trimipramine, Ulipristal Acetate, Venlafaxine, Zolmitriptan, Tripelennamine, Desvenlafaxine, Orphenadrine, Terbinafine, Ethylisopropylamine, Sitagliptin, Losartan, Valsartan, Atomoxetine, Lidocaine, Azelastine, Duloxetine, Fluoxetine, Chloropyramine, Phenylephrine, Rasagiline, Reboxetine, Aripiprazole, Mitapivat, Rifampicin, Alogliptin, Ranolazine, Rotigotine, Azacyclonol, Quetiapine, Cinacalcet, Desloratadine, Nintedanib, Sildenafil, Landiolol, Mirabegron, Mirtazapine, Valaciclovir, Pramipexole, Ranolazine, Ribociclib, Tetracaine, Trimetazidine, Varenicline, Vortioxetine, Methylphenidate, Paroxetine, Piperidine, Moxifloxacin, Daridorexant, Rotigotine, Ropivacaine, Ambroxol, Atenolol, Benazepril, Betaxolol, Bisoprolol, Bumetanide, Bupropion, Celiprolol, Cilazapril, Ciprofloxacin, Dabigatran Etexilate, Trimebutine, Diclofenac, Dorzolamide, Enalapril, Esmolol, Isosorbide mononitrate, Imatinib, Isosorbide mononitrate, Indapamide, Ketamine, Labetalol, Leniolisib, Levofloxacin, Lisinopril, Metoprolol, Moxifloxacin, Nebivolol, Perindopril, Arpraziquantel, Propranolol, Pseudoephedrine, Quetiapine, Ramipril, Rivaroxaban, Salbutamol, Sertraline, Sotalol, Tamsulosin, Ticagrelor, Urapidil, Vildagliptin, Gliclazide, Mefenamic acid, Azithromycin, Calcium folinate, Calcium levofolinate, Hydrochlorothiazide, Quinapril and Ritonavir.

Optionally, the active agents that are effective to decrease, mitigate, remove or preclude N-nitroso compounds and/or nitrosating agents resulting from a pharmaceutical dosage form itself or the storage of a pharmaceutical dosage form in a container, are selected from: ascorbic acid, Vitamin E, sodium chloride, sodium hydroxide, almond flour, potassium hydroxide, ferulic acid, walnut powder, sodium bicarbonate, flaxseed powder, date seed powder, aloe vera powder, calcium carbonate, sodium carbonate, turmeric powder, ground cinnamon, anthocyanin (blueberry powder), coffee, astacanthin, evergreen (peppermint leaves), magnesium carbonate, caffeic acid, dried peppermint, spirulina, sodium alginate, zeaxanthin, beta cyclodextrin powder, acai powder, lycopene, L-ascorbic acid, 3 A or 4 A molecular sieve, calcium sulfate, green tea extract, grape seed powder, polyphenol (pomegranate powder), 13Y zeolite, activated carbon, tris-activated carbon, hydrochloric acid, ferric oxide, crushed red pepper, pumpkin seed powder, Vitamin A, barley flour, ground clove, propyl gallate, beta carotene, silica gel, garlic extract, coenzyme Q10, beet root powder, magnesium chloride, olive leaf extract, and polymer-based oxygen scavenger.

Optionally, the active agents that are found to be effective to decrease, mitigate, remove or preclude N-nitroso compounds and/or nitrosating agents resulting from certain pharmaceutical dosage forms may be extended to predict their effectiveness in other pharmaceutical dosage forms. It will be appreciated that a decrease, mitigation, removal or preclusion of N-nitroso compounds and/or nitrosating agents by active agents for a particular pharmaceutical dose form suggests similar reactivity can be expected for similar pharmaceutical dosage forms. Optionally, pharmaceutical dosage forms that have a similar chemical structure or similar components/characteristics in their chemical structures may be reasonably expected to interact or react with active agents in a similar manner to decrease, mitigate, remove or preclude an N-nitroso compound and/or a nitrosating agent. Optionally, pharmaceutical dosage forms having in common a certain functional group in their chemical structures that reacts to form an N-nitroso compound and/or a nitrosating agent can be reasonably expected to similarly interact or react with a certain active agent to decrease, mitigate, remove or preclude the amount of an N-nitroso compound and/or a nitrosating agent.

It is generally recognized in the art that secondary amines (i.e., $R^1R^2NH$, for which neither of $R^1$ and $R^2$ is H) react differently with nitrosating agents (i.e., $NO^+$ or synthetic equivalents) as compared to tertiary amines (i.e., $R^1R^2R^3N$, for which none of $R^1$, $R^2$, and $R^3$ is H). As shown in Scheme I, secondary amines, in a first step, react with $NO^+$ or equivalent to form a positively charged ammonium species, which can rapidly lose $H^+$ to form the stable, uncharged nitrosamine.

Scheme I.

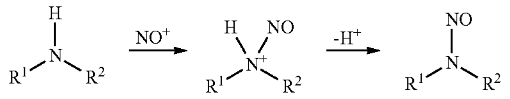

As shown in Scheme II, tertiary amines undergo the first step of Scheme I, i.e. reaction with $NO^+$ or equivalent to form the positively charged ammonium species. However, loss of $H^+$ is not an option for this species, and the second step of the mechanism of Scheme I is therefore not available for Scheme II.

Scheme II.

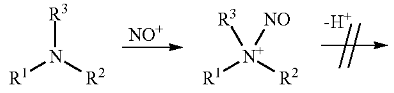

Certain tertiary amines have been observed to form stable nitrosamines. A plausible mechanism for the nitrosation of an alkyl dimethylamine is shown in Scheme III. In path (a), this tertiary amine undergoes a demethylation reaction, with loss of a methyl ($-CH_3$) group, providing alkyl methylamine intermediate Ia. This compound, a secondary amine, can undergo the nitrosation reaction set forth in Scheme I, above, affording nitrosamine IIa.

Alternatively, as shown in path (b), the tertiary amine instead undergoes a dealkylation reaction, with loss of the $R^1$ group, providing dimethylamine Ib. This compound, a secondary amine, can undergo the nitrosation reaction set forth in Scheme I, above, affording nitrosamine IIb, which is recognized as NDMA.

Scheme III

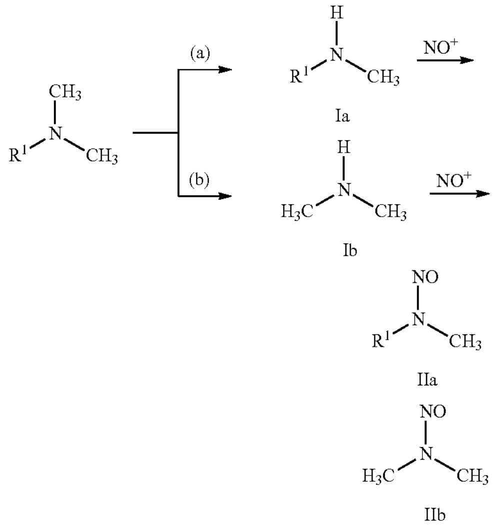

For completeness, an alternative mechanism is set forth in Scheme IV, in which the nitrosation step precedes the dealkylation/demethylation step. In this mechanism, formation of IIa and IIb proceeds from the cationic nitrosamine intermediate Ic via path (c) and path (d), respectively.

Scheme IV

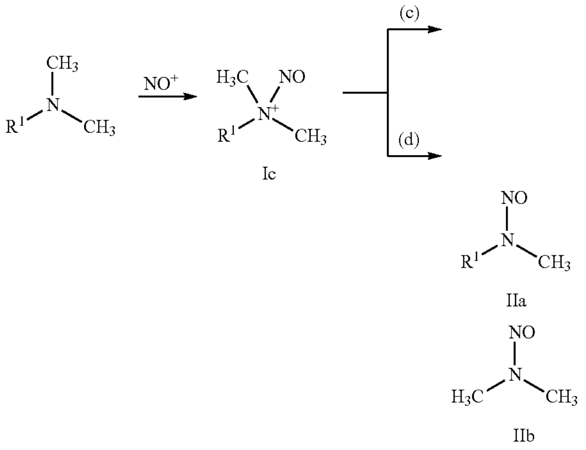

Several pharmaceutically important compounds are known to undergo dealkylation at some point during the nitrosation process. Ranitidine undergoes path (b), affording NDMA as its nitrosamine fragmentation product. A number of other compounds undergo path (a), leading to compounds that have lost a methyl group. These include the following pharmaceutical dosage forms: Almotriptan (Axert), Amitriptyline (Elavil), Azelastine (Optivar), Azithromycin (Zithromax, Azasite), Bedaquiline (Sirturo), Brompheniramine (Dimetapp), Cabergoline (Dostinex), Carbinoxamine (Histex, Histussis, Karbinal, Mintex, Palgic, Pediatex, Pediox, Ryvent), Chlophedianol (Clofedanol, Ninjacof), Chloropyramine, Chlorpheniramine, Chlorpromazine (Thorazine, Largactil), Citalopram (Celexa), Clarithromycin (Biaxin), Clomipramine (Anafranil), Clozapine, Cyclobenzaprine (Amrix, Flexeril), Demeclocycline (Declomycin), Desvenlafaxine (Pristiq), Dexbrompheniramine (Drixoril, Conex, Dixaphedrin), Dexchlorpheniramine (Polaramine), Diltiazem (Cartia, Tiazac, Cardizem), Diphenhydramine (Benadryl), Doxepin (Silenor, Zonalon, Prudoxin), Doxycycline, Doxylamine (Unisom), Eravacycline (Xerava), Erythromycin, Escitalopram (Lexapro, Cipralex), Imipramine (Tofranil), Levofloxacin (Levaquin, Iquix), Maralixibat (Livmarli), Masitinib (Masivet, Kinavet), Methadone (Dolophine), Methylene Blue (ProvayBlue), Mifepristone (RU486), Minocycline (Minocin), Mirtazapine (Remeron), Nintedanib (Vargatef, Ofev), Olopatadine (Patanol), Omadacycline (Nuzyra), Orphenadrine, Padimate O, Pheniramine (Avil), Phenyltoloxamine, Promethazine (Phenergan), Propoxyphene (Darvon), Pseudoephedrine (Sudafed, Sinutab), Pyrilamine (Mepyramine), Quinupristin, Rivastigmine (Exelon), Rizatriptan (Maxalt), Sarecycline (Seysara), Sildenafil (Viagra), Spinosad, Sumatriptan (Imitrex, Imigran), Tamoxifen (Nolvadex, Genox, Tamifen), Tapentadol (Nucynta), Telithromycin (Ketek), Tetracycline, Thonzylamine (Neohetramine), Tigecycline, Tramadol (Ultram), Trimebutine (Debridat, Recutin, Polybutin), Trimethobenzamide (Tebamide, Tigan), Trimipramine (Surmontil), Tripelennamine (Pyribenzamine), Ulipristal Acetate (Ella), Venlafaxine (Effexor), and Zolmitriptan (Zomig).

It will be appreciated that reactivity of various amines with nitrosating agents may be highly dependent on the nature of both the amine and the composition in which it is provided, particularly for a solid-state composition. However, it will also be appreciated that the decrease in nitrosamine and nitrosating content for Ranitidine, disclosed herein, suggests similar reactivity can be expected for similar compounds, i.e., the aforementioned pharmaceutical dosage forms.

Similarly, Lidocaine (Xylocaine) undergoes loss of —$CH_2CH_3$ (ethyl) to form a nitrosamine product, and Ropivacaine (Naropin, Rocaine) undergoes loss of —$CH_2CH_2CH_3$ (1-propyl) to form a nitrosamine product. It can be expected that these compounds may also undergo similar reactivity as that demonstrated for Ranitidine.

Optionally, the following APIs have similar chemical functionality, and may be reasonably expected to interact or react with active agents in a similar manner: Albuterol (Salbutamol, Ventolin), Atenolol (Tenormin), Betaxolol (Kerlone), Bisoprolol (Zebeta), Carteolol (Arteolol, Arteoptic, Calte, Cartéabak, Carteol, Carteol, Cartrol, Elebloc, Endak, Glauteolol, Mikelan, Ocupress, Poenglaucol, Singlauc, Teoptic), Celiprolol (Edisvo), Dipivefrin (Propine), Ephedrine (Akovaz), Epinephrine, Esmolol (Brevibloc), Isoproterenol (Isoproterenol), Levalbuterol (Levosalbutamol, Xopenex), Levobunolol (AKBeta, Betagan, Vistagan), Metoprolol (Lopressor), Nadolol (Corgard), Phenylephrine, Pindolol (Visken), Propranolol (Inderal), Racepinephrine, Sotalol (Betapace, Sorine, Sotylize), Terbutaline (Bricanyl, Marex), and Timolol (Betimol, Blocadren, Istalol, Timoptic).

Optionally, the following APIs have similar chemical functionality, and may be reasonably expected to interact or react with active agents in a similar manner: Amlodipine (Norvasc), Clevidipine (Cleviprex), Felodipine (Plendil), Finerenone (Kerendia), Isradipine (DynaCirc, Prescal), Levamlodipine, Nicardipine (Cardene), Nifedipine (Procardia), Nimodipine (Nimotop), and Nisoldipine (Sular).

Optionally, the following APIs have similar chemical functionality, and may be reasonably expected to interact or react with active agents in a similar manner: Benazepril (Lotensin), Cilazapril (Vascace, Dynorm), Enalapril (Vasotec), Enalaprilat (Vasotec), Lisinopril (Prinivil, Zestril, Qbrelis, Dapril), Moexipril (Univasc), Perindopril (Coversyl, Coversum, Aceon), Quinapril (Accupril), Ramipril (Altace), and Trandolapril (Mavik).

Optionally, the following APIs have similar chemical functionality, and may be reasonably expected to interact or react with active agents in a similar manner: Almotriptan (Axert), Amitriptyline (Elavil), Bedaquiline (Sirturo), Brompheniramine (Dimetapp), Cabergoline (Dostinex), Carbinoxamine (Histex, Histussis, Karbinal, Mintex, Palgic, Pediatex, Pediox, Ryvent), Chlophedianol (Clofedanol, Ninjacof), Chloropyramine, Chlorpheniramine, Chlorpromazine (Thorazine, Largactil), Citalopram (Celexa), Clomipramine (Anafranil), Cyclobenzaprine (Amrix, Flexeril), Dexbrompheniramine (Drixoril, Conex, Dixaphedrin), Dexchlorpheniramine (Polaramine), Diltiazem (Cartia, Tiazac, Cardizem), Diphenhydramine (Benadryl), Doxepin (Silenor, Zonalon, Prudoxin), Doxylamine (Unisom), Escitalopram (Lexapro, Cipralex), Imipramine (Tofranil), Olopatadine (Patanol), Orphenadrine, Pheniramine (Avil), Phenyltoloxamine, Pyrilamine (Mepyramine), Rizatriptan (Maxalt), Sumatriptan (Imitrex, Imigran), Tamoxifen (Nolvadex, Genox, Tamifen), Thonzylamine (Neohetramine), Trimethobenzamide (Tebamide, Tigan), Tripelennamine (Pyribenzamine), and Zolmitriptan (Zomig).

Optionally, the following APIs have similar chemical functionality, and may be reasonably expected to interact or react with active agents in a similar manner: Brompheniramine (Dimetapp), Carbinoxamine (Histex, Histussis, Karbinal, Mintex, Palgic, Pediatex, Pediox, Ryvent), Chloropyramine, Chlorpheniramine, Dexbrompheniramine (Drixoril, Conex, Dixaphedrin), Dexchlorpheniramine (Polaramine), Diphenhydramine (Benadryl), Doxylamine (Unisom), Olopatadine (Patanol), Pheniramine (Avil), Phenyltoloxamine, Pyrilamine (Mepyramine), Thonzylamine (Neohetramine), and Tripelennamine (Pyribenzamine).

Optionally, the following APIs have similar chemical functionality, and may be reasonably expected to interact or react with active agents in a similar manner: Abacavir (Ziagen), Apixaban (Eliquis), Argatroban, Avacopan (Tavneos), Avanafil (Stendra, Spedra), Belumosudil (Rezurock), Bendroflumethiazide (bendrofluazide, Aprinox), Benzonatate (Zonatuss), Brilliant Blue G, Bumetanide (Bumex), Cangrelor (Kengreal), Chloroquine (Aralen), Clozapine, Dabigatran (Pradaxa), Deucravacitinib (Sotyktu), Diclofenac (Voltaren), Duvelisib (Copiktra), Etravirine (Intelence), Florbetaben F-18 (NeuraCeq), Florbetapir F-18 (Amyvid), Flutemetamol F-18 (Vizamyl), Folic Acid, Fosdenopterin (Nulibry), Fostamatinib (Tavlesse, Tavalisse), Furosemide (Discoid, Lasix, Uremide), Hydrochlorothiazide (Hydrodiuril), Hydroxychloroquine (Plaquenil), Imatinib (Gleevec, Glivec), Leniolisib (Joenja), Leucovorin (Folinic acid), Levoleucovorin, Levomefolic Acid (Metafolin), Maribavir (Livtencity), Meclofenamic Acid (Meclomen), Mefenamic acid (Ponstel, Ponstan), Metolazone (Zytanix, Metoz, Zaroxolyn, Mykrox), Neratinib (Nerlynx), Olanzapine (Zyprexa), Omidenepag isopropyl (Eybelis), Ozenoxacin (Ozanex, Xepi), Pafolacianine (Cytalux), Polythiazide, Primaquine, Rifabutin, Rilpivirine (Edurant, Rekambys), Rivaroxaban (Xarelto), Sapropterin (Tetrahydrobiopterin, Kuvan, Biopten), Tafenoquine (Krintafel), Tetracaine (Pontocaine, Ametop, Dicaine), Torsemide (Torasemide).

Optionally, the following APIs have similar chemical functionality, and may be reasonably expected to interact or react with active agents in a similar manner: Acarbose (Merative, Micromedex), Ambroxol, Arformoterol (Brovana), Berotralstat (Orladeyo), Bicisate, Carvedilol (Coreg), Caspofungin (Cancidas), Cinacalcet (Sensipar), Dobutamine (Dobutrex), Elagolix (Orilissa), Ethambutol (Myambutol), Ethylisopropylamine, Exametazime (Ceretec), Formoterol (Perforomist), Labetalol (Normodyne, Trandate), Landiolol (Sibboran), Mirabegron (Myrbetriq, Betanis, Betmiga), Mitoxantrone (Novantrone), Nebivolol (Nebilet, Bystolic), Oliceridine (Olinvyk), Olodaterol (Striverdi Respimat), Oritavancin (Orbactiv), Ozanimod (Zeposia), Plazomicin (Zemdri), Plerixafor (Mozobil), Prilocaine (Citanest), Propafenone (Rythmol), Rasagiline (Azilect, Azipron), Rotigotine (Neupro), Rotigotine (Neupro), Safinamide (Xadago), Salmeterol (Serevent, Aeromax, Qitai), Silodosin (Urief), Tamsulosin (Flomax), Telavancin (Vibativ), Terbinafine (Lamisil), Terbinafine (Lamisil), Ticagrelor (Brilinta, Brilique), Trientine, Vilanterol, and Vildagliptin (Galvus).

Optionally, the following APIs have similar chemical functionality, and may be reasonably expected to interact or react with active agents in a similar manner: Alogliptin (Nesina, Vipidia), Amoxapine (Asendin), Arpraziquantel, Azacyclonol (Ataractan, Calmeran, Frenoton, Frenquel, Psychosan), Ciprofloxacin (Ciloxan, Cipro, Neofloxin), Clozapine, Daridorexant (Quviviq), Desloratadine (Clarinex, Aerius), Ertapenem (Invanz), Flecainide (Tambocor), Gatifloxacin (Gatiflo, Tequin, Zymar, Zymaxid), Ivacaftor (Kalydeco), Levofloxacin (Levaquin, Iquix), Masitinib (Masivet, Kinavet), Mefloquine (Lariam), Meropenem (Merrem), Methylphenidate (Ritalin, Concerta), Migalastat (Galafold), Mirtazapine (Remeron), Mitapivat (Pyrukynd), Moxifloxacin (Avelox, Vigamox, Moxiflox), Nintedanib (Vargatef, Ofev), Paroxetine (Paxil, Seroxat, Loxamine), Proline, Quetiapine (Seroquel), Quetiapine (Seroquel), Ranolazine (Ranexa, Aspruzyo Sprinkle, Corzyna), Ranolazine (Ranexa, Aspruzyo Sprinkle, Corzyna), Relebactam, Ribociclib (Kisqali), Rifampicin (Rifadin), Risdiplam (Evrysdi), Rolapitant (Varubi), Ropivacaine (Naropin, Rocaine), Sildenafil (Viagra), Sitagliptin (Januvia, Zituvio), Terazosin (Hytrin, Zayasel), Terazosin (Hytrin, Zayasel), Tirofiban (Aggrastat), Trimetazidine, Vibegron (Gemtesa), and Vortioxetine (Trintellix, Brintellix).

Optionally, the following APIs have similar chemical functionality, and may be reasonably expected to interact or react with active agents in a similar manner: Cariprazine (Vraylar), Celiprolol (Cardem, Selectol, Celipres, Celipro, Celol, Cordiax, Dilanorm), Lisuride (Dopergin), Mozenavir, Redafamdastat, Ritonavir (Norvir), Telinavir, and Telcagepant.

Optionally, pharmaceutical dosage forms that are within the same classification or category (e.g., ACE inhibitors, sartans, and like classifications) may be reasonably expected to interact or react with active agents in a similar manner to decrease, mitigate, remove or preclude the formation of an amount of N-nitroso compounds and/or nitrosating agents. It will be appreciated that the following pharmaceutical drugs within the same groupings may be similarly susceptible to an N-nitroso compound and/or a nitrosating agent decrease, mitigation, removal or preclusion by the same active agent. Almotriptan, Frovatriptan, Rizatriptan, Sumatriptan, Zolmitriptan, and Mirtazapine may interact or react similarly to an active agent because they are all 5-HT18 receptor agonists; Tamsulosin, Silodosin, and Urapidil are all α1A-adrenergic receptor antagonists; Benazepril, Cilasapril, Enalapril, Enalaprilat, Lisinopril, Moexipril, Prindopril, Quinapril, Ramipril, and Trandolapril are all ACE inhibitors; Ephedrine, Epinephrine, Isoproterenol, Phenylephrine, Propylhexedrine, Racepinephrine, and Labetalol are all Adrenergic receptor agonists; Lidocaine, Prilocaine, Ropivacaine, and Terracaine are all amino amide anaesthetics; Azithromycin, Colistin, Ethambutol, Oritavancin, Plazomicin, Quinupristin, Rifatutin, Rifampiin, Streptomycin, Televancin, Telithromycin, and Vancomycin are all Antibacterials, Azelastine, Brompheniramine, Carbinoxamine, Chloropyramine, Chloropheniramine, Desloratadine, Dexbrompheniramine, Dexchlorpheniramine, Diphenhydramine, Doxylamine, Olopatadine, Pheniramine, and Phenyltoloxamine are all Antihistamines; Amprenavir (Agenerase), Asunaprevir (Sunvepra), Atazanavir (Reyataz, Evotaz), Boceprevir (Victrelis), Darunavir (Prezista, Prezcobix, Prezista, Rezolsta), Fosamprenavir (Lexiva, Telzir), Glecaprevir (Maviret, Mavyret), Grazoprevir (Zepatier), Indinavir (Crixivan), Lopinavir, Mozenavir, Nelfinavir (Viracept), Paritaprevir, Ritonavir (Norvir), Saquinavir (Invirase), Simeprevir (Olysio, Sovriad, Galexos), Telaprevir (Incivek, Incivo), Telinavir, and Tipranavir (Aptivus) are all protease inhibitors; Amprenavir (Agenerase), Atazanavir (Reyataz, Evotaz), Darunavir (Prezista, Prezcobix, Prezista, Rezolsta), Fosamprenavir (Lexiva, Telzir), Indinavir (Crixivan), Lopinavir, Mozenavir, Nelfinavir (Viracept), Ritonavir (Norvir), Saquinavir (Invirase), Telinavir, and Tipranavir (Aptivus) are all HV-1 protease inhibitors; and Asunaprevir (Sunvepra), Boceprevir (Victrelis), Grazoprevir (Zepatier), Glecaprevir (Maviret, Mavyret), Paritaprevir, Simeprevir (Olysio, Sovriad, Galexos), and Telaprevir (Incivek, Incivo) are all Hepatitis C virus NS3/RA protease inhibitors.

Optionally, to the extent that any of the above-disclosed APIs form, emit or include an amount of N-nitroso compound and/or nitrosating agent, solutions presented herein according to the disclosed concept may be utilized to decrease, mitigate, remove or preclude the formation of such N-nitroso compound and/or nitrosating agent in connection with packaging for drugs containing such APIs.

Optionally, pharmaceutical dosage forms that include the same excipient, such as but not limited to microcrystalline cellulose (MCC) may be reasonably expected to interact or react with active agents in a similar manner to decrease, mitigate, remove or preclude the formation of an amount of N-nitroso compounds and/or a nitrosating agents.

Without intending to be bound by any particular theory, primary sources of the formation of N-nitroso compounds and/or nitrosating agents in a pharmaceutical dosage form includes: (i) raw material impurities found in excipients and chemically synthesized API's along with reagents, solvents and catalysts wherein cross-contamination may result due to different processes run on the same production lines; (ii) degradation of the actual drug product due to exposure to heat or certain classes of compounds, e.g., dimethylamine, which have a chemical structure that inherently contains secondary or tertiary amines; and (iii) degradation of packaging materials including lacquers, inks, and other materials.

Optionally, the active agents that are effective to decrease, mitigate, remove or preclude formation of an amount of N-nitroso compounds and/or nitrosating agents resulting from a pharmaceutical dosage form itself or the storage of a pharmaceutical dosage form in a container are selected from: vitamin E, sodium chloride, sodium hydroxide, potassium hydroxide, ferulic acid, sodium bicarbonate, calcium carbonate, sodium carbonate, magnesium carbonate, sodium alginate, lycopene, ascorbic acid, 3 A or 4 A molecular sieve, calcium sulfate, hydrochloric acid, ferric oxide, vitamin A, silica gel, magnesium chloride, and polymer-based oxygen scavenger. Also optionally, the active agents that are effective to decrease, mitigate, remove or preclude formation of an amount of N-nitroso compounds and/or nitrosating agents resulting from a pharmaceutical dosage form itself or the storage of a pharmaceutical dosage form in a container are selected from: ascorbic acid, vitamin E, sodium chloride, sodium bicarbonate, calcium carbonate, magnesium carbonate, silica gel, and polymer-based oxygen scavenger. Optionally, when the active agent is sodium chloride, the entrained polymer component is free from or substantially free from a metallic material, optionally wherein the metallic material is iron.

Without intending to be bound by any particular theory, certain reactions that decrease the amount of, or preclude the formation of, N-nitroso compounds, such as N-nitrosamines, may involve oxidation/reduction ("redox") steps. For this reason, active agents that have similar redox behavior, including but not limited to: electronic configuration, propensity for 1- or 2-electron processes, and electrode potential, may be expected to perform similarly.

Without intending to be bound by any particular theory, certain reactions that decrease the amount of, or preclude the formation of, N-nitroso compounds, such as N-nitrosamines, may involve acid/base reactions. Furthermore, the protonation state of various species and moieties, including but not limited to nitrous acid, carboxylic acids, e.g., in the active agent, and amine moieties susceptible to N-nitrosation reactions, may affect these reactions. For this reason, active agents that have similar acid/base behavior, including but not limited to: the nature of the conjugate base/conjugate acid and pKa, may be expected to perform similarly.

Without intending to be bound by any particular theory, certain reactions that decrease the amount of, or preclude the formation of, N-nitroso compounds, such as N-nitrosamines, may involve volatile, functionalized molecules that may be susceptible to absorption or adsorption processes by certain materials. For this reason, active agents that comprise materials with similar absorbing/adsorbing behavior may be expected to perform similarly.

Optionally, active solutions according to the invention are effective to decrease or eliminate N-nitroso compound or nitrosating agent molecules post formation in the headspace of the drug packaging.

Optionally, the active agents that are effective to decrease, mitigate, remove or preclude the formation of an amount of N-nitroso compounds resulting from certain pharmaceutical dosage forms may be extended to predict their effectiveness to others that are produced by certain manufacturing processes and/or use of certain raw materials. It will be appreciated that drugs in the same class may be manufactured using the same or similar processes and raw materials and therefore, may be reasonably expected to interact or react with active agents in a similar manner to decrease N-nitroso compounds.

Optionally, the pharmaceutical dosage form that is mitigated through the methods, materials and systems disclosed herein does not comprise any one of rifampicin, rifapentine, or gliclazide. Optionally, the pharmaceutical dosage form that is mitigated through the methods, materials and systems disclosed herein does not comprise a compound with either a hydrazone or a semicarbazide moiety. Optionally, the pharmaceutical dosage form that is mitigated through the methods, materials and systems disclosed herein does not comprise a compound that can undergo hydrolysis to provide a primary hydrazine.

It will be understood that the materials and methods disclosed herein may be of general applicability to NOCs, including, but not limited to, N-nitrosamines, N-nitrosamides, N-nitrosoureas, and N-nitrosoguanidines.

Without intending to be bound by a particular theory, it is thought that certain amines, particularly secondary amines $R^1R^2NH$, are susceptible to nitrosation by nitrous acid, nitrites and other nitrosating agents to form N-nitrosamines, which are generally genotoxic and/or carcinogenic. Nitrosation can generally take place at any time during synthesis, formulation, or storage of the medicament.

In certain embodiments, nitrosamines having the formula $R^1R^2N—NO$ are produced during decomposition of the product or medicament, with $R^1$ and $R^2$ independently chosen from alkyl, or $R^1$, $R^2$, and the intervening nitrogen combine to form an optionally substituted heterocycloalkyl. Optionally, the nitrosamine $R^1R^2N—NO$ is formed from secondary amine $R^1R^2NH$, present either in the product or medicament, as a contaminant in the product or medicament formed during synthesis or formulation, or as a decomposition product, reacting with nitrous acid and/or nitrite.

Without limitation, compounds having partial chemical structure $R^1R^2N—C(=X^1)—X^2—$, with $X^1$ and $X^2$ independently chosen from NH, O, and S, may undergo fragmentation to provide secondary amine $R^1R^2NH$.

Without limitation, compounds having a partial chemical structure $R^1R^2N—N=C—$ may undergo fragmentation to provide secondary amine $R^1R^2NH$.

Without limitation, compounds having a partial chemical structure $R^1R^2N—C(=NH)—NH—C(=NH)—$ may undergo fragmentation to provide secondary amine $R^1R^2NH$.

Optionally, a compound or medicament having a partial chemical structure $R^1R^2N—$ can undergo a two-step process of nitrosation and fragmentation to produce nitrosamine $R^1R^2N—NO$. Optionally, compounds having partial chemical structure $R^1R^2N—CH_2—Ar$, with Ar being an optionally substituted aryl or heteroaryl moiety, can undergo the two-step nitrosation/fragmentation process to produce nitrosamine $R^1R^2N—NO$.

Optionally, an excipient used in the formulation of a compound or medicament may comprise nitrous acid and/or nitrite capable of reacting with a secondary or tertiary amine in the compound or medicament to produce nitrosamine $R^1R^2N—NO$. Optionally, the excipient is microcrystalline cellulose (MCC), colloidal silicon dioxide, hypromellose (HPMC), povidone, mannitol, talc, sodium lauryl sulfate, polyvinyl alcohol, sodium starch glycolate, hydroxypropyl cellulose, poloxamer, citric acid, sodium chloride, sucrose, magnesium stearate, lactose monohydrate, corn starch, starch, croscarmellose sodium, polyethylene glycol, or crospovidone.

In certain embodiments, nitrosamine impurities, such as N-nitrosodimethyl amine (NDMA), N-nitrosodiethyl amine (NDEA), and N-nitrosodiisopropyl amine (NDIPA), result from nitrosable compounds, such as primary, secondary amines, e.g., diethylamine, or tertiary amines, or quaternary ammonium salts, reacting with nitrosating agents, such as nitrous acid, that are formed in-situ from nitrites, such as sodium nitrite.

Optionally, the active agent as a scavenging material binds to a portion of the N-nitroso compound, thereby removing the portion of the N-nitroso compound from the gas phase. Optionally, the scavenging material binds in a substantially reversible manner. Optionally, the scavenging material binds in a substantially irreversible manner. Optionally, the process of binding of the scavenging material to the N-nitroso compound involves formation of a covalent bond. Optionally, the scavenging material binds to the N-nitroso compound in a noncovalent manner.

Optionally, a portion of the N-nitroso compound undergoes a chemical reaction in the presence of the scavenging material, thereby removing the portion of the N-nitroso compound from the gas phase. Optionally, the chemical reaction is an oxidation. Optionally, the chemical reaction is a reduction. Optionally, the chemical reaction is an addition. Optionally, the chemical reaction is a cycloaddition. Optionally, the chemical reaction is mediated by a radical process.

Optionally, the scavenging material comprises an acid. Optionally, the acid increases the binding affinity of the scavenging material for the N-nitroso compound. Optionally, the acid promotes a chemical reaction of a portion of the N-nitroso compound.

Optionally, the product or medicament contains an N-nitroso compound prior to packaging. Optionally, the container provides sufficient scavenging ability to decrease the amount of N-nitroso compound to below a hazardous level, during a storage period, subsequent to packaging, of 52 weeks, optionally 26 weeks, optionally 13 weeks, optionally 8 weeks, optionally 4 weeks, optionally 2 weeks, optionally 1 week. Optionally, the scavenging material is effective such that the standard daily dosage of the medicament does not exceed 96 ng for NDMA or NMBA, or 26.5 ng for NDEA, NMPA, NIPEA or NDIPA.

Optionally, the product or medicament contains an N-nitroso compound prior to packaging. Optionally, the N-nitroso compound is formed during storage of the product or medicament in the absence of any preventative measures. Optionally, the container provides sufficient scavenging ability to prevent accumulation of N-nitroso compound, to a hazardous level, during a storage period, subsequent to packaging, of 1 week, optionally 2 weeks, optionally 4 weeks, optionally 6 weeks, optionally 13 weeks, optionally 26 weeks, optionally 52 weeks. Optionally, the scavenging material is effective such that the standard daily dosage of the medicament does not exceed 96 ng for NDMA or NMBA, or 26.5 ng for NDEA, NMPA, NIPEA or NDIPA.

Optionally, the product or medicament is stored within the container at substantially ambient temperature.

Optionally, during the period of storage, the container does not exceed a maximum temperature of 50° C. In further embodiments, the maximum temperature is 45° C. or lower, optionally 40° C. or lower, optionally 35° C. or lower, or optionally 30° C. or lower.

Optionally, during the period of storage, the container does not drop below a minimum temperature of −40° C. In further embodiments, the minimum temperature is −35° C. or higher, optionally −30° C. or higher, optionally −25° C. or higher, optionally −20° C. or higher, optionally −15° C. or higher, optionally −10° C. or higher, optionally −5° C. or higher, optionally 0° C. or higher, optionally 5° C. or higher, optionally 10° C. or higher, or optionally 15° C. or higher, optionally 20° C. or higher.

In certain embodiments, the scavenging material is provided in at least one entrained polymer component. In certain embodiments, the scavenging material satisfies the requirements for "active agent" defined herein.

In certain embodiments, the entrained polymer component comprises a base polymer and optionally a channeling agent.

In certain embodiments, the base polymer ranges from 10% to 70%, optionally from 20% to 60%, optionally from 20% to 50%, optionally from 20% to 40%, optionally from 30% to 70%, optionally from 30% to 60%, from 30% to 50%, optionally from 40% to 70%, optionally from 40% to 60%, optionally from 40% to 50% by weight of the total composition.

In certain embodiments, the channeling agent is in a range from 1% to 20%, optionally 1% to 15%, optionally 1% to 10%, optionally 1% to 5%, optionally from 5% to 20%, optionally 5% to 15%, optionally 5% to 10%, optionally from 10% to 20%, optionally from 10% to 15% by weight with respect to the total weight of the entrained polymer.

Optionally, the container further comprises a desiccant. Optionally, the desiccant comprises molecular sieve, silica or silica gel.

Optionally, the container blocks light and/or UV radiation.

Certain embodiments disclosed herein provide methods to obtain a pharmaceutically active composition in a form that is substantially free of N-nitroso compounds and/or nitrosating agents, such as nitrite and $NO_x$. In some embodiments, the composition contains less than 1500 ppm, optionally less than 400 ppm, optionally less than 100 ppm, optionally less than 95 ppm, optionally less than 90 ppm, optionally less than 85 ppm, optionally less than 80 ppm, optionally less than 75 ppm, optionally less than 70 ppm, optionally less than 65 ppm, optionally less than 60 ppm, optionally less than 55 ppm, optionally less than 50 ppm, optionally less than 45 ppm, optionally less than 40 ppm, optionally less than 35 ppm, optionally less than 25 ppm, optionally less than 20 ppm, optionally less than 15 ppm, optionally less than 14 ppm, optionally less than 13 ppm, optionally less than 12 ppm, optionally less than 11 ppm, optionally less than 10 ppm, optionally less than 9 ppm, optionally less than 8 ppm, optionally less than 7 ppm, optionally less than 6 ppm, optionally less than 5 ppm, optionally less than 4 ppm, optionally less than 3 ppm, optionally less than 2 ppm, optionally less than 1 ppm, optionally less than 0.9 ppm, optionally less than 0.8 ppm, optionally less than 0.7 ppm, optionally less than 0.6 ppm, optionally less than 0.5 ppm, optionally less than 0.4 ppm, optionally less than 0.3 ppm, optionally less than 0.2 ppm, optionally less than 0.1 ppm of total N-nitroso compound. In some embodiments, the standard daily dosage for the composition contains less than 400 ng, optionally less than 200 ng, optionally 96 ng or less, optionally less than 50 ng, optionally 26.5 ng or less, optionally less than 25 ng, optionally less than 20 ng, optionally less than 10 ng, optionally less than 5 ng. In some embodiments, the dosage for the composition contains less than 100%, optionally less than 90%, optionally less than 80%, optionally less than 70% of the FDA or EMA permitted content in effect as of 1 Jan. 2024.

Certain embodiments disclosed herein provide methods to decrease, mitigate, remove or preclude the formation of an amount of N-nitroso compounds and/or nitrosating agents, such as nitrites and $NO_x$, in a pharmaceutically active composition. In some embodiments, a decrease in the amount of the N-nitroso compounds and/or nitrosating agents is accomplished by scavenging the N-nitroso compounds and/or nitrosating agents. In some embodiments, a decrease in the amount of the N-nitroso compound is accomplished by decreasing the amount of a primary hydrazine in the composition. In some embodiments, a decrease in the amount of the N-nitroso compound is accomplished without decreasing the amount of a primary hydrazine in the composition. In some embodiments, a decrease in the amount of the N-nitroso compound is accomplished by hydrolyzing a hydrazone or semicarbazone in a compound comprising the pharmaceutically active composition. In some embodiments, a decrease in the amount of the N-nitroso compound is accomplished without hydrolyzing a hydrazone or semicarbazone in a compound comprising the pharmaceutically active composition.

Also provided are embodiments wherein any embodiment above may be combined with any one or more of these embodiments, provided the combination is not mutually exclusive.

As used herein, two embodiments are "mutually exclusive" when one is defined to be something which is different than the other.

Definitions

As used herein, the terms below have the meanings indicated.

List of Abbreviations au=arbitrary units; GC=gas chromatography; GC-MS (or GC-MSD)=gas chromatography-mass spectrometry; h=hour; NDMA=N-nitrosodimethylamine; NDEA=N-nitrosodiethylamine; NDPA=N-nitrosodi-1-propylamine; NDIPA=N-nitrosodi-2-propylamine; NDBA=N-nitrosodi-1-butylamine; NEIPA=N-nitroso-N-ethyl-2-propylamine; NMP=N-nitroso-N-methylpiperazine; CPNP=N-nitroso-N-cyclopentylpiperazine; NPYR=N-nitrosopyrrolidine; TG-DTA=thermogravimetry/differential thermal analysis; TPSR=temperature programmed surface reaction.

Unless otherwise noted, the following material designations are used herein: "HDPE" or "HDPE 3954" refers to HDPE B03954P; "EVA" or "EVA-2528" refers to Celanese Ateva® EVA 2820A; Eval EVOH 0738 refers to EVAL™ EVOH from Kuraray; "CC1020014" refers to CC10200143WE, consisting of cobalt neodecanoate in ExxonMobil Exceed™ PP9074MED polypropylene, provided as a masterbatch by Avient; "Carbowax" refers to CARBOWAX™ SENTRY™ Polyethylene Glycol 4000 NF; "3040" refers to EXACT™ 3040; "ELVAX" refers to ELVAX™ 3174 ethylene vinyl acetate from Dow Chemical; and HD8960 refers to HDPE 8960 from Trademark Plastics.

As used herein, the term "selected material" is defined as a material that is acted upon, by, or interacts or reacts with an active agent and is capable of being transmitted through the channels of an entrained polymer. The selected material of primary focus in this specification are nitrosamines and nitrosating agents, such as nitrites and $NO_x$.

As used herein, the term "amine" refers to a compound $R^1R^2R^3N$, with $R^1$, $R^2$, and $R^3$ being unlimited, with the exception that an amine moiety is neither a $R^4C(=O)NR^2R^3$ (carboxamide) or a $R^4SO_2NR^2R^3$ (sulfonamide) moiety. It will be understood that many organic compounds contain e.g. both amine and carboxamide moieties, and the existence of a carboxamide moiety in one part of a molecule does not preclude the existence of an amine moiety elsewhere in the compound, as is the case for e.g. peptides and proteins. In some embodiments, $R^1$, $R^2$, and $R^3$ are groups independently chosen from H, alkyl, cycloalkyl, heterocycloalkyl, aryl, and heteroaryl, any of the groups, with the exception of H, may be optionally substituted, and two of $R^1$, $R^2$, and $R^3$ can combine to form a ring. The definition therefore excludes compounds wherein any one of $R^1$, $R^2$, and $R^3$ can be expressed as $R^4C(=O)—$ or $R^4SO_2—$.

The term "primary amine" refers to an amine wherein two of $R^1$, $R^2$, and $R^3$ are H. The term "secondary amine" refers to an amine wherein one of $R^1$, $R^2$, and $R^3$ are H. The term "tertiary amine" refers to an amine wherein none of $R^1$, $R^2$, and $R^3$ is H. The term "cyclic amine" refers to an amine wherein two of $R^1$, $R^2$, and $R^3$ combine to form a ring. The term "acyclic amine" refers to an amine wherein no two of $R^1$, $R^2$, and $R^3$ combine to form a ring. The term "aliphatic amine" refers to an amine wherein $R^1$, $R^2$, and $R^3$ are independently chosen from H and alkyl, and two of $R^1$, $R^2$, and $R^3$ can combine to form a ring. The term "aryl amine" refers to an amine wherein at least one of $R^1$, $R^2$, and $R^3$ is aryl.

As used herein, the term "N-nitroso compound" refers to a compound having an >N—N=O moiety. An N-nitroso compound may also be designated as $R^1R^2N—NO$, with no limit on the nature of the $R^1$ and $R^2$ moieties. It will be appreciated that certain N-nitroso compounds are relatively unstable, particularly for compounds with either $R^1$ or $R^2$=hydrogen. Representative N-nitroso compounds include nitrosamines, nitrosamides, including but not limited to compounds such as $(R^1CO)(R^2)N—NO$, nitrosoureas, including but not limited to compounds such as $(R^1NHCO)(R^2)N—NO$, and nitrosoguanidines, including but not limited to $[R^1NC(=N)NH][R^2]N—NO$.

As used herein, the term "N-nitrosamine" or alternatively "nitrosamine", is used to refer to the corresponding nitrosamine of an amine. It will be recognized that the definition excludes corresponding nitrosamines of tertiary amines, i.e., amines having the formula $R^1R^2R^3N$, wherein none of $R^1$, $R^2$, and $R^3$ is H, since formation of a nitrosamine from an amine requires loss of an $H^+$ for charge neutrality.

In accordance with the above definition of an amine, a nitrosamine moiety is neither a $R^4C(=O)NR^2$ (N-nitrosocarboxamide) or a $R^4SO_2NR^2$ (N-nitrososulfonamide) moiety.

In some embodiments, the nitrosamine may also be designated as $R^1R^2N—NO$, with $R^1$ and $R^2$ being groups independently chosen from H, alkyl, cycloalkyl, heterocycloalkyl, aryl, and heteroaryl; any of the groups, with the exception of H, may be optionally substituted; and two of $R^1$, $R^2$, and $R^3$ can combine to form a ring. The definition therefore excludes compounds wherein either one of $R^1$ and $R^2$ can be expressed as $R^4C(=O)—$ or $R^4SO_2—$. It will be appreciated that certain nitrosamines are relatively unstable, particularly for compounds with either $R^1$ or $R^2$=hydrogen.

Certain nitrosamines have a low molecular weight. It will be appreciated in the art that, all else being equal, increased molecular weight correlates with reduced volatility; therefore low molecular weight nitrosamines tend to be volatile. A low molecular weight nitrosamine may optionally be characterized as having a formula weight of 300 g/mol or less, optionally 200 g/mol or less, optionally 160 g/mol or less, optionally 120 g/mol or less. Optionally, volatile nitrosamines may be characterized as having a vapor pressure at 20° C. of 0.2 Torr or higher, optionally 0.5 Torr or higher, optionally 1 Torr or higher, optionally 2 Torr or higher, optionally 3 torr or higher, optionally 4 Torr or higher, or optionally 5 Torr or higher. Optionally, volatile amines may be characterized as having a boiling point at atmospheric pressure of 250° C. or lower, optionally 225° C. or lower, optionally 200° C. or lower, optionally 190° C. or lower, optionally 180° C. or lower, optionally 170° C. or lower, or optionally 160° C. or lower.

As used herein, the term "active agent" is defined as a material that acts on, or interacts or reacts with an N-nitroso compound, such as but not limited to nitrosamines, and/or a nitrosating agent, such as nitrite and $NO_x$. When in the form of an entrained polymer component including a base polymer and a channeling agent, the active agent is preferably immiscible with the base polymer and when mixed and heated with the base polymer and the channeling agent, will not melt, i.e., has a melting point that is higher than the melting point for either the base polymer or the channeling agent. The term "active agent" may include but is not limited to materials that absorb, adsorb, or release the N-nitroso compound and/or nitrosating agent. The "active agent" may include a "scavenging material". Optionally, the scavenging material may be an oxygen scavenging material. Optionally, the scavenging material may be a nitrite scavenging material. Optionally, the nitrite scavenging material is an arylamine. Optionally, the active agent can be reducing agent. Optionally the reducing agent is a 1- or 2-electron reducing agent. Optionally, the preferred active agents in the present disclosure may be ascorbic acid, vitamin E, sodium bicarbonate, sodium chloride, calcium carbonate, and magnesium carbonate, silica gel, and polymer-based oxygen scavenger.

The active agent can be provided in various forms or formats including, but not limited to, a film such as an extruded film, a cast film or a blow-molded film, coating, powder, puck, cannister, or sachet. Optionally, the active agent can be provided in or a component of a blow-molded bottle (blown bottle). Optionally, the active agent is provided in a film or other component within a blister pack.

As used herein, a substituted alkyl group refers to an alkyl group in which one or more hydrogens of the alkyl group is substituted with groups X, each individually chosen unless specified otherwise. In some embodiments, X is chosen from halo, cyano, hydroxy, oxo, acyl, acyloxy, alkyl, alkoxy, aryl, aryloxy, cycloalkyl, cycloalkyloxy, heterocycloalkyl, heterocycloalkyloxy, heteroaryl, and heteroaryloxy, with each of these terms as defined herein. In some embodiments, X is chosen from halo, cyano, hydroxy, oxo, acyl, alkyl, aryl, cycloalkyl, heterocycloalkyl, and heteroaryl, with each of these terms as defined herein. In some embodiments, X is chosen from halo, cyano, hydroxy, and oxo, with each of these terms as defined herein.

As used herein, the term "base polymer" is a polymer optionally having a gas transmission rate of a selected material that is substantially lower than, lower than or substantially equivalent to, that of the channeling agent. By way of example, such a transmission rate is a vapor transmission rate in embodiments where the selected material is an N-nitroso compound and the active agent is a scavenging material capable of removing an N-nitroso compound from a volume of gas in contact with the entrained polymer. The primary function of the base polymer is to provide structure or a blended form for the entrained polymer component.

As used herein, the term "polymer" refers to a compound composed of a linear chain of monomers. A polymer can be further defined as a "homopolymer", which is composed of identical monomers, and may be represented as $(\text{-A-})_n$, with integer subscript n indicating the degree of polymerization.

Degree of polymerization is often provided as subscript n to a monomer A, giving $(\text{-A-})_n$ or a similar expression. It will be understood that the number of monomers for individual molecules in a quantity of polymeric material can deviate from the degree of polymerization. In general, integer subscript n, termed the degree of polymerization, is without limit, and represents the average number of monomers in each polymer molecule in a polymer material. It will further be understood that the expression $(\text{—X—})_n$ is frequently used in the art to represent a polymeric material, and the absence of an accompanying numeric value or range for n in a particular expression should be construed as having a degree of polymerization without limit. In some embodiments, n is below 5000, optionally below 2000, optionally below 1000, optionally below 500, optionally below 200, optionally below 100, optionally below 50. In some embodiments, the degree of polymerization is greater than 50, optionally greater than 100, optionally greater than 200, optionally greater than 500, optionally greater than 1000. In some embodiments, n is between 50 and 5000, optionally between 100 and 2500, optionally between 200 and 2000, optionally between 500 and 1500. In some embodiments, the degree of polymerization is between 100 and 5000. In some embodiments, the degree of polymerization is between 200 and 2000. In some embodiments, the degree of polymerization is between 500 and 5000.

A polymer can be further defined as a "copolymer", which is composed of two or more types of monomers, for example "A" and "B". The term "copolymer" can further be subdivided into "random copolymers", for which no regular pattern exists for occurrence of either "A" or "B" in a polymer chain, "alternating copolymers", which may be represented as -A-B-A-B- etc., and "block copolymers", which consist of contiguous sequences of monomers interspersed with each other, e.g. -A-A-A-B-B-B-A-A-A- etc. In general, the number of each type of monomer in contiguous sequences of the monomer is without limit, and the number need not be uniform in either the quantity of polymer or in an individual strand. Unless otherwise indicated, the degree of polymerization n for a copolymer represents the average number of monomers, of all types, in each polymer molecule in a polymer material.

As used herein, the term "polyolefin" refers to a polymer with formula $(\text{—}CH_2CHR\text{—})_n$, with R chosen from H, alkyl, chloro, aryl, hydroxy, acyloxy, acetoxy, carboxy, and alkoxycarbonyl. In some embodiments, R is chosen from H, alkyl, and phenyl. In some embodiments, R is chosen from H and $C_{1-10}$alkyl. In some embodiments, R is chosen from H and $CH_3$. In some embodiments, the polyolefin is chosen from polyethylene, low-density polyethylene ("LDPE"), linear low-density polyethylene (LLDPE), very-low-density polyethylene (VLDPE), ultra-low-density polyethylene (ULDPE), and medium-density polyethylene (MDPE).

As used herein, the term "polyester" refers to a polymer with formula $(\text{—X—COO—})_n$, with X being a bivalent organic moiety. In some embodiments, the polyester has the formula $(\text{—CHRCOO—})_n$, with R chosen from H and $C_{1-10}$alkyl. In some embodiments, the polyester has the formula $((\text{—}CH_2)_mCOO\text{—})_n$, wherein m is chosen from 1, 2, 3, 4, and 5. In some embodiments, the polyester has the formula $(\text{—OOC—Y—COO—Z})_n$, with Y and Z both being bivalent organic moieties. In some embodiments, Y=1,4-phenylene. In some embodiments, Z is chosen from ethylene, butylene (tetramethylene), hexylene (hexamethylene), and 1,4-cyclohexenedimethylene. In some embodiments, the polyester is polyethylene terephthalate ("PET"). In some embodiments, the polyester is poly-1, 4-cyclohexylene-dimethylene terephthalate ("PCDT").

Suitable base polymers for use in the disclosure include thermoplastic polymers, e.g., polyolefins such as polypropylene and polyethylene, polyisoprene, polybutadiene, polybutene, polysiloxane, polycarbonates, polyamides, ethylene-vinyl acetate copolymers, ethylene-methacrylate copolymer, poly(vinylchloride), polystyrene, polyesters, polyanhydrides, polyacrylianitrile, polysulfones, polyacrylic ester, acrylic, polyurethane and polyacetal, or copolymers or mixtures thereof.

In certain embodiments, the channeling agent has a vapor transmission rate of at least two times that of the base polymer. In other embodiments, the channeling agent has a vapor transmission rate of at least five times that of the base polymer. In other embodiments, the channeling agent has a vapor transmission rate of at least ten times that of the base polymer. In still other embodiments, the channeling agent has a vapor transmission rate of at least twenty times that of the base polymer. In still another embodiment, the channeling agent has a vapor transmission rate of at least fifty times that of the base polymer. In still other embodiments, the channeling agent has a vapor transmission rate of at least one hundred times that of the base polymer.

As used herein, the term "channeling agent" or "channeling agents" is defined as a polymer material that is immiscible with the base polymer and has an affinity to transport a fluid (liquid or gas phase) substance at a faster rate than the base polymer. Optionally, a channeling agent is capable of forming channels through the entrained polymer when formed by mixing the channeling agent with the base polymer. Optionally, such channels are capable of transmitting a selected material through the entrained polymer component at a faster rate than in solely the base polymer.

As used herein, the term "channels" or "interconnecting channels" is defined as passages formed of the channeling agent that penetrate through the base polymer and may be interconnected with each other.

As used herein, the term "entrained polymer" or "entrained polymer component" is defined as a monolithic material in a blended form including at least a base polymer, an active agent, and optionally also a channeling agent entrained or distributed throughout. An entrained polymer or entrained polymer component thus has at least two phases (without a channeling agent) or at least three phases (with a channeling agent).

As used herein, the term "headspace" is defined as the volume within a package that is not occupied by the good or product stored therein. The singular term "headspace" typically, but not necessarily, refers to a contiguous volume. Use of the term "headspace" does not imply a lower limit to volume. Optionally, a headspace can be filled with a gas, or a mixture of gases, whose composition differs from that of atmosphere. Unless otherwise indicated, the gas within the headspace does not undergo appreciable exchange with the exterior atmosphere.

Some packages may provide separate compartments for individual units of the good or product, including but not limited to individual tablets or, alternatively, groups of tablets, each contained within a single compartment, and the headspace of each of which being isolated from other compartments in the package. Such package is described as having a plurality of headspaces, one for each of the compartments. A blister package is an example of a package with a plurality of headspaces. The design of such a package allows the retrieval of a single unit of the good or product, while keeping intact the remainder of the compartments in the package.

As used herein, the term "monolithic," "monolithic structure" or "monolithic composition" is defined as a composition or material that does not consist of two or more discrete macroscopic layers or portions. Accordingly, a "monolithic composition" does not include a multi-layer composite (although a monolithic composition can be a layer of a multi-layer composite). A "monolithic composition" includes a blended form.

The term "nitrite" as used herein, alone or in combination, refers to a compound having the general formula R—O—N═O, with R being chosen from H, $M^+$, and an organic moiety. The term also includes salts $M_a(NO_2)_b$ and the anion $NO_2^-$. The term therefore includes compounds such as HONO (nitrous acid), $NaNO_2$ (sodium nitrite), $Ca(NO_2)_2$ (calcium nitrite), and $(CH_3)_2CHCH_2CH_2ONO$ (isoamyl nitrite).

As used herein, the term "phase" is defined as a portion or component of a monolithic structure or composition that is uniformly distributed throughout, to give the structure or composition its monolithic characteristics.

As used herein, the term "three phase" is defined as a monolithic composition or structure comprising three or more phases. An example of a three phase composition according to the disclosure is an entrained polymer formed of a base polymer, active agent, and channeling agent. Optionally, a three phase composition or structure may include an additional phase, e.g., a colorant, but is nonetheless still considered "three phase" on account of the presence of the three primary functional components.

Furthermore, the terms "package," "packaging" and "container" may be used interchangeably herein to indicate a vessel having an enclosure that holds or contains a good, e.g., food product or foodstuffs, a pharmaceutical product or a diagnostic test. Optionally, a package may include a container with a product stored therein. Non-limiting examples of a package, packaging and container include a tray, box, carton, bottle receptacle, vessel, pouch and flexible bag. A pouch or flexible bag may be made from, e.g., polypropylene or polyethylene. The package or container may be closed, covered and/or sealed using a variety of mechanisms including a cover, a lid, a cap, lidding sealant, an adhesive and a heat seal, for example. The package or container is composed or constructed of various materials, such as plastic (e.g., polypropylene or polyethylene), paper, Styrofoam, glass, metal and combinations thereof. In one optional embodiment, the package or container is composed of a rigid or semi-rigid polymer, optionally polypropylene or polyethylene, and optionally has sufficient rigidity to retain its shape under gravity.

The term "container" may refer to a single object capable of holding one or more individual goods, including but not limited to pills, tablets, capsules, caplets, liquids, powders, or any other type of individual objects. Optionally, the container has a single interior space. Optionally, the container is partitioned into interior compartments. Optionally, the container partitioned into interior compartments is a blister package. Optionally, the interior compartments allow for vaporous exchange. Optionally, the individual compartments are isolated from each other. Optionally, the individual objects comprise medicaments, nutritional supplements, herbal supplements, or the like. Optionally, the individual objects occupy individual compartments in the container. Optionally, each of the individual objects is packaged in an individual compartment in the container. Optionally, each of the individual compartments is in vaporous communication with at least one other compartment. Optionally, a single contiguous volume is formed by the combination of the individual compartments and passages for vaporous communication among the individual compartments. Optionally, the headspace of each of the individual compartments is isolated from all other compartments.

The entrained polymer component or active agent can be deposited or dropped into a wide variety of packages and containers having a headspace, such as but not limited to, a blister pack, bottle or the like, that store pharmaceutical products. Optionally, the active agent is in the form of a film sheet, canister, puck or sachet, and is placed or dropped inside of the blister pack or bottle. Optionally, the film sheet is in the form of liner that is positioned inside of a bottle such that the film liner wraps the interior of the bottle. Optionally, the bottle itself, such as a blow-molded bottle (blown bottle), is at least partially composed/made of the active agent. Optionally, if in the form of a vial, the active agent is provided in an entrained polymer composition in the form of an insert or liner in the body or lid of the vial. Optionally, the active agent (in the form of loose particles) is housed inside of a sachet or canister, which is then placed or dropped inside of a blister pack or bottle. Optionally, the sheet or liner includes an extruded, cast or blown film. Optionally, the active agent is in the form of an injection molded component, e.g., puck, made of a polymer composition containing an active agent.

The active agents are generally effective to adsorb, absorb, and/or react with volatile reactive gasses/impurities within a sealed internal headspace of a container or package containing a pharmaceutical dosage form. Each of the active agents is effective to decrease, preclude or eliminate an N-nitroso compound, such as nitrosamine, and/or a nitrosating agent, such as nitrite or $NO_x$, in the headspace of the container or package that stores the pharmaceutical product therein.

Optionally, the active pharmaceutical ingredient of a pharmaceutical dosage form that is described through the presently disclosed methods and materials is chosen from an angiotensin-II-receptor antagonist and a histamine H2 receptor antagonist. Optionally, the active pharmaceutical ingredient is chosen from Losartan, Valsartan, Irbesartan, Candesartan, Olmesartan, Eprosartan, Azilsartan, Telmisartan, Ranitidine, Metformin, Nizatidine, and Pioglitazone.

Optionally, the drug formulations are a blend/granulation of their active pharmaceutical ingredients (API) with various excipients. The excipients may include nitrite impurities at trace levels. Microcrystalline Cellulose (MCC) is a common diluent in oral solid dosage forms, particularly tablets and capsules. These nitrites can form nitrosating species such as nitrous acid and various volatile nitrogen oxides (NOx). For APIs at risk of N-nitroso compound and nitrosating agent formation, the presence of nitrosating species in the excipients used in the drug formulations can directly increase the formation of nitrosamines.

As used herein, the term "scavenging material" is defined as a material that is capable of removing a compound of interest from a volume of gas. Optionally, the removal is accomplished by a noncovalent binding of the compound of interest to the scavenging material. Optionally, the scavenging material is capable of maintaining a decreased concentration of the compound of interest while the compound of interest is introduced to the volume of gas. In certain embodiments, the scavenging material includes an entrained polymer including the active agent, and the compound of interest is nitrites and/or nitrous acid. The scavenging material includes but is not limited to activated carbon ("AC") or its derivatives, such as tris-activated carbon ("T-AC"). The scavenging material can be entrained in at least one base polymer with optional channels throughout.

As used herein, the term "oxygen scavenging material" is defined as an active agent that can decrease the amount of oxygen in a gaseous environment. An oxygen scavenging material can act by any mechanism, including but not limited to chemical reduction (i.e., transfer of one or more electrons from a reducing agent), reductive dissociation of the O—O bond, and coordination of a mono- or dinuclear oxygen species to a metal center.

The term "hydrazine" as used herein, alone or in combination, refers a compound comprising the moiety $R^1R^2$—N—$NR^3R^4$, wherein $R^1$ and $R^2$ are independently chosen from H and substituted or unsubstituted alkyl, cycloalkyl, and aryl. The term "primary hydrazine", as used herein, alone or in combination, refers to a hydrazine for which at least $R^1$ and $R^2$ are H.

The term "hydrazone" as used herein, alone or in combination, refers to a compound comprising the moiety —C═N—$NR^1R^2$, wherein $R^1$ and $R^2$ are independently chosen from H and substituted or unsubstituted alkyl, cycloalkyl, and aryl.

The term "semicarbazone" as used herein, alone or in combination, refers to a compound comprising the moiety —C═O—NH—$NR^1R^2$, wherein $R^1$ and $R^2$ are independently chosen from H and substituted or unsubstituted alkyl, cycloalkyl, and aryl.

The term "N-nitroso", as used herein, alone or in combination, refers to a functional group having the general formula —N—N═O.

The term "N-nitroso compound scavenging", as used herein, alone or in combination, refers to a process whereby a N-nitroso compound, such as nitrosamine, and/or a nitrosating agent, such as nitrite and $NO_x$, is removed from a volume of solid, liquid, or gas. In some embodiments, the scavenging process includes a step of chemical modification, thereby removing the N-nitroso molecule from the molecule. In some embodiments, the chemical modification is chosen from a reduction, an oxidation, a lysis (including hydrolysis), and a condensation. In some embodiments, the scavenging process includes a step of sorption, including but not limited to adsorption to a surface and absorption into a volume, thereby decreasing the amount of free N-nitroso compound in the solid, liquid, or gas.

Without wishing to be bound by a mechanism of action, the scavenging material (e.g., active agent) functions to remove, decrease, scavenge, control or modify the level of the N-nitroso compounds and/or nitrosating agent, e.g., nitrites and/or $NO_x$, in an environment.

Optionally, the scavenging material adorbs or absorbs humidity. In further embodiments, the scavenging material is a desiccant.

The scavenging material may be provided in any form such as: powder, crushed, granular, particulate, pelletized, spherical, or cylindrical form.

Optionally, the scavenging material is provided in one or more scavenging articles. Optionally, each of the one or more scavenging articles is integral with, affixed to or chemically bonded with the interior of the container. Optionally, each of the one or more scavenging articles is incorporated into the walls, lid, cap, or cover of the container. Optionally, each of the individual compartments in a partitioned container is provided with at least one scavenging article.

Exemplary Entrained Polymer Components

Conventionally, desiccants, oxygen absorbers and other active agents have been used in raw form, e.g., as loose particulates housed in sachets or canisters within packaging, to control the internal environment of the package. For many applications, it is not desired to have such loosely stored active substances. Thus, the present application provides compressed components or active entrained polymer components comprising a blended form of a base polymer and active agents, wherein such polymer components can be extruded and/or molded into a variety of desired forms, e.g., container liners, plugs, film sheets, pellets and other such structures.

Optionally, such active entrained polymer components may include channeling agents, such as polyethylene glycol (PEG), which form channels between the surface of the entrained polymer and its interior to transmit a selected material (e.g., moisture) to the entrained active agent (e.g., desiccant to absorb the moisture). As explained above, entrained polymer components may be two phase formulations (i.e., comprising a base polymer and active agent, without a channeling agent) or three phase formulations (i.e., comprising a base polymer, active agent and channeling agent). Entrained polymer components are described, for example, in U.S. Pat. Nos. 5,911,937, 6,080,350, 6,124,006, 6,130,263, 6,194,079, 6,214,255, 6,486,231, 7,005,459, and U.S. Pat. Pub. No. 2016/0039955, each of which is incorporated herein by reference as if fully set forth.

Suitable base polymers for use in the disclosure include thermoplastic polymers, e.g., polyolefins such as polypropylene and polyethylene, polyisoprene, polybutadiene, polybutene, polysiloxane, polycarbonates, polyamides, ethylene-vinyl acetate copolymers, ethylene-methacrylate copolymer, poly(vinyl chloride), polystyrene, polyesters, polyanhydrides, polyacrylianitrile, polysulfones, polyacrylic ester, acrylic, polyurethane and polyacetal, or copolymers or mixtures thereof.

Suitable channeling agents in the disclosure include polyglycol such as polyethylene glycol (PEG), ethylene-vinyl alcohol (EVOH), polyvinyl alcohol (PVOH), glycerin polyamine, polyurethane and polycarboxylic acid including polyacrylic acid or polymethacrylic acid. Alternatively, the channeling agent can be, for example, a water insoluble polymer, such as a polypropylene oxide-monobutyl ether, which is commercially available under the trade name Polyglykol B01/240, produced by CLARIANT. In other embodiments, the channeling agent could be a polypropylene oxide monobutyl ether, which is commercially available under the trade name Polyglykol B01/20, produced by CLARIANT, polypropylene oxide, which is commercially available under the trade name Polyglykol D01/240, produced by CLARIANT, ethylene vinyl acetate, nylon 6, nylon 66, or any combination of the foregoing.

Medicaments

Certain materials, articles of manufacture, and methods are employed for the storage of medicaments susceptible to contamination by an N-nitroso compound. Optionally, the N-nitroso compound is formed during synthesis or processing of the medicament. Optionally, the N-nitroso compound is formed during storage of the medicament in the absence of any preventative measures.

Optionally, the medicament is provided in a solid, liquid, cream or gel form. Optionally, the medicament is provided in granular or powder form. Optionally, the medicament is provided in the form of pills, capsules, caplets, or tablets. Optionally, the pill, capsule, caplet or tablet is provided without an exterior coating. Optionally, a multi-dosage supply of the medicament is packaged in the container. Optionally, a single dosage corresponds to a single pill, capsule, caplet, or tablet. Optionally, a single dosage corresponds to a small number of pills, capsules, caplets, or tablets, for example, 2, 3, or 4 pills, capsules, caplets, or tablets. Optionally, the package comprises a plurality of compartments, the headspace of each of which being isolated from other compartments in the package. Optionally, individual dosages are packaged into each of the single compartments in the package. Optionally, the package allows retrieval of the dosage from an individual compartment without disturbing the remaining compartments that still contain individual dosages.

Entrained Polymer Component Containing Active Agent

Optionally, the active agent is a component of an entrained polymer component, which is at least two phases and comprises the active agent and a base polymer. Optionally, the entrained polymer component is at least three phases and comprises the active agent, a base polymer, and a channeling agent. The entrained polymer component comprises a blended form of the base polymer and active agent and optionally, channeling agent. The structure of the entrained polymer is not limited. Optionally, such entrained polymer components have the structure of a film, a sheet, a liner, a puck, or a plug.

In general, it is believed that the higher the active agent concentration in the mixture, the greater the absorption, adsorption or releasing capacity (as the case may be) will be of the final composition. However, too high an active agent concentration could cause the entrained polymer component to be more brittle, and the molten mixture of active agent, base polymer material and channeling agent to be more difficult to either thermally form, extrude or injection mold.

Optionally, in any embodiment, the loading level or concentration of the active agent can range from 20% to 80%, optionally 30% to 70%, optionally 30% to 60%, optionally 30% to 50%, optionally from 35% to 70%, optionally from 35% to 60%, optionally from 35% to 55%, optionally from 35% to 50%, optionally 40% to 70%, optionally from 40% to 60%, optionally from 40% to 50%, optionally from 45% to 60%, optionally from 50% to 60% by weight with respect to the total weight of the entrained polymer.

Optionally, in any embodiment, the base polymer ranges from 10% to 70%, optionally from 20% to 60%, optionally from 20% to 50%, optionally from 20% to 40%, optionally from 30% to 70%, optionally from 30% to 60%, from 30% to 50%, optionally from 40% to 70%, optionally from 40% to 60%, optionally from 40% to 50% by weight of the total composition.

Optionally, in any embodiment, the channeling agent ranges from 1% to 20%, optionally 1% to 15%, optionally 1% to 10%, optionally 1% to 5%, optionally from 5% to 20%, optionally 5% to 15%, optionally 5% to 10%, optionally from 10% to 20%, optionally from 10% to 15% by weight with respect to the total weight of the entrained polymer.

In one optional embodiment, an entrained polymer may be a three phase formulation including 50% by weight of active agent, 38% by weight ethyl vinyl acetate (EVA) as a base polymer and 12% by weight polyethylene glycol (PEG) as a channeling agent.

Entrained polymer components according to the disclosed concept include base polymer and an active agent dispersed in the base polymer to comprise a blended form. Optionally, the entrained polymer component may also include a polymeric channeling agent. The channeling agent may form interconnecting channels through the entrained polymer component. At least some of the active agent is contained within these channels, such that the channels communicate between the active agent and the exterior of the entrained polymer component via channel openings formed at outer surfaces of the entrained polymer component.

The entrained polymer component may be formed in various ways. For example, the entrained polymer component may be in the form of a plug or puck configured to be deposited in a container. Alternatively, the entrained polymer component is in the form of an extruded film or cast film. Alternatively, the entrained polymer component is in the form of a blown film, as described herein. Alternatively, the entrained polymer component may be in the form of a container insert or integral with the inner wall of a container enclosure, such as a layer of a blow molded bottle (blown bottle).

Interconnecting channels in the entrained polymer component, such as those disclosed herein, may help to facilitate transmission of a desired material, such as volatilized N-nitroso compounds and/or nitrosating agents, such as nitrites and $NO_x$, through the entrained polymer component and to the activated agent thereof dispersed in the base polymer. In other words, the base polymer itself acts as a barrier substance within which an active agent may be entrained. The interconnecting channels formed of the channeling agent provide pathways for the desired material to move through the entrained polymer component.

Optionally, the entrained polymer component may be in the form of an active sheet or film formed used in combination with a barrier sheet to form a composite. The barrier sheet may be a substrate such as foil and/or a polymer with low moisture or oxygen permeability. The barrier sheet is compatible with the entrained polymer structure and is thus configured to thermally bond to the active sheet or film, when the active sheet or film solidifies after extrusion or casting. Optionally, the entrained polymer component is an extruded film that is heat staked to a substrate, such as is disclosed in U.S. Pat. No. 8,142,603, which is incorporated by reference herein in its entirety.

Optionally, the active sheet or film and the barrier sheet are combined to form a packaging wrap having active characteristics at an interior surface formed by the entrained polymer component in the active sheet or film, and vapor resistant characteristics at an exterior surface formed by the barrier sheet. In this embodiment, the active sheet or film occupies a portion of the barrier sheet.

Optionally, multi-layer films are generated by various routes including extrusion, injection molding, vapor deposition, solvent casting, 100% solids cooling, aqueous dispersion, and blow molding. Optionally, the extrusion can be conducted with a single or twin screw extruder. The multilayer films have a morphology comprising of 2-70% activated carbon or a derivative thereof. The rate of reactivity can be controlled through the introduction of various channeling agents and concentrations of the active agent.

Optionally, the entrained polymer component is positioned in a container and substantially all of the interior-facing part of the container is composed of the entrained polymer component. Optionally, the container is fabricated so that the entrained polymer component is located above the level of a product contained in the package, thereby avoiding direct contact between the active agent and the product.

Also provided is an embodiment in which the active agent/scavenging material is not in the form of an entrained polymer component. Optionally, the active agent/scavenging material is provided in a sachet or cannister that is inserted in a package. Optionally, the sachet or cannister contains one or more pores that are sufficiently small to retain the active agent/scavenging material within the sachet or cannister. Optionally, the sachet or cannister is included in the package so as to be located above the level of the product contained in the package, thereby avoiding direct contact between the active agent/scavenging material (e.g., the sachet or cannister) and the product.

Blown Films

In one optional aspect, there is provided herein a blown film material comprising a base polymer and an active agent, and optionally a channeling agent. The active agent includes a scavenging material.

Optionally, the base polymer is chosen from a polyolefin, a polyamide, and a polyester. Optionally, the base polymer is chosen from a polyolefin and a polyester. Optionally, the base polymer is chosen from polyethylene, polypropylene, a polyethylene/polypropylene copolymer, and poly(lactic acid).

In some embodiments, the base polymer is a thermoplastic. In some embodiments, the base polymer is a thermoplastic elastomer. In some embodiments, the thermoplastic elastomer is a thermoplastic polyamide elastomer. In some embodiments, the thermoplastic elastomer is a thermoplastic polyester elastomer. In some embodiments, the thermoplastic elastomer is a thermoplastic polyolefin elastomer. In some embodiments, the thermoplastic elastomer is a thermoplastic polystyrene elastomer. In some embodiments, the thermoplastic elastomer is a thermoplastic polyurethane elastomer. In some embodiments, the thermoplastic elastomer is a thermoplastic elastomer vulcanizate. In some embodiments, the thermoplastic elastomer is an unclassified thermoplastic polyamide elastomer. In some embodiments, the thermoplastic elastomer is a block copolymer. In some embodiments, the base polymer is a block copolymer. In some embodiments, the block copolymer comprises polyester segments and polyether segments. In some embodiments, the polyester segment is poly(alkylene terephthalate). In some embodiments, the polyester segment is poly(butylene terephthalate). In some embodiments, the polyether segment is a poly(alkylene glycol). In some embodiments, the polyether segment is chosen from polyethylene glycol, polypropylene glycol, and polytetramethylene glycol. In some embodiments, the polyether segment is one or more long chain glycols. In some embodiments, the block copolymer includes a hard crystalline segment and a soft amorphous segment. In some embodiments, the block copolymer exhibits high thermal stability.

In some embodiments, the base polymer is HYTREL®, a thermoplastic polyester elastomer from DuPont. HYTREL® is a block copolymer, consisting of segments of polybutylene terephthalate and segments of polyether. In some embodiments, the base polymer is HYTREL® 7246.

In some embodiments, the base polymer has the formula $(\text{—CHR—X—})_n$ with —X— chosen from $\text{—CH}_2\text{—}$, —COO—, and —CONH—, and R chosen from H and $C_{1-10}$alkyl.

In some embodiments, the base polymer has a formula chosen from $(\text{—CHRCH}_2\text{—})_n$ and $(\text{—CHRCOO—})_n$, with R chosen from H and $C_{1-10}$alkyl. In some embodiments, R is chosen from H, $CH_3$, $C_2H_5$, $C_4H_9$, $C_6H_{13}$, and $C_8H_{17}$. In some embodiments, R is chosen from $C_2H_5$, $C_4H_9$, and $C_6H_{13}$.

Optionally, the base polymer comprises an ethylene/alpha-olefin copolymer. In some further embodiments, the alpha-olefin is chosen from propylene, 1-butene, 1-pentene; 1-pentene with one or more methyl, ethyl, or propyl substituents; 1-hexene; 1-hexene with one or more methyl, ethyl, or propyl substituents; 1-heptene; 1-heptene with one or more methyl, ethyl, or propyl substituents; 1-octene; 1-octene with one or more methyl, ethyl, or propyl substituents; 1-nonene; 1-nonene with one or more methyl, ethyl, or propyl substituents; ethyl, methyl, or dimethyl-substituted 1-decene; 1-dodecene; and styrene. In some further embodiments, the alpha-olefin is chosen from propylene, 1-butene, 1-pentene, 1-hexene, 1-heptene, 1-octene, 1-nonene, 1-decene, and 1-dodecene.

Optionally, the base polymer comprises two block copolymers. In some further embodiments, one of the two block copolymers is an ethylene/alpha-olefin copolymer as disclosed herein. In some further embodiments, the base polymer comprises EXACT™ 3040. In some further embodiments, one of the two block copolymers is a block copolymer that contains both a block of ester monomers and a block of polyether glycols as disclosed herein. In some further embodiments, the base polymer comprises HYTREL® 7246. In some further embodiments, the base polymer comprises both EXACT™ 3040 and HYTREL® 7246. In some further embodiments, the base polymer consists of a mixture of EXACT™ 3040 and HYTREL® 7246.

Optionally, the base polymer comprises both a polyolefin and a polyester. Optionally, the polyolefin ranges from 10% and 40% by weight of the total composition, optionally between 15% and 30%. Optionally, the polyester ranges from 20% and 80% by weight of the total composition, optionally between 25% and 70%, optionally 30% and 60%.

In some embodiments, the oxygen scavenging material comprises a chemical reducing agent. In some embodiments, the chemical reducing agent is a 1- or 2-electron reducing agent. In some embodiments, the chemical reducing agent produces hydrogen peroxide ($H_2O_2$) or water from the reduction of oxygen. In some embodiments, the oxygen scavenging material comprises a neutral metal. In some embodiments, the oxygen scavenging material comprises a low-valent metal ion, including but not limited to $Fe^{2+}$, $Sn^{2+}$, and $Ti^{3+}$. In some embodiments, the neutral metal is in monolithic, granulated, or powdered form. In some embodiments, the oxygen scavenging material is a naturally occurring antioxidant. In some embodiments, the oxygen scavenging material comprises a vicinal diol (RC(OH)═C(OH)R') or keto equivalent. In some embodiments, the oxygen scavenging material provides a vicinal diketone (RC(═O)—C(═O)—R') from the reduction of oxygen. In some embodiments, the oxygen scavenging material is chosen from a polyolefin, a phenol, a hydroquinone, and a porphyrin. In some embodiments, the oxygen scavenging material comprises an organic sulfur-containing compound, including but not limited to a thioether, a thiolester, and a thiol. In some embodiments, the oxygen scavenging material comprises an organic phosphorus-containing compound, including but not limited to a phosphine and a phosphite. In some embodiments, the oxygen scavenging material further comprises a catalyst. In some embodiments, the oxygen scavenging material further comprises a pH-buffering material.

In some embodiments, the oxygen scavenging material comprises a polyene. In some embodiments, the oxygen scavenging material comprises a conjugated polyene, optionally comprising 2, 3, 4, 5, 6, 7, 8, 9, 10, 11, or 12 olefins in conjugation. In some embodiments, the oxygen scavenging material comprises a compound chosen from retinol, retinal, and carotene. In some embodiments, the oxygen scavenging material comprises a compound chosen from a porphyrin and a heme.

In certain embodiments, the oxygen scavenging material is a free radical trap. Without wishing to be bound by theory, certain free radical traps can decrease the amount of reactive oxygen species ("ROS"), either by decreasing their rate of formation, or removing them from the medium. Some free radical traps transfer a hydrogen to a radical species. Certain free radical traps contain phenol moieties, such as BHA, BHT, caffeic acid, ferulic acid, and α-tocopherol. Certain free radical traps are enols, such as ascorbic acid (Vitamin C). Certain free radical traps contain a weak X—H bond (X═N, O, S), including but not limited to thiols, uric acid, and bilirubin. Certain free radical traps contain polyene moieties, such as β-carotene and other carotenoids. Certain free radical traps contain conjugated or nonconjugated dienes, such as α-terpinene and γ-terpinene, respectively, as well as certain unsaturated fats and fatty acids.

In some embodiments, the oxygen scavenging material comprises L-ascorbic acid, which is the 4R, 5S isomer of 3,4,5,6-tetrahydroxy-2-oxohexanoic acid. L-ascorbic acid can exist as (open) acid and (closed) lactone forms. The parent acid, 3,4,5,6-tetrahydroxy-2-oxohexanoic acid, has three chiral centers, at the carbons labelled 3, 4, and 5, following organic chemical nomenclature, in the acid structure of Equation (1) as shown below. Of the three chiral centers, C3 is readily epimerized due to the adjacent ketone. In contrast, C4 and C5 both represent non-interconverting stereocenters, giving rise to a total four isolable stereoisomers, each of which potentially existing in equilibrium with the lactone form, as shown in Equation (II), below

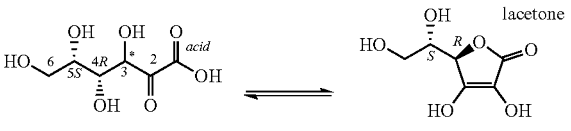

(I)

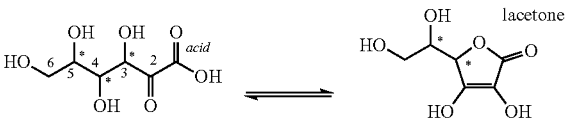

(II)

Of the four isolable stereoisomers, D-ascorbic acid is the enantiomer of L-ascorbic acid. The other two isomers are D-isoascorbic acid, the 5R epimer of ascorbic acid, as well as its enantiomer, L-isoascorbic acid. A person of skill will appreciate that each of the four stereoisomers will be expected to behave similarly as reducing agents and/or radical traps. All possible mixtures of the four enantiomers are contemplated with this disclosure, including isolated enantiomers of either ascorbic acid or isoascorbic acid or mixtures thereof, D/L racemic mixtures either ascorbic acid or isoascorbic acid or mixtures thereof, and intermediate compositions of either ascorbic acid or isoascorbic acid having arbitrary enantiomeric excess, and mixtures thereof.

Any of the four stereoisomers may be provided as any one of the carboxylic acid, a salt of the carboxylic acid, an ester, or a lactone, or mixtures thereof. No limitation is envisaged on the type of ester; suitable esters may include alkyl esters, $C_1$-$C_8$ alkyl esters, methyl esters, ethyl esters, isopropyl esters, and t-butyl esters. The choice of ester may be determined by ease of hydrolysis to the acid, compliance of the alcohol product (e.g., methanol, ethanol) with regulations and best practices for the particular application, and desired water or lipid solubility.

In some embodiments, the activity of ascorbic acid as a reducing agent can be modulated by adjusting the pH of the environment. Ascorbic acid is a dibasic acid with $pK_{a1}$=4.1 and $pK_{a2}$=11.8; suitable choice of acids, bases, or buffers can vary the relative amounts of the neutral acid, the monoanion, and the dianion, each of which has different rates of reaction. Furthermore, inclusion of catalytically active metals, including but not limited to salts of nickel, cobalt, iron, copper, and manganese or, in some embodiments, Fe(III) or Cu(II), can be expected to change the rate of reaction. Alternatively, the inclusion of metal ion scavengers, such as EDTA, can be expected to change the rate of reaction. By either of these strategies, the potency of ascorbic acid over time can be adjusted so as to meet particular requirements. Alternatively, controlled hydrolysis of an ascorbic acid ester may provide a pathway for controlling the potency of ascorbic acid over time.

In some embodiments, the oxygen scavenging material comprises a partially unsaturated derivative of polyethylene. In some embodiments, the oxygen scavenging material comprises polyethylene interspersed with —($CHR^1$═$CHR^2$)— units, wherein $R^1$ and $R^2$ are each independently a hydrogen atom, an alkyl group that is optionally substituted, an aryl group that is optionally substituted, an alkylaryl group that is optionally substituted, —$COOR^3$, —$OCOR^4$, a cyano group or a halogen atom, and $R^3$ and $R^4$ are each independently a hydrogen atom or an alkyl group having 1 to 10 carbon atoms. In some embodiments, neighboring —($CHR^1$═$CHR^2$)— units are separated by three or more methylene (—$CH_2$—) units.

In some embodiments, the oxygen scavenging material is a material disclosed in U.S. Pat. No. 7,893,145, incorporated herein by reference in its entirety. In some embodiments, the oxygen scavenging material has a structural unit represented by Formula (III):

(III)

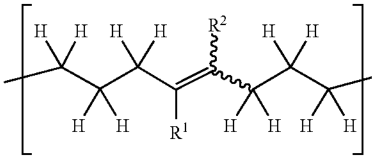

wherein: $R^1$ and $R^2$ are each independently a hydrogen atom, an alkyl group that is optionally substituted, an aryl group that is optionally substituted, an alkylaryl group that is optionally substituted, $COOR^3$, $OCOR^4$, a cyano group or a halogen atom, and $R^3$ and $R^4$ are each independently a hydrogen atom or an alkyl group having 1 to 10 carbon atoms. In some embodiments, $R^1$ and $R^2$ are independently chosen from H and $C_{1-6}$alkyl.

In some embodiments, the oxygen scavenging material is a ring-opening metathesis polymer of a cyclic olefin having 7 or more carbon atoms. In some embodiments, the oxygen scavenging material is a ring-opening metathesis polymer of a substituted or unsubstituted cyclooctene. In some embodiment, the average molecular weight of the polymer is 1000 amu or less.

In some embodiments, the polymer-based oxygen scavenging material further comprises a transition metal salt chosen from an iron salt, a nickel salt, a copper salt, a manganese salt and a cobalt salt. Optionally, the transition metal salt is chosen from cobalt alkanoate or cobalt(II) stearate.

In some embodiments, the polymer-based oxygen scavenging material further comprises a compound chosen from $TiO_2$, $V_2O_5$, $MoO_3$, $CrO_3$, $WO_3$, $WO_2$, $WCl_2O_2$, and $WOCl_4$. Optionally, the polymer-based oxygen scavenging material further comprises $WO_3$.

In any embodiment, the active agent is preferably a particulate, granular and/or mineral-based material and is optionally present in at least 35% to 70%, optionally from 40% to 60%, optionally from 45% to 55% by weight with respect to the total weight of the entrained polymer.

In some embodiments, the blown film entrained polymer further comprises a channeling agent. In some embodiments, the channeling agent is chosen from a polyglycol such as polyethylene glycol (PEG), ethylene-vinyl alcohol (EVOH), polyvinyl alcohol (PVOH), glycerin polyamine, polyurethane and polycarboxylic acid including polyacrylic acid or polymethacrylic acid.

In some embodiments, the channeling agent is a water insoluble polymer, such as a propylene oxide polymerisate-monobutyl ether, such as Polyglykol B01/240, produced by CLARIANT. In other embodiments, the channeling agent could be a propylene oxide polymerisate monobutyl ether, such as Polyglykol B01/20, produced by CLARIANT, propylene oxide polymerisate, such as Polyglykol D01/240, produced by CLARIANT, ethylene vinyl acetate (EVA), nylon 6, nylon 66, or any combination of the foregoing.

Also provided is a method of manufacture for a blown film material as disclosed herein, the method comprising the steps of: extruding a suitable precursor material (e.g., molten mix of a polymer and the active agent/scavenging material) in a screw extruder with warming; passing the warmed material through a tubular die; expanding and stretching the warmed material with positive pressure; and allowing the expanded and stretched material to cool.

Optionally, the extrusion is performed at a temperature between 140° C. and 190° C., optionally between 145° C. and 175° C., optionally between 150° C. and 170° C., optionally between 150° C. and 165° C. As used herein, the term "between" includes the endpoints of a stated numerical range.

Optionally, the extrusion is performed with a rotation speed of 5 rpm or greater, optionally 10 rpm or greater, optionally 15 rpm or greater, optionally 25 rpm or greater, optionally 35 rpm or greater, optionally 45 rpm or greater, optionally 55 rpm or greater.

Optionally, the extrusion is performed with a rotation speed of 65 rpm or less, optionally 55 rpm or less, optionally 45 rpm or less, optionally 35 rpm or less, optionally 30 rpm or less, optionally 25 rpm or less, optionally 20 rpm or less.

Optionally, the extrusion is performed with a rotation speed of between 10 rpm and 75 rpm, optionally between 15 rpm and 65 rpm, optionally between 15 rpm and 60 rpm, optionally between 20 rpm and 50 rpm.

Optionally, the extrusion is performed with a rotation speed of between 5 rpm and 35 rpm, optionally between 10 rpm and 30 rpm, optionally between 10 rpm and 25 rpm, optionally between 10 rpm and 20 rpm.

Optionally, the tensile strength of the blown film material is significantly greater than that of a comparable cast extruded film material.

Optionally, the dart impact resistance of the blown film material is significantly greater than that of a comparable cast extruded film material.

Optionally, the transparency of the blown film material is significantly greater than that of a comparable cast extruded film material.

Optionally, the haze of the blown film material is significantly greater than that of a comparable cast extruded film material.

Optionally, the brittleness of the blown film material is significantly less than that of a comparable cast extruded film material.

Optionally, the density of the blown film material is significantly greater than that of a comparable cast extruded film material. Optionally, the density of the blown film material is significantly less than that of a comparable cast extruded film material.

Optionally, the tensile strength of the blown film material in the machine and/or direction is significantly greater than that of a comparable cast extruded film material.

Optionally, the elongation of the blown film material in the machine and/or direction is significantly greater than that of a comparable cast extruded film material.

Optionally, the Young's modulus of the blown film material in the machine and/or direction is significantly greater than that of a comparable cast extruded film material.

A representative process for forming blown film material is depicted in FIG. 1. A precursor resin, in the form of pellets, is fed into hopper 105 where screw 110 rotates and forces the material forward while heat is applied, gradually forming a melt. The molten material 115 then flows through die 120, resulting in a hollow tube of material. Bubble 125 is formed in the material by introduction of air via a hole in the center of the die. The material progresses upward around the bubble, is cooled, and eventually is allowed to collapse through the action of collapsing frame 130. Throughout this step, nip rolls 135 pull the material upward and maintain proper tension. The collapsed material passes through a series of rollers, including edge trim 140, and is eventually taken up on winder 145.

Due to the nature of the blown film process, certain physical characteristics of the resulting film material may be significantly different than for films manufactured using other techniques, for example cast film extrusion. For example, a cast film process can produce a film with low and/or nonuniform orientation of the polymer strands within the material. In contrast, a blown film material may be highly oriented, with orientation uniform across the cylindrical bubble.

In turn, orientation of the polymer strands within the material can influence the degree of crystallinity, which can affect properties such as clarity/haze, tear strength and elongation, puncture resistance, and toughness.

Mechanical properties in a blown film can be significantly different than those for a cast film. In the blown film process, the material is drawn in both the transverse and machine directions. In contrast, tentered films can have nonuniform strengths in these two directions.

Optionally, in any embodiment, the aforementioned extrusion process includes coextrusion of two or more layers wherein at least one such layer is the active layer (mixture of polymer and active agent) and at least another such layer is a polymer material without an active agent incorporated therein. In such embodiments, what may be formed is a multilayer composite in which at least one layer is an active entrained polymer layer.

Blister Packages

Blister packages or blister packs according to optional embodiments of the disclosed concept may have structures similar to any one of those described in U.S. Pat. No. 6,279,736 (Hekal), International Publication No. WO 2020/146556 (Hollinger), and International Publication No. WO 2022/236313 (Hollinger), each of which is incorporated herein by reference in its entirety. Blister packs described in the aforementioned disclosures may include a backing and a cover secured thereto that forms one or more blister cavities. Those blister packs also include an active member, for example, in the form of an active entrained polymer film that is provided within each blister cavity. Such active film in the prior art may have included desiccant, for example, molecular sieve. Blister packs in the prior art and according to the disclosed concept may include a single blister or a plurality of blisters, e.g., greater or fewer than four blisters per blister card.

In an optional aspect of the disclosed concept, the container is a blister pack. Optionally, the blister pack comprises an active agent. The active agent is capable to decrease, mitigate, remove or preclude the formation of an amount of nitrosating agent and/or N-nitroso compound in a headspace within a respective blister cavity and/or in the pharmaceutical dosage form. In addition or as an alternative, the active agent is capable to scavenge an N-nitroso compound from the headspace and/or in the pharmaceutical dosage form.

Figure 2:
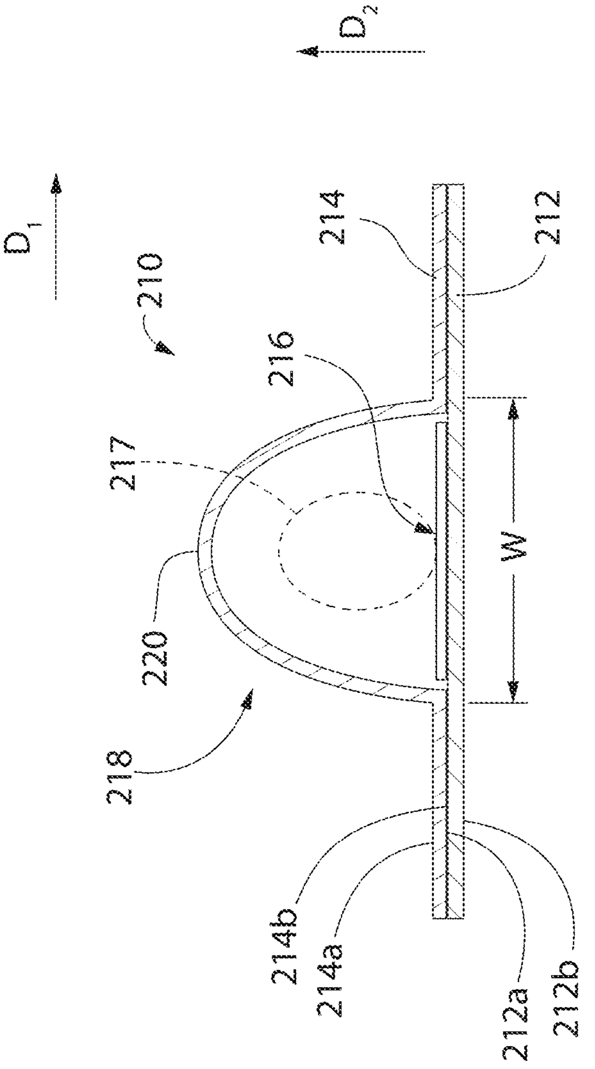
FIG. 2 is a schematic illustration of a blister pack for storing a medicament according to an optional embodiment of the disclosed concept.

A section view of a single blister of a non-limiting exemplary blister pack 210 (which optionally has a plurality of blisters) is shown in FIG. 2. The blister pack 210 includes a backing 212 and a cover 214 that is attached to the backing 212. Further, the cover 214 is attached to the backing 212 such that at least one cavity or enclosure is formed therebetween or a plurality of spaced-apart cavities/enclosures are formed by the combined cover 214 and backing 212. As a result, the cover 214 and the backing 212 form at least one enclosure that is structured and/or configured to store at least one product 217. Optionally, the cover 214 can have any of a variety of shapes and/or configurations, such as disclosed in WO 2020/146556.

The backing 212 can have a first side or surface 212*a* and an opposing second side or surface 212*b*. Optionally, at least the first side 212*a* of the backing 212 may be flat or planar. In one embodiment, each of the first and second sides 212*a*, 212*b* of the backing 212 are flat or planar, such that each of the first and second sides 212*a*, 212*b* extends in a plane, which are at least slightly spaced-apart.

The cover 214 can have a first side or surface 214*a* and an opposing second side or surface 214*b*. Optionally, at least a portion of the first and second sides 214*a*, 214*b* of the cover 214 are flat or planar. At least a portion of the second side 214*b* of the cover 214 can optionally be attached or adhered, such as by heat staking, thermoforming or cold forming, to the first side 212*a* of the backing 212 to form a sealed package for containing product(s). The cover 214 can have the same or a different thickness (as measured in the direction of $D_2$) as the backing 212. In one embodiment, the cover 214 is made or formed of a formable web. In one embodiment, the formable web is made from a thermoplastic material, such as a thermoformed film.

The cover 214 includes or is formed to have at least one blister, generally designated 218. For example, the cover 214 can include two or more spaced-apart blisters 218. The cover 214 can have more or fewer blisters and one or more of the blisters can have a different size and/or shape than another one of the blisters 218 of the blister pack 210, depending upon the particular need. Optionally, each blister 218 can have at least a partial egg shape or a bulbous shape. Alternatively, in one embodiment, each blister 218 can have at least a partial plateau shape (e.g., when viewed from the side) or a cylindrical shape. When the cover 214 is attached to the backing 212, a sealed cavity or enclosure is formed within or by each blister 218.

The blister pack 210 can enclose one or more products 217 (shown schematically in FIG. 2), such as a pharmaceutical oral solid dosage form, vitamins or other nutritional supplements, foodstuff, small consumer goods, probiotics, etc. Such products may be in the form of pills, e.g., tablets, capsules, and the like.

The active agent is provided in the enclosure formed by each blister 218. For example, the active agent may be provided in an entrained polymer film 216 (e.g., extruded film) deposited within the enclosure. Optionally, the entrained polymer film is adhered to a portion of the inner wall of the enclosure e.g., adhered to the first side 212*a* of the backing 212. With this configuration, the active agent is effective to decrease, mitigate, remove or preclude the formation of an amount of nitrosating agent and/or N-nitroso compound in the at least one enclosure and/or in the pharmaceutical dosage form.

Bottles or Vials

Optionally, a container in accordance with the disclosed concept may be in the form of a bottle or vial. The bottle or vial may include a plurality of pharmaceutical or other products (e.g., in the form of pills, tablets, capsules, caplets, or the like) stored within a product compartment of the bottle or vial. The bottle or vial may include a polymer puck, insert or liner secured to or integral with the bottle or vial, the puck, insert or liner including an active agent, e.g., oxygen scavenger, (according to any embodiments disclosed herein) dispersed within it. Alternatively, the active agent may be provided in a stand-alone component (e.g., sachet or canister) that is optionally loosely dropped into the container. Optionally, the active agent is an oxygen scavenging material. Optionally, the active agent is ascorbic acid.

Optionally, the active agent is incorporated into a puck that is made from an entrained polymer composition comprising a base polymer into which the active agent, preferably in granular, particulate or powdered form, is dispersed. The puck is thus one form of entrained polymer component according to an optional aspect of the disclosed concept. As used herein, a "puck" is a three-dimensional shaped article made from the entrained polymer, which has sufficient thickness and rigidity to retain its shape under gravity. Optionally, the puck may be in a standard or traditional three-dimensional geometric shape, such as a sphere, ovaloid, cylinder, or rectangular cuboid, for example. Alternatively, the puck may be of non-symmetrical, less traditional or complex geometry. Optionally, the puck has a minimum cross sectional material thickness of 1 mm or greater, optionally 1.5 mm or greater, optionally 2 mm or greater, optionally from 2 mm to 10 mm. Optionally, the puck has outer dimensions (including thickness of the part and, if applicable, space between solid portions) of at least 2 mm (L) by 2 mm (W) by 2 mm (H). Optionally, the puck has a length of at least 2 mm and a width and height that are each longer than 2 mm, optionally at least 2.5 mm, optionally at least 3 mm, optionally from 2.5 mm to 50 mm. The puck is preferably formed by injection molding.

Optionally, the puck is provided in a shape and size consistent with standard desiccant canister sizes in the pharmaceutical industry. Desiccant canisters are rigid drop-in components that are used to scavenge moisture or other gases or volatiles that impact drug stability and shelf-life. They typically include a polymer shell with loose active materials, e.g. silica gel beads, stored in an empty space within the shell. Canisters are typically configured for high-speed automated insertion into packages using standard packaging equipment. Thus, according to an optional aspect of the disclosed concept, the entrained polymer component may be provided in the shape and size of a standard desiccant canister. Optionally, the canister-shaped entrained polymer component is in the shape of a cylinder. Optionally, the cylindrical canister-shaped entrained polymer component has a height of 5 to 20 mm, optionally 14 to 20 mm and a diameter of 10 to 30 mm, optionally 18 to 25 mm. Optionally, the component has the height and diameter dimensions of an industry standard 0.5 g size desiccant canister, 1 g size desiccant canister, 2 g size desiccant canister or 3 g size desiccant canister. Optionally, an industry standard 0.5 g size desiccant canister has a height of 7 mm and diameter of 16 mm. Optionally, an industry standard 1 g size desiccant canister has a height of 18 mm and diameter of 13-14 mm. Optionally, an industry standard 2 g size desiccant canister has a height of 21 mm and diameter of 18 mm. Optionally, an industry standard 3 g size desiccant canister has a height of 25 mm and diameter of 19 mm. Optionally, the component has a height of about 7 mm and a diameter of about 16 mm, or a height of about 18 mm and a diameter of about 13-14 mm, or a height of about 16 mm and a diameter of about 19 mm, or a height of about 21 mm and a diameter of about 18 mm, or a height of about 25 mm and a diameter of about 19 mm. Providing the entrained polymer component in the form of a cylindrical puck having dimensions of standard industry canisters would enable the disclosed technology to be utilized as a drop-in solution for bottled medications. The puck could thus be inserted into bottles on a bottling line using standard high-speed automated filling equipment.

Optionally the bottle or vial is produced by a blow molding process. The blown bottle or vial includes a base, a sidewall extending from the base, wherein the base and sidewall define an interior configured to house at least one pharmaceutical dosage form. The blown bottle or vial can also include a lid coupled to an open top portion to enclose the pharmaceutical dosage form within the interior. The side wall generally includes a barrier layer and an active agent layer that are blow molded together, with the barrier layer being located external relative to the active agent layer. The barrier layer is made of any suitable plastic material. The active agent layer may be a monolithic composition including a mixture of a base polymer, active agent, and channeling agent. Optionally, in any embodiment, the bottle may have a total wall thickness of from 10 to 80 mils, optionally from 20 to 60 mils, optionally from 20 to 40 mils. The bottle may be thicker than 80 mils for some applications. In one optional embodiment, the bottle includes a 20-40 mil thick wall and/or a 20-40 mil thick active agent layer. In another optional embodiment, the bottle includes a 20 mil barrier layer and a 20 mil active agent entrained polymer layer. The barrier layer material is not particularly limited. For example, HDPE, LDPE, PE or any non-moisture permeable material may be used.

Optionally, in addition to the barrier and active agent layers, the sidewall further includes a relatively thin skin layer attached to the active agent layer. The barrier layer, the active agent layer and the skin layer are each blow molded together (from a coextruded composite material); the active agent layer and the barrier layer are each respectively located external relative to the skin layer. In one embodiment, the skin layer is made of a plastic material, optionally a low density polyethylene material. Optionally, the skin layer has a thickness from 0.005 to 0.1 mm, or from 0.005 mm to 0.05 mm, or about 0.01 mm.

Optionally, in addition to the barrier layer, the active agent layer, and the skin layer, the side wall further has an intermediate layer located between the barrier layer and the active agent layer. Optionally, the intermediate layer is made of a monolithic composition including a plastic material and a mixture of a base polymer, an active agent, and a channeling agent. It will be appreciated that a method of manufacturing the bottle or vial includes the steps of providing a stock component, inserting an apparatus into an opening in the stock component, and passing air into the opening of the stock component in order to form the bottle or vial. Blow molded bottles with active agent layers and methods for making the same are disclosed in U.S. Pat. App. Pub. No. 2021/0245413, which is incorporated herein by reference in its entirety. It is contemplated that the disclosed concept can utilize methods of making blow molded bottles as taught in the aforementioned published patent application, except that the active agents used in the active layer could be any one or more of the active agents described herein.

Inert Atmosphere Packaging

Certain methods disclosed herein provide containers, including blister packages, for packaging of dosage forms, and related methods. In some embodiments, an inert gas is introduced into the container, thereby partially or completely replacing the ambient air within the headspace with the inert gas. The inert gas can be nitrogen or a noble gas such as argon. Introduction of the inert gas can be carried out before, during, or after introduction of the dosage form within the package. It will be understood that partial or complete replacement of ambient air can have the effect of decreasing moisture and/or oxygen within the headspace, thereby reducing the potential or degree of hydrolysis or oxidation reactions, respectively. It will further be understood that partial or complete replacement of ambient air during or after introduction of the dosage form, can have the effect of decreasing the amount of volatile N-nitroso compound and/or nitrosating agent that was released into the headspace from the dosage form.

EXEMPLARY EMBODIMENTS

The following exemplary embodiments further describe optional aspects of the presently disclosed technology and are part of this Detailed Description. These exemplary embodiments are set forth in a format substantially akin to claims (each with numerical designations followed by a capital letter), although they are not technically claims of the present application. The following exemplary embodiments refer to each other in dependent relationships as "embodiments" instead of "claims."

Methods and Systems for Decreasing/Mitigating/Removing/Precluding N-Nitroso Compounds 1A. A method of decreasing, mitigating, removing or precluding formation of an amount of nitrosating agent and/or an N-nitroso compound in an enclosure of a pharmaceutical drug package to inhibit a potential adverse health effect on a patient associated with the nitrosating agent or N-nitroso compound, the method comprising:

providing at least one pharmaceutical dosage form in the enclosure of the pharmaceutical drug package, thereby forming a headspace in the enclosure in a portion of the enclosure not occupied by the at least one pharmaceutical dosage form, the at least one pharmaceutical dosage form having in it, on it, or having a propensity to form, emit, or react with the nitrosating agent and/or N-nitroso compound that is associated with the potential adverse health effect on the patient; and providing an entrained polymer component within the headspace, the entrained polymer component comprising a blended form of a base polymer and an ascorbic acid active agent;

wherein the entrained polymer component is effective to decrease, mitigate, remove or preclude the formation of the amount of nitrosating agent and/or N-nitroso compound in the headspace and/or in the at least one pharmaceutical dosage form, thereby inhibiting the potential adverse health effect on the patient associated with the nitrosating agent or N-nitroso compound.

1B. A method of decreasing, mitigating, removing or precluding formation of an amount of nitrosating agent and/or an N-nitroso compound in an enclosure of a pharmaceutical drug package to inhibit a potential adverse health effect on a patient associated with the nitrosating agent or N-nitroso compound, the method comprising:

providing at least one pharmaceutical dosage form in the enclosure of the pharmaceutical drug package, thereby forming a headspace in the enclosure in a portion of the enclosure not occupied by the at least one pharmaceutical dosage form, the at least one pharmaceutical dosage form having in it, on it, or having a propensity to form, emit, or react with the nitrosating agent and/or N-nitroso compound that is associated with the potential adverse health effect on the patient; and providing an entrained polymer component within the headspace, the entrained polymer component comprising a blended form of a base polymer and a sodium chloride active agent, optionally wherein the entrained polymer component is free from or substantially free from a metallic material, optionally wherein the metallic material is iron;

wherein the entrained polymer component is effective to decrease, mitigate, remove or preclude the formation of the amount of nitrosating agent and/or N-nitroso compound in the headspace and/or in the at least one pharmaceutical dosage form, thereby inhibiting the potential adverse health effect on the patient associated with the nitrosating agent or N-nitroso compound.

1C. A method of decreasing, mitigating, removing or precluding formation of an amount of nitrosating agent and/or an N-nitroso compound in an enclosure of a pharmaceutical drug package to inhibit a potential adverse health effect on a patient associated with the nitrosating agent or N-nitroso compound, the method comprising:

providing at least one pharmaceutical dosage form in the enclosure of the pharmaceutical drug package, thereby forming a headspace in the enclosure in a portion of the enclosure not occupied by the at least one pharmaceutical dosage form, the at least one pharmaceutical dosage form having in it, on it, or having a propensity to form, emit, or react with the nitrosating agent and/or N-nitroso compound that is associated with the potential adverse health effect on the patient; and providing an entrained polymer component within the headspace, the entrained polymer component comprising a blended form of a base polymer and a sodium bicarbonate active agent;

wherein the entrained polymer component is effective to decrease, mitigate, remove or preclude the formation of the amount of nitrosating agent and/or N-nitroso compound in the headspace and/or in the at least one pharmaceutical dosage form, thereby inhibiting the potential adverse health effect on the patient associated with the nitrosating agent or N-nitroso compound.

1D. A method of decreasing, mitigating, removing or precluding formation of an amount of nitrosating agent and/or an N-nitroso compound in an enclosure of a pharmaceutical drug package to inhibit a potential adverse health effect on a patient associated with the nitrosating agent or N-nitroso compound, the method comprising:

providing at least one pharmaceutical dosage form in the enclosure of the pharmaceutical drug package, thereby forming a headspace in the enclosure in a portion of the enclosure not occupied by the at least one pharmaceutical dosage form, the at least one pharmaceutical dosage form having in it, on it, or having a propensity to form, emit, or react with the nitrosating agent and/or N-nitroso compound that is associated with the potential adverse health effect on the patient; and providing an entrained polymer component within the headspace, the entrained polymer component comprising a blended form of a base polymer and a vitamin E active agent;

wherein the entrained polymer component is effective to decrease, mitigate, remove or preclude the formation of the amount of nitrosating agent and/or N-nitroso compound in the headspace and/or in the at least one pharmaceutical dosage form, thereby inhibiting the potential adverse health effect on the patient associated with the nitrosating agent or N-nitroso compound.

1E. A method of decreasing, mitigating, removing or precluding formation of an amount of nitrosating agent and/or an N-nitroso compound in an enclosure of a pharmaceutical drug package to inhibit a potential adverse health effect on a patient associated with the nitrosating agent or N-nitroso compound, the method comprising:

providing at least one pharmaceutical dosage form in the enclosure of the pharmaceutical drug package, thereby forming a headspace in the enclosure in a portion of the enclosure not occupied by the at least one pharmaceutical dosage form, the at least one pharmaceutical dosage form having in it, on it, or having a propensity to form, emit, or react with the nitrosating agent and/or N-nitroso compound that is associated with the potential adverse health effect on the patient; and providing an entrained polymer component within the headspace, the entrained polymer component comprising a blended form of a base polymer and a calcium carbonate active agent;

wherein the entrained polymer component is effective to decrease, mitigate, remove or preclude the formation of the amount of nitrosating agent and/or N-nitroso compound in the headspace and/or in the at least one pharmaceutical dosage form, thereby inhibiting the potential adverse health effect on the patient associated with the nitrosating agent or N-nitroso compound.

1F. A method of decreasing, mitigating, removing or precluding formation of an amount of nitrosating agent and/or an N-nitroso compound in an enclosure of a pharmaceutical drug package to inhibit a potential adverse health effect on a patient associated with the nitrosating agent or N-nitroso compound, the method comprising:

providing at least one pharmaceutical dosage form in the enclosure of the pharmaceutical drug package, thereby forming a headspace in the enclosure in a portion of the enclosure not occupied by the at least one pharmaceutical dosage form, the at least one pharmaceutical dosage form having in it, on it, or having a propensity to form, emit, or react with the nitrosating agent and/or N-nitroso compound that is associated with the potential adverse health effect on the patient; and providing an entrained polymer component within the headspace, the entrained polymer component comprising a blended form of a base polymer and a magnesium carbonate active agent;

wherein the entrained polymer component is effective to decrease, mitigate, remove or preclude the formation of the amount of nitrosating agent and/or N-nitroso compound in the headspace and/or in the at least one pharmaceutical dosage form, thereby inhibiting the potential adverse health effect on the patient associated with the nitrosating agent or N-nitroso compound.

1G. A method of decreasing, mitigating, removing or precluding formation of an amount of nitrosating agent and/or an N-nitroso compound in an enclosure of a pharmaceutical drug package to inhibit a potential adverse health effect on a patient associated with the nitrosating agent or N-nitroso compound, the method comprising:

providing at least one pharmaceutical dosage form in the enclosure of the pharmaceutical drug package, thereby forming a headspace in the enclosure in a portion of the enclosure not occupied by the at least one pharmaceutical dosage form, the at least one pharmaceutical dosage form having in it, on it, or having a propensity to form, emit, or react with the nitrosating agent and/or N-nitroso compound that is associated with the potential adverse health effect on the patient; and providing an entrained polymer component within the headspace, the entrained polymer component comprising a blended form of a base polymer and a silica gel active agent;

wherein the entrained polymer component is effective to decrease, mitigate, remove or preclude the formation of the amount of nitrosating agent and/or N-nitroso compound in the headspace and/or in the at least one pharmaceutical dosage form, thereby inhibiting the potential adverse health effect on the patient associated with the nitrosating agent or N-nitroso compound.

1H. A method of decreasing, mitigating, removing or precluding formation of an amount of nitrosating agent and/or an N-nitroso compound in an enclosure of a pharmaceutical drug package to inhibit a potential adverse health effect on a patient associated with the nitrosating agent or N-nitroso compound, the method comprising:

providing at least one pharmaceutical dosage form in the enclosure of the pharmaceutical drug package, thereby forming a headspace in the enclosure in a portion of the enclosure not occupied by the at least one pharmaceutical dosage form, the at least one pharmaceutical dosage form having in it, on it, or having a propensity to form, emit, or react with the nitrosating agent and/or N-nitroso compound that is associated with the potential adverse health effect on the patient; and providing an entrained polymer component within the headspace, the entrained polymer component comprising a blended form of a base polymer and a silica gel active agent;

wherein the entrained polymer component is effective to decrease, mitigate, remove or preclude the formation of the amount of nitrosating agent and/or N-nitroso compound in the headspace and/or in the at least one pharmaceutical dosage form, thereby inhibiting the potential adverse health effect on the patient associated with the nitrosating agent or N-nitroso compound.

2H. The method as recited in embodiment 1H wherein the polymer-based oxygen scavenging material comprises a polymer having a structural unit represented by Formula (III):

(III)

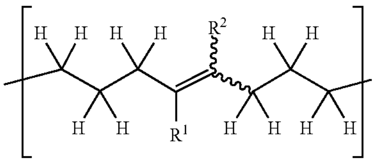

wherein $R^1$ and $R^2$ are independently chosen from H and $C_{1-6}$alkyl.

3H. The method as recited in embodiment 2H, wherein $R^1$ and $R^2$ are H.

4H. The method as recited in any one of embodiments 1H, 2H and 3H, wherein the polymer-based oxygen scavenging material further comprises a transition metal salt chosen from an iron salt, a nickel salt, a copper salt, a manganese salt and a cobalt salt.

5H. The method as recited in embodiment 4H, wherein the transition metal salt is a cobalt alkanoate.

6H. The method as recited in embodiment 4H, wherein the transition metal salt is cobalt(II) stearate.

7H. The method as recited in any one of embodiments 1H-6H, wherein the polymer-based oxygen scavenging material further comprises a compound chosen from $TiO_2$, $V_2O_5$, $MoO_3$, $CrO_3$, $WO_3$, $WO_2$, $WCl_2O_2$, and $WOCl_4$.

8H. The method as recited in any one of embodiments 1H-6H, wherein the polymer-based oxygen scavenging material further comprises $WO_3$.

9H. The method as recited in any one of embodiments 1H-8H, wherein the entrained polymer component comprises a polymeric channeling agent that is present in a range of from 1% to 25%, optionally 2% to 15%, optionally 2% to 6%, optionally 3% to 12%, optionally 5% to 20%, optionally 8% to 15%, optionally 10% to 20%, optionally 10% to 15%, or optionally 10% to 12% by weight with respect to total weight of the entrained polymer component.

10H. The method as recited in embodiment 9H, wherein the polymeric channeling agent forms interconnecting channels through the entrained polymer component.

11H. The method as recited in embodiment 10H, wherein at least a portion of the active agent is contained within the interconnecting channels, the interconnecting channels providing transmissibility of gas, volatilized N-nitroso compounds and/or nitrosating agents between the interconnecting channels and an exterior of the entrained polymer component through channel openings formed at outer surfaces of the entrained polymer component.

12H. The method as recited in any one of embodiments 9H to 11H, wherein the channeling agent is selected from one or more of the group consisting of: polyglycol, polyethylene glycol (PEG), ethylene-vinyl alcohol (EVOH), polyvinyl alcohol (PVOH), glycerin polyamine, polyurethane, polycarboxylic acid, a propylene oxide polymerisate-monobutyl ether, a propylene oxide polymerisate monobutyl ether, propylene oxide polymerisate, ethylene vinyl acetate, nylon 6, nylon 66, and vinylpyrrolidone-vinyl acetate copolymer 60/40 (PVPVA 64).

13H. The method as recited in any one of embodiments 9H to 12H, wherein the base polymer is selected from one or more of the group consisting of: polypropylene, polyethylene, polyisoprene, polybutadiene, polybutene, polysiloxane, polycarbonate, polyamide, ethylene-vinyl acetate copolymer, ethylene-methacrylate copolymer, poly(vinylchloride), polystyrene, polyester, polyanhydride, polyacrylianitrile, polysulfone, polyacrylic ester, acrylic, polyurethane and polyacetal.

14H. The method as recited in any one of embodiments 9H to 13H, wherein the active agent is present in a range of from 10% to 80%, optionally 20% to 70%, optionally 30% to 70%, optionally 30% to 60%, optionally 30% to 50%, optionally 35% to 70%, optionally 35% to 60%, optionally 35% to 55%, optionally 35% to 50%, optionally 40% to 70%, optionally 40% to 60%, optionally 40% to 50%, optionally 45% to 60%, optionally 50% to 60% by weight with respect to the total weight of the entrained polymer component.

15H. The method as recited in any one of embodiments 9H to 14H, wherein the N-nitroso compound is selected from the group consisting of NDMA, NDEA and NDIPA.

16H. The method as recited in any one of embodiments 9H to 15H, wherein the potential adverse health effect is carcinogenicity.

17H. The method as recited in any one of embodiments 9H to 16H, further comprising administering the at least one pharmaceutical dosage form to the patient.

18H. The method as recited in embodiment 17H, wherein the patient experiences therapeutic benefit from being administered the at least one pharmaceutical dosage form.

19H. The method as recited in embodiment 17H or 18H, wherein the patient is subjected to a reduced risk of the potential adverse health effect.

20H. The method as recited in any of embodiments 1A-1G or 1H-12H or 14H-19H, wherein the entrained polymer component is a blown film, the base polymer being a polyolefin or a polyester, the blown film optionally having a thickness of from 0.01 to 0.25 mm, optionally 0.01 to 0.15 mm, optionally 0.01 to 0.12 mm, optionally 0.01 to 1.0 mm, optionally 0.02 to 0.8 mm, optionally 0.05 to 0.5 mm, optionally 0.1 to 0.5 mm.

21H. The method as recited in any one of embodiments 1A-1G or 1H-19H, wherein the entrained polymer component is an extruded or cast film having a thickness of from 0.1 to 1.5 mm, optionally 0.2 to 1.0 mm, optionally 0.2 to 0.6 mm.

22H. The method as recited in embodiment 21H, wherein the package is a blister package comprising a backing and a cover attached to the backing, the cover and backing in combination forming the enclosure in the form of a blister cavity.

23H. The method as recited in embodiment 22H, wherein the film is chemically bonded to an inner wall of the enclosure by a heat seal, optionally by heat staking without a separate adhesive between the film and the inner wall.

24H. The method as recited in embodiment 23H, wherein inner wall is on a portion of the backing.

25H. The method as recited in any one of embodiments 1A-1G or 1H-21H, wherein the enclosure comprises an inner wall and the entrained polymer component is integral, chemically bonded or affixed to the inner wall.

26H. The method as recited in embodiment 25H, wherein the entrained polymer component is chemically bonded to the inner wall in the form of a coating or a liner.

27H. The method as recited in any one of embodiments 1A-1G or 1H-19H, wherein the package is a bottle or a vial and the entrained polymer component is integral, chemically bonded or affixed to a cap and/or interior wall of the bottle or vial.

28H. The method as recited in any one of embodiments 1A-1G or 1H-12H, wherein the entrained polymer component is provided in the form of a puck, an insert or a liner, optionally wherein the entrained polymer component is formed with the package in a multi-shot injection molding process.

29H. The method as recited in any one of embodiments 1A-1G or 1H-12H, wherein the package is a bottle or a vial and the entrained polymer component is in the form of a puck in the shape of a cylinder.

30H. The method as recited in embodiment 29H, wherein the puck in the shape of a cylinder has a height of 5 to 20 mm, optionally 14 to 20 mm and a diameter of 10 to 30 mm, optionally 18 to 25 mm.

31H. The method as recited in embodiment 29H or 30H, wherein the puck in the shape of a cylinder has the height and diameter dimensions of an industry standard 0.5 g size desiccant canister, 1 g size desiccant canister, 2 g size desiccant canister or 3 g size desiccant canister.

32H. The method as recited in embodiment 29H or 30H, wherein the puck in the shape of a cylinder has a height of about 7 mm and a diameter of about 16 mm, or a height of about 18 mm and a diameter of about 13-14 mm, or a height of about 16 mm and a diameter of about 19 mm, or a height of about 21 mm and a diameter of about 18 mm, or a height of about 25 mm and a diameter of about 19 mm.

33H. The method as recited in any one of embodiments 1A-1G or 1H-32H, wherein the pharmaceutical dosage form comprises an active pharmaceutical ingredient or a pharmaceutically acceptable salt and/or enantiomer thereof selected from the group consisting of: Almotriptan, Metformin, Ranitidine, Amitriptyline, Nortriptyline, Betahistine, Chloropyramine, Citalopram, Sumatriptan, Lamisil, Terbisil, Zostavax, Bedaquiline, Brompheniramine, Cabergoline, Carbinoxamine, Chlophedianol, Chlorpheniramine, Chlorpromazine, Clarithromycin, Clomipramine, Clozapine, Cyclobenzaprine, Demeclocycline, Dexbrompheniramine, Dexchlorpheniramine, Diltiazem, Diphenhydramine, Doxepin, Doxycycline, Doxylamine, Eravacycline, Erythromycin, Escitalopram, Imipramine, Maralixibat, Masitinib, Methadone, Methylene Blue, Mifepristone, Minocycline, Olopatadine, Omadacycline, Padimate O, Pheniramine, Phenyltoloxamine, Promethazine, Propoxyphene, Pyrilamine, Quinupristin, Rivastigmine, Rizatriptan, Sarecycline, Sildenafil, Spinosad, Tamoxifen, Tapentadol, Telithromycin, Tetracycline, Thonzylamine, Tigecycline, Tramadol, Trimethobenzamide, Trimipramine, Ulipristal Acetate, Venlafaxine, Zolmitriptan, Tripelennamine, Desvenlafaxine, Orphenadrine, Terbinafine, Ethylisopropylamine, Sitagliptin, Losartan, Valsartan, Atomoxetine, Lidocaine, Azelastine, Duloxetine, Fluoxetine, Chloropyramine, Phenylephrine, Rasagiline, Reboxetine, Aripiprazole, Mitapivat, Rifampicin, Alogliptin, Ranolazine, Rotigotine, Azacyclonol, Quetiapine, Cinacalcet, Desloratadine, Nintedanib, Sildenafil, Landiolol, Mirabegron, Mirtazapine, Valaciclovir, Pramipexole, Ranolazine, Ribociclib, Tetracaine, Trimetazidine, Varenicline, Vortioxetine, Methylphenidate, Paroxetine, Piperidine, Moxifloxacin, Daridorexant, Rotigotine, Ropivacaine, Ambroxol, Atenolol, Benazepril, Betaxolol, Bisoprolol, Bumetanide, Bupropion, Celiprolol, Cilazapril, Ciprofloxacin, Dabigatran Etexilate, Trimebutine, Diclofenac, Dorzolamide, Enalapril, Esmolol, Isosorbide mononitrate, Imatinib, Isosorbide mononitrate, Indapamide, Ketamine, Labetalol, Leniolisib, Levofloxacin, Lisinopril, Metoprolol, Moxifloxacin, Nebivolol, Perindopril, Arprazi-quantel, Propranolol, Pseudoephedrine, Quetiapine, Ramipril, Rivaroxaban, Salbutamol, Sertraline, Sotalol, Tamsulosin, Ticagrelor, Urapidil, Vildagliptin, Gliclazide, Mefenamic acid, Azithromycin, Calcium folinate, Calcium levofolinate, Hydrochlorothiazide, Quinapril and Ritonavir.

34H. The method as recited in any one of embodiments 1A-1G or 1H-33H, there being no physical barrier separating the pharmaceutical dosage form from the entrained polymer component.

35H. The method as recited in any one of embodiments 1A-1G or 1H-33H, wherein the pharmaceutical dosage form is not in a closed compartment within the enclosure that is separate from the entrained polymer component.

1I. A system for mitigating the presence of nitrosamine impurities from a drug product and a potential adverse effect on a patient associated therewith, the system comprising: a package comprising an enclosure and one or more pharmaceutical dosage forms housed within the enclosure, each of the one or more pharmaceutical dosage forms having in it, on it, or having a propensity to form or emit, a nitrosating agent and/or N-nitroso compound that is a source for the potential adverse effect, wherein a headspace is formed within a volume of the enclosure that is not occupied by the one or more pharmaceutical dosage forms, the headspace having disposed therein an effective amount of an active agent to mitigate formation of and/or reduce the presence of the nitrosating agent and/or N-nitroso compound in or on the one or more pharmaceutical dosage forms and/or in the headspace to improve patient safety by reducing the potential adverse effect associated with the drug product through the nitrosating agent and/or N-nitroso compound mitigation provided by the effective amount of active agent, the active agent being selected from the group consisting of: Vitamin E, sodium chloride, sodium hydroxide, almond flour, potassium hydroxide, ferulic acid, walnut powder, sodium bicarbonate, flaxseed powder, date seed powder, aloe vera powder, calcium carbonate, sodium carbonate, turmeric powder, ground cinnamon, anthocyanin (blueberry powder), coffee, astacanthin, evergreen (peppermint leaves), magnesium carbonate, caffeic acid, dried peppermint, spirulina, sodium alginate, zeaxanthin, beta cyclodextrin powder, acai powder, lycopene, L-ascorbic acid, 3 A or 4 A molecular sieve, calcium sulfate, green tea extract, grape seed powder, polyphenol (pomegranate powder), 13Y zeolite, hydrochloric acid, ferric oxide, crushed red pepper, pumpkin seed powder, Vitamin A, barley flour, ground clove, propyl gallate, beta carotene, silica gel, garlic extract, coenzyme Q10, beet root powder, magnesium chloride, and olive leaf extract.

1J. A method for decreasing, mitigating, removing or precluding formation of an amount of a nitrosamine in a pharmaceutical dosage form, the method comprising:

providing an enclosure;

positioning the pharmaceutical dosage form in the enclosure, thereby forming a headspace in the enclosure not occupied by the pharmaceutical dosage form, and positioning an active thereof within the headspace, the active agent being selected from the group consisting of: Vitamin E, sodium chloride, sodium hydroxide, almond flour, potassium hydroxide, ferulic acid, walnut powder, sodium bicarbonate, flaxseed powder, date seed powder, aloe vera powder, calcium carbonate, sodium carbonate, turmeric powder, ground cinnamon, anthocyanin (blueberry powder), coffee, astacanthin, evergreen (peppermint leaves), magnesium carbonate, caffeic acid, dried peppermint, spirulina, sodium alginate, zeaxanthin, beta cyclodextrin powder, acai powder, lycopene, L-ascorbic acid, 3 A or 4 A molecular sieve, calcium sulfate, green tea extract, grape seed powder, polyphenol (pomegranate powder), 13Y zeolite, hydrochloric acid, ferric oxide, crushed red pepper, pumpkin seed powder, Vitamin A, barley flour, ground clove, propyl gallate, beta carotene, silica gel, garlic extract, coenzyme Q10, beet root powder, magnesium chloride, and olive leaf extract, wherein the active agent is effective to reduce the amount of the nitrosamine in the pharmaceutical dosage form.

2J. The method of embodiment 1J, wherein the nitrosamine has a formula weight of 300 g/mol or less, optionally 200 g/mol or less, optionally 160 g/mol or less, optionally 120 g/mol or less.

3J. The method of embodiment 1J or 2J, wherein the nitrosamine has a vapor pressure at 20° C. of 0.2 Torr or higher, optionally 0.5 Torr or higher, optionally 1 Torr or higher, optionally 2 Torr or higher, optionally 3 torr or higher, optionally 4 torr or higher, or optionally 5 Torr or higher.

4J. The method of any one of embodiments 1J-3J, wherein the nitrosamine has a boiling point at atmospheric pressure of 250° C. or lower, optionally 225° C. or lower, optionally 200° C. or lower, optionally 190° C. or lower, optionally 180° C. or lower, optionally 170° C. or lower, or optionally 160° C. or lower.

5J. The method of any one of embodiments 1J-4J, wherein the nitrosamine is not 1-methyl-4-nitrosopiperazine, 1-cyclopentyl-4-nitrosopiperazine, or N-nitroso-3-azabicyclo[3.3.0]octane.

6J. The method of any one of embodiments 1J-5J, wherein the pharmaceutical dosage form does not comprise any one of rifampicin, rifapentine, or gliclazide.

7J. The method of any one of embodiments 1J-6J, wherein the pharmaceutical dosage form does not comprise either a hydrazone or a semicarbazide moiety.

8J. The method of any one of embodiments 1J-7J, wherein the pharmaceutical dosage form does not comprise a functional group that can undergo hydrolysis to provide a primary hydrazine.

9J. The method of any one of embodiments 1J-8J, wherein the nitrosamine is selected from the group consisting of NDMA, NDEA and NDIPA.

Blister Pack/Drug Delivery System

1K. A drug delivery system, comprising:

a blister pack configured to house multiple pharmaceutical dosage forms, the blister pack comprising:

a backing;

a cover attached to the backing, the cover and backing in combination forming at least one enclosure configured to contain a single pharmaceutical dosage form;

a single pharmaceutical dosage form housed within the at least one enclosure;

a headspace formed within a volume of the at least one enclosure that is not occupied by the single pharmaceutical dosage form; and an active agent positioned in the at least one enclosure, the active agent being selected from the group consisting of: Vitamin E, sodium chloride, sodium hydroxide, almond flour, potassium hydroxide, ferulic acid, walnut powder, sodium bicarbonate, flaxseed powder, date seed powder, aloe vera powder, calcium carbonate, sodium carbonate, turmeric powder, ground cinnamon, anthocyanin (blueberry powder), coffee, astacanthin, evergreen (peppermint leaves), magnesium carbonate, caffeic acid, dried peppermint, spirulina, sodium alginate, zeaxanthin, beta cyclodextrin powder, acai powder, lycopene, L-ascorbic acid, 3 A or 4 A molecular sieve, calcium sulfate, green tea extract, grape seed powder, polyphenol (pomegranate powder), 13Y zeolite, hydrochloric acid, ferric oxide, crushed red pepper, pumpkin seed powder, Vitamin A, barley flour, ground clove, propyl gallate, beta carotene, silica gel, garlic extract, coenzyme Q10, beet root powder, magnesium chloride, and olive leaf extract, wherein the active agent is effective to decrease, mitigate, remove or preclude the formation of an amount of nitrosating agent and/or N-nitroso compound in the headspace and/or in the pharmaceutical dosage form.

1L. A drug delivery system for mitigating a potential adverse effect associated with the drug, the system comprising:

a package comprising an enclosure and one or more pharmaceutical dosage forms housed within the enclosure, wherein a headspace is formed within a volume of the enclosure that is not occupied by the one or more pharmaceutical dosage forms; and a material that is capable of decreasing the rate of formation or mitigating formation of a nitrosating agent and/or an N-nitroso compound in a headspace within the package and/or in the pharmaceutical dosage form, optionally the material comprising an active agent selected from the group consisting of: Vitamin E, sodium chloride, sodium hydroxide, almond flour, potassium hydroxide, ferulic acid, walnut powder, sodium bicarbonate, flaxseed powder, date seed powder, aloe vera powder, calcium carbonate, sodium carbonate, turmeric powder, ground cinnamon, anthocyanin (blueberry powder), coffee, astacanthin, evergreen (peppermint leaves), magnesium carbonate, caffeic acid, dried peppermint, spirulina, sodium alginate, zeaxanthin, beta cyclodextrin powder, acai powder, lycopene, L-ascorbic acid, 3 A or 4 A molecular sieve, calcium sulfate, green tea extract, grape seed powder, polyphenol (pomegranate powder), 13Y zeolite, hydrochloric acid, ferric oxide, crushed red pepper, pumpkin seed powder, Vitamin A, barley flour, ground clove, propyl gallate, beta carotene, silica gel, garlic extract, coenzyme Q10, beet root powder, magnesium chloride, and olive leaf extract, wherein the material is separate and apart from the pharmaceutical dosage form stored within the package.

1M. A drug delivery system for mitigating a potential adverse effect associated with the drug, the system comprising:

(a) a blister pack configured to house one or more pharmaceutical dosage forms, the blister pack comprising:

(i) a backing;

(ii) a cover attached to the backing, the cover and backing in combination forming at least one enclosure configured to contain a single pharmaceutical dosage form;

(b) a single pharmaceutical dosage form housed within at least one enclosure;

(c) a headspace formed within a volume of the enclosure that is not occupied by the one or more pharmaceutical dosage forms; and (d) a material that is capable of decreasing the rate of formation or mitigating formation of a nitrosating agent and/or an N-nitroso compound in a headspace within the package and/or in the pharmaceutical dosage form, optionally the material comprising an active agent selected from the group consisting of: Vitamin E, sodium chloride, sodium hydroxide, almond flour, potassium hydroxide, ferulic acid, walnut powder, sodium bicarbonate, flaxseed powder, date seed powder, aloe vera powder, calcium carbonate, sodium carbonate, turmeric powder, ground cinnamon, anthocyanin (blueberry powder), coffee, astacanthin, evergreen (peppermint leaves), magnesium carbonate, caffeic acid, dried peppermint, spirulina, sodium alginate, zeaxanthin, beta cyclodextrin powder, acai powder, lycopene, L-ascorbic acid, 3 A or 4 A molecular sieve, calcium sulfate, green tea extract, grape seed powder, polyphenol (pomegranate powder), 13Y zeolite, hydrochloric acid, ferric oxide, crushed red pepper, pumpkin seed powder, Vitamin A, barley flour, ground clove, propyl gallate, beta carotene, silica gel, garlic extract, coenzyme Q10, beet root powder, magnesium chloride, and olive leaf extract, wherein the material is separate and apart from a pharmaceutical dosage form stored within the blister pack.

Package

1N. A package, comprising:

an enclosure;

at least one pharmaceutical dosage form located within the enclosure;

a headspace within the enclosure not occupied by the at least one pharmaceutical dosage form;

a nitrosating agent and/or an N-nitroso compound located in one or more of the headspace and the at least one pharmaceutical dosage form; and an active agent located within the headspace, the active agent being selected from the group consisting of: Vitamin E, sodium chloride, sodium hydroxide, almond flour, potassium hydroxide, ferulic acid, walnut powder, sodium bicarbonate, flaxseed powder, date seed powder, aloe vera powder, calcium carbonate, sodium carbonate, turmeric powder, ground cinnamon, anthocyanin (blueberry powder), coffee, astacanthin, evergreen (peppermint leaves), magnesium carbonate, caffeic acid, dried peppermint, spirulina, sodium alginate, zeaxanthin, beta cyclodextrin powder, acai powder, lycopene, L-ascorbic acid, 3 A or 4 A molecular sieve, calcium sulfate, green tea extract, grape seed powder, polyphenol (pomegranate powder), 13Y zeolite, hydrochloric acid, ferric oxide, crushed red pepper, pumpkin seed powder, Vitamin A, barley flour, ground clove, propyl gallate, beta carotene, silica gel, garlic extract, coenzyme Q10, beet root powder, magnesium chloride, and olive leaf extract, wherein the active agent is effective to decrease, mitigate, remove or preclude formation of an amount of nitrosating agent and/or N-nitroso compound in the enclosure and/or the at least one pharmaceutical dosage form.

Methods of Treatment

1O. A method for treating a patient having a medical condition with a pharmaceutical dosage form that comprises or can form a nitrosating agent and/or a N-nitroso compound, the method being configured to mitigate a potential adverse effect on a patient associated with the nitrosating agent and/or N-nitroso compound, the method comprising:

a) providing a package comprising an enclosure and one or more pharmaceutical dosage forms housed within the enclosure, wherein a headspace is formed within a volume of the enclosure that is not occupied by the one or more pharmaceutical dosage forms;

b) providing an amount of an active agent in the headspace that is effective in decreasing the rate of formation or mitigating formation of a nitrosating agent and/or an N-nitroso compound in a headspace and/or in the pharmaceutical dosage form within the package, the amount of active agent being separate and apart from the one or more pharmaceutical dosage forms, the active agent being selected from the group consisting of: Vitamin E, sodium chloride, sodium hydroxide, almond flour, potassium hydroxide, ferulic acid, walnut powder, sodium bicarbonate, flaxseed powder, date seed powder, aloe vera powder, calcium carbonate, sodium carbonate, turmeric powder, ground cinnamon, anthocyanin (blueberry powder), coffee, astacanthin, evergreen (peppermint leaves), magnesium carbonate, caffeic acid, dried peppermint, spirulina, sodium alginate, zeaxanthin, beta cyclodextrin powder, acai powder, lycopene, L-ascorbic acid, 3 A or 4 A molecular sieve, calcium sulfate, green tea extract, grape seed powder, polyphenol (pomegranate powder), 13Y zeolite, hydrochloric acid, ferric oxide, crushed red pepper, pumpkin seed powder, Vitamin A, barley flour, ground clove, propyl gallate, beta carotene, silica gel, garlic extract, coenzyme Q10, beet root powder, magnesium chloride, and olive leaf extract;

c) opening the enclosure to dispense the one or more pharmaceutical dosage forms; and d) administering the one or more pharmaceutical dosage forms to provide a therapeutically effective amount of drug to the patient for treating the medical condition with improved patient safety by reducing the potential adverse effect associated with the pharmaceutical dosage form through mitigation of the nitrosating agent and/or N-nitroso compound by the amount of active agent.

Pharmaceutical Dosage Form

1P. A pharmaceutical dosage form having a propensity to form or emit a nitrosating agent and/or N-nitroso compound that is a source for a potential adverse effect to a patient to whom the pharmaceutical dosage form is administered, the pharmaceutical dosage form being substantially free of an N-nitroso compound through inhibition of formation thereof and/or scavenging thereof by an effective amount of active agent provided in a headspace of a package enclosure when the pharmaceutical dosage form is housed within the enclosure, the effective amount of active agent being separate and apart from the pharmaceutical dosage form, the active agent being selected from the group consisting of: Vitamin E, sodium chloride, sodium hydroxide, almond flour, potassium hydroxide, ferulic acid, walnut powder, sodium bicarbonate, flaxseed powder, date seed powder, aloe vera powder, calcium carbonate, sodium carbonate, turmeric powder, ground cinnamon, anthocyanin (blueberry powder), coffee, astacanthin, evergreen (peppermint leaves), magnesium carbonate, caffeic acid, dried peppermint, spirulina, sodium alginate, zeaxanthin, beta cyclodextrin powder, acai powder, lycopene, L-ascorbic acid, 3 A or 4 A molecular sieve, calcium sulfate, green tea extract, grape seed powder, polyphenol (pomegranate powder), 13Y zeolite, hydrochloric acid, ferric oxide, crushed red pepper, pumpkin seed powder, Vitamin A, barley flour, ground clove, propyl gallate, beta carotene, silica gel, garlic extract, coenzyme Q10, beet root powder, magnesium chloride, and olive leaf extract.

2P. The pharmaceutical dosage form of embodiment 1J, wherein the pharmaceutical dosage form is substantially free of the N-nitroso compound such that the pharmaceutical dosage form includes less than 100%, optionally less than 90%, optionally less than 80%, optionally less than 70% of the FDA or EMA permitted N-nitroso compound content in effect as of 1 Jan. 2024.

3P. The pharmaceutical dosage form of embodiment 1J or 2J, wherein the pharmaceutical dosage form is substantially free of the N-nitroso compound such that the pharmaceutical dosage form includes less than 1500 ppm, optionally less than 400 ppm, optionally less than 100 ppm, optionally less than 95 ppm, optionally less than 90 ppm, optionally less than 85 ppm, optionally less than 80 ppm, optionally less than 75 ppm, optionally less than 70 ppm, optionally less than 65 ppm, optionally less than 60 ppm, optionally less than 55 ppm, optionally less than 50 ppm, optionally less than 45 ppm, optionally less than 40 ppm, optionally less than 35 ppm, optionally less than 25 ppm, optionally less than 20 ppm, optionally less than 15 ppm, optionally less than 14 ppm, optionally less than 13 ppm, optionally less than 12 ppm, optionally less than 11 ppm, optionally less than 10 ppm, optionally less than 9 ppm, optionally less than 8 ppm, optionally less than 7 ppm, optionally less than 6 ppm, optionally less than 5 ppm, optionally less than 4 ppm, optionally less than 3 ppm, optionally less than 2 ppm, optionally less than 1 ppm, optionally less than 0.9 ppm, optionally less than 0.8 ppm, optionally less than 0.7 ppm, optionally less than 0.6 ppm, optionally less than 0.5 ppm, optionally less than 0.4 ppm, optionally less than 0.3 ppm, optionally less than 0.2 ppm, optionally less than 0.1 ppm of total N-nitroso compound.

Blown Film

1Q. A blown film entrained polymer component comprising:

a blended form, comprising:

a base polymer; and at least one active agent dispersed within the base polymer, optionally wherein the active agent is in a granular, particulate or powdered form, the at least one active agent being selected from the group consisting of: ascorbic acid, Vitamin E, sodium chloride, sodium hydroxide, almond flour, potassium hydroxide, ferulic acid, walnut powder, sodium bicarbonate, flaxseed powder, date seed powder, aloe vera powder, calcium carbonate, sodium carbonate, turmeric powder, ground cinnamon, anthocyanin (blueberry powder), coffee, astacanthin, evergreen (peppermint leaves), magnesium carbonate, caffeic acid, dried peppermint, spirulina, sodium alginate, zeaxanthin, beta cyclodextrin powder, acai powder, lycopene, L-ascorbic acid, 3 A or 4 A molecular sieve, calcium sulfate, green tea extract, grape seed powder, polyphenol (pomegranate powder), 13Y zeolite, hydrochloric acid, ferric oxide, crushed red pepper, pumpkin seed powder, Vitamin A, barley flour, ground clove, propyl gallate, beta carotene, silica gel, garlic extract, coenzyme Q10, beet root powder, magnesium chloride, olive leaf extract, and polymer-based oxygen scavenger.

2Q. The blown film entrained polymer component as recited in embodiment 1Q, wherein the base polymer is chosen from a polyolefin and a polyester.

3Q. The blown film entrained polymer component as recited in embodiment 2Q, wherein the base polymer is a polyolefin having formula $(\text{—}CH_2CHR\text{—})_n$, wherein R is chosen from H and $C_{1-10}$alkyl.

4Q. The blown film entrained polymer component as recited in embodiment 2Q, wherein the base polymer is a polyester.

5Q. The blown film entrained polymer component as recited in embodiment 4Q, wherein the polyester has formula $(OOC\text{—}Y\text{—}COO\text{—}Z)_n$, wherein:

Y is 1,4-phenylene, and

Z is chosen from ethylene, butylene, hexylene, and 1,4-cyclohexenedimethylene.

6Q. The blown film entrained polymer component as recited in embodiment 4Q, wherein polyester has formula $((CH_2)_mCOO)_n$, wherein m is chosen from 1, 2, 3, 4, and 5.

7Q. The blown film entrained polymer component as recited in embodiment 4Q, wherein the polyester has formula $(\text{—}CHRCOO\text{—})_n$, wherein R is chosen from H and $C_{1-10}$alkyl.

8Q. The blown film entrained polymer component as recited in either one of embodiments 3Q and 7Q, wherein R is chosen from H, $CH_3$, $(CH_2)CH_3$, $(CH_2)_3CH_3$, $(CH_2)_5CH_3$, and $(CH_2)_7CH_3$.

9Q. The blown film entrained polymer component as recited in embodiment 3Q, wherein R is chosen from $C_2H_5$, $C_4H_9$, and $C_6H_{13}$.

10Q. The blown film entrained polymer component as recited in embodiment 7Q, wherein R is $CH_3$.

11Q. The blown film entrained polymer component as recited in any one of embodiments 1Q-7Q, wherein the polymer composition is a monolithic material.

12Q. The blown film entrained polymer component as recited in any one of embodiments 1Q-9Q, wherein the base polymer ranges from 10% to 80%, optionally from 20% to 70%, optionally from 30% to 60%, optionally from 40% to 50%, optionally from 45% to 65%, optionally from 45% to 60%, optionally from 45% to 55%, optionally from 50% to 70%, optionally from 50% to 60%, optionally from 55% to 65%, optionally from 55% to 60% by weight of the entrained polymer material.

13Q. The blown film entrained polymer component as recited in any one of embodiments 1Q-3Q, 8Q and 10Q-12Q, wherein the base polymer is chosen from polyethylene, polypropylene, and a polyethylene/polypropylene copolymer.

14Q. The blown film entrained polymer component as recited in embodiment 1Q, wherein the base polymer is a block copolymer.

15Q. The blown film entrained polymer component as recited in embodiment 14Q, wherein the block copolymer comprises polyester segments and polyether segments.

16Q. The blown film entrained polymer component as recited in embodiment 14Q, wherein the polyester segment is poly(alkylene terephthalate).

17Q. The blown film entrained polymer component as recited in embodiment 16Q, wherein the polyester segment is poly(butylene terephthalate).

18Q. The blown film entrained polymer component as recited in any one of embodiments 14Q-17Q, wherein the polyether segment is a poly(alkylene glycol).

19Q. The blown film entrained polymer component as recited in embodiment 18Q, wherein the polyether segment is chosen from polyethylene glycol, polypropylene glycol, and polytetramethylene glycol.

20Q. The blown film entrained polymer component as recited in embodiment 14Q, wherein the block copolymer is HYTREL®, optionally HYTREL® 7246.

21Q. The blown film entrained polymer component as recited in any one of embodiments 1Q-20Q, wherein the active agent comprises 1% to 70%, optionally 10% to 80%, optionally, optionally 20% to 70%, optionally 35% to 65%, optionally from 40% to 60%, optionally from 45% to 55% by weight with respect to the total weight of the material.

22Q. The blown film entrained polymer component as recited in any one of embodiments 1Q-21Q, further comprising a channeling agent, optionally wherein the channeling agent is present in a range of 1% to 25%, optionally from 2% to 15%, optionally from 2% to 6%, optionally from 3% to 12%, optionally from 5% to 20%, optionally from 8% to 15%, optionally from 10% to 20%, optionally from 10% to 15%, or optionally from 10% to 12% by weight with respect to total weight of the blown film entrained polymer.

23Q. The blown film entrained polymer component as recited in embodiment 22Q, wherein the channeling agent is chosen from a polyglycol, glycerin polyamine, polyurethane, and polycarboxylic acid, or any combination of the foregoing.

24Q. The blown film entrained polymer component as recited in embodiment 22Q, wherein the channeling agent is chosen from propylene oxide polymerisate, propylene oxide polymerisate-monobutyl ether, ethylene vinyl acetate (EVA), nylon, or any combination of the foregoing.

25Q. The blown film entrained polymer component as recited in embodiment 22A, wherein the channeling agent is polyethylene glycol (PEG).

26Q. A method for manufacturing the blown film entrained polymer component as recited in any one of embodiments 1Q-25Q, comprising the steps of:

extruding suitable precursor material that is a molten mix of the base polymer and the active agent in a screw extruder with warming to form a warmed extruded material;

passing the warmed extruded material through a die;

expanding and stretching the warmed extruded material with positive gas pressure to form an expanded and stretched material; and allowing the expanded and stretched material to cool, thus forming the blown film entrained polymer.

27Q. The method as recited in embodiment 26Q, wherein extrusion is performed with a rotation speed of between 5 rpm and 35 rpm, optionally between 10 rpm and 30 rpm, optionally between 10 rpm and 25 rpm, optionally between 10 rpm and 20 rpm.

28Q. The method as recited in either one of embodiments 26Q or 27Q, wherein extrusion is performed at a temperature between 140° C. and 180° C., optionally between 145° C. and 175° C., optionally between 150° C. and 170° C., optionally between 150° C. and 165° C.

29Q. The method as recited in any one of embodiments 26Q-28Q, wherein the method includes coextrusion of at least two layers for forming the expanded and stretched material.

30Q. The method as recited in embodiment 29Q, wherein a first layer includes the blown film entrained polymer and a second layer includes a polymer material without an active agent dispersed therein.

31Q. A container comprising the blown film entrained polymer as recited in any one of embodiments 1Q-25Q or made according to the methods as recited in any one of embodiments 26Q-30Q and an interior space suitable for storage of a pharmaceutical product.

32Q. The container of embodiment 31Q, wherein the container is one of a vial, a bottle, a pouch and a blister package.

33Q. The container of embodiment 31Q or 32Q, wherein the blown film entrained polymer is integral with or affixed to an internal wall of the container.

34Q. A method for reducing contamination in a pharmaceutical product by N-nitroso compounds, e.g. nitrosamines, the method comprising storing the pharmaceutical product in the container as recited in any one of embodiments 31Q-33Q and allowing the blown film entrained polymer to scavenge, mitigate formation of, or otherwise mitigate the N-nitroso compounds, e.g. nitrosamines.

Dependent Embodiments

1R. Any one of embodiments 1A-3Q, wherein the enclosure comprises an inner wall and the active agent is integral with or affixed to the inner wall.

2R. Any one of embodiments 1A-1R, wherein the pharmaceutical dosage form is an oral dosage form selected from the group consisting of tablet, sublingual tablet, chewable tablet, capsule and liquid-filled capsule.

3R. Any one of embodiments 1A-2R, wherein the N-nitroso compound is a nitrosable compound selected from primary amine, secondary amine, tertiary amine and quaternary ammonium salts.

4R. Any one of embodiments 1A-3R, wherein the N-nitroso compound is a nitrosable compound selected from primary amine, secondary amine, tertiary amine and quaternary ammonium salts.

5R. Any one of embodiments 1A-4R, wherein the N-nitroso compound is a reaction of product of a nitrosable compound and nitrite or a nitrosating agent.

6R. Embodiment 5K, wherein the nitrosating agent is nitrous acid.

7R. Embodiment 5K, wherein the nitrite is sodium nitrite.

8R. Any one of embodiments 1A-7R, wherein the N-nitroso compound is selected from the group consisting of N-nitrosodimethylamine, N-nitrosodiethylamine, and a volatile low molecular weight nitrosamine.

9R. Any one of embodiments 1A-8R, wherein the nitrosamine is selected from the group consisting of NDMA, NDEA and NDIPA.

10R. Any one of embodiments 1J, 1M, 1N, 1P, 1Q or 1R-9R, wherein the potential adverse effect is carcinogenicity.

11R. Any one of embodiments 1B-10R, wherein the active agent is provided in a sachet or cannister.

12R. Any one of embodiments 1B-10R, wherein the active agent is combined with a binder and compressed into a component that is optionally affixed to or chemically bonded to an interior wall of the enclosure.

13R. Any one of embodiments 1B-10R, wherein the package is a bottle or a vial and the active agent is provided in a component affixed to, chemically bonded with (optionally through multi-shot injection molding) or dispersed within a cap of the package and/or an interior wall of the package.

14R. Any one of embodiments 1B-10R, wherein the active agent is provided in granular, particulate or powdered form and is dispersed within a base polymer to form an entrained polymer, the entrained polymer optionally further comprising a channeling agent (optionally a polymer channeling agent) that forms channels within the entrained polymer.

15R. Embodiment 14R, the entrained polymer comprising the channeling agent, the channeling agent being present in a range of from 1% to 25%, optionally from 2% to 15%, optionally from 2% to 6%, optionally from 3% to 12%, optionally from 5% to 20%, optionally from 8% to 15%, optionally from 10% to 20%, optionally from 10% to 15%, or optionally from 10% to 12% by weight with respect to total weight of the blown film entrained polymer.

16R. Embodiment 15R, wherein the channeling agent is selected from one or more of the group consisting of: polyglycol, polyethylene glycol (PEG), ethylene-vinyl alcohol (EVOH), polyvinyl alcohol (PVOH), glycerin polyamine, polyurethane, polycarboxylic acid, a propylene oxide polymerisate-monobutyl ether, a propylene oxide polymerisate monobutyl ether, propylene oxide polymerisate, ethylene vinyl acetate, nylon 6, nylon 66, and vinylpyrrolidone-vinyl acetate copolymer 60/40 (PVPVA 64).

17R. Any one of embodiments 14R-16R, wherein the active agent is present 10% to 80%, optionally 20% to 70%, optionally 30% to 70%, optionally 30% to 60%, optionally 30% to 50%, optionally from 35% to 70%, optionally from 35% to 60%, optionally from 35% to 55%, optionally from 35% to 50%, optionally 40% to 70%, optionally from 40% to 60%, optionally from 40% to 50%, optionally from 45% to 60%, optionally from 50% to 60% by weight with respect to the total weight of the entrained polymer.

18R. Any one of embodiments 14R-17R, wherein the base polymer ranges from 10% to 70%, optionally from 20% to 60%, optionally from 20% to 50%, optionally from 20% to 40%, optionally from 30% to 70%, optionally from 30% to 60%, from 30% to 50%, optionally from 40% to 70%, optionally from 40% to 60%, optionally from 40% to 50% by weight of the total weight of the entrained polymer.

19R. Embodiment 14R, wherein the active agent is provided in the blown film entrained polymer of any one of embodiments 1Q-25Q, or made according to the method of any one of embodiments 26Q-30Q.

20R. Embodiment 19R, the blown film entrained polymer having a thickness of from 0.01 to 0.25 mm, optionally from 0.01 to 0.15 mm, optionally from 0.01 to 0.12 mm, optionally from 0.01 to 1.0 mm, optionally from 0.02 to 0.8 mm, optionally from 0.05 to 0.5 mm, optionally from 0.1 to 0.5 mm.

21R. Any one of embodiments 14R-20R, wherein the entrained polymer is provided as an extruded film or cast film.

22R. Embodiment 21K, the film having a thickness of from 0.1 to 1.2 mm, optionally 0.2 to 1.0 mm, optionally 0.2 to 0.6 mm.

23R. Any one of embodiments 1A-22R, wherein the pharmaceutical dosage form comprises an active pharmaceutical ingredient or a pharmaceutically acceptable salt and/or (where applicable) enantiomer thereof selected from the group consisting of: Almotriptan, Metformin, Ranitidine, Amitriptyline, Nortriptyline, Betahistine, Chloropyramine, Citalopram, Sumatriptan, Lamisil, Terbisil, Zostavax, Bedaquiline, Brompheniramine, Cabergoline, Carbinoxamine, Chlophedianol, Chlorpheniramine, Chlorpromazine, Clarithromycin, Clomipramine, Clozapine, Cyclobenzaprine, Demeclocycline, Dexbrompheniramine, Dexchlorpheniramine, Diltiazem, Diphenhydramine, Doxepin, Doxycycline, Doxylamine, Eravacycline, Erythromycin, Escitalopram, Imipramine, Maralixibat, Masitinib, Methadone, Methylene Blue, Mifepristone, Minocycline, Olopatadine, Omadacycline, Padimate O, Pheniramine, Phenyltoloxamine, Promethazine, Propoxyphene, Pyrilamine, Quinupristin, Rivastigmine, Rizatriptan, Sarecycline, Sildenafil, Spinosad, Tamoxifen, Tapentadol, Telithromycin, Tetracycline, Thonzylamine, Tigecycline, Tramadol, Trimethobenzamide, Trimipramine, Ulipristal Acetate, Venlafaxine, Zolmitriptan, Tripelennamine, Desvenlafaxine, Orphenadrine, Terbinafine, Ethylisopropylamine, Sitagliptin, Losartan, Valsartan, Atomoxetine, Lidocaine, Azelastine, Duloxetine, Fluoxetine, Chloropyramine, Phenylephrine, Rasagiline, Reboxetine, Aripiprazole, Mitapivat, Rifampicin, Alogliptin, Ranolazine, Rotigotine, Azacyclonol, Quetiapine, Cinacalcet, Desloratadine, Nintedanib, Sildenafil, Landiolol, Mirabegron, Mirtazapine, Valaciclovir, Pramipexole, Ranolazine, Ribociclib, Tetracaine, Trimetazidine, Varenicline, Vortioxetine, Methylphenidate, Paroxetine, Piperidine, Moxifloxacin, Daridorexant, Rotigotine, Ropivacaine, Ambroxol, Atenolol, Benazepril, Betaxolol, Bisoprolol, Bumetanide, Bupropion, Celiprolol, Cilazapril, Ciprofloxacin, Dabigatran Etexilate, Trimebutine, Diclofenac, Dorzolamide, Enalapril, Esmolol, Isosorbide mononitrate, Imatinib, Isosorbide mononitrate, Indapamide, Ketamine, Labetalol, Leniolisib, Levofloxacin, Lisinopril, Metoprolol, Moxifloxacin, Nebivolol, Perindopril, Arpraziquantel, Propranolol, Pseudoephedrine, Quetiapine, Ramipril, Rivaroxaban, Salbutamol, Sertraline, Sotalol, Tamsulosin, Ticagrelor, Urapidil, Vildagliptin, Gliclazide, Mefenamic acid, Azithromycin, Calcium folinate, Calcium levofolinate, Azithromycin, Hydrochlorothiazide, Quinapril and Ritonavir.

24R. Embodiment 23R, wherein the selected pharmaceutical dosage form is used to treat an associated medical condition(s) and/or any symptoms thereof as set forth in (a) U.S. Provisional Application No. 63/660,805, titled "MATERIALS AND METHODS FOR MITIGATING THE PRESENCE OF NITROSAMINES IN PACKAGING USING AN ACTIVE AGENT" and filed on Jun. 17, 2024, (b) the (2017) Physicians' desk reference (71st ed.) PDR Network, or (c) the website pdr.net (Prescribers' Digital Reference® website, accessed on Jun. 17, 2024). Each of these three documents/databases is incorporated by reference herein in its entirety, including all information it contains about the pharmaceutical dosage forms listed in Embodiment 23K, such as treatment indications, dosage and form. For example, Embodiment 23K (and related disclosure/claims) would cover use of Quetiapine, or its brand name SEROQUEL or SEROQUEL XR for: the adjunctive treatment of major depression in patients who have had an inadequate response to antidepressants alone; the treatment of major depressive disorder as monotherapy; the treatment of bipolar disorder, including mania and bipolar depression; the treatment of mania associated with bipolar I disorder; the treatment of bipolar disorder depressive episodes; the treatment of schizophrenia; the adjunct treatment of refractory OCD; the treatment of neurocognitive symptoms (e.g., impulsivity, executive functioning) associated with borderline personality disorder; the treatment of severe behavioral or psychological symptoms of dementia; or the treatment of neuropsychiatric symptoms associated with dementia with Lewy bodies that are unresponsive to other medications and non-medication treatments. These treatment indications are from the "Dosage And Indications" section under SEROQUEL XR based on a search for Quetiapine on pdr.net website (accessed on Jun. 17, 2024). This disclosure of indications for Quetiapine is merely exemplary and intended to direct the skilled artisan on how to locate associated medical condition(s) and/or any symptoms thereof with any of the dosage forms set forth in Embodiment 23R, from a search on the aforementioned website 25R. Embodiment 24R, wherein the selected pharmaceutical dosage form is administered based on corresponding dosing instructions/information set forth in any of the documents/databases cited in Embodiment 24R, and/or wherein the selected solid pharmaceutical dosage form may be administered based on or extrapolated from corresponding dosing instructions/information set forth in any of the documents/databases cited in Embodiment 24K for a corresponding liquid dosage form of the same drug.

Pharmaceutical Excipients

1S. A method of decreasing, mitigating, removing or precluding formation of an amount of nitrosating agent and/or an N-nitroso compound in an enclosure of a pharmaceutical excipient package, optionally to inhibit a potential adverse health effect on a patient associated with the nitrosating agent or N-nitroso compound, the method comprising:

(a) providing at least one pharmaceutical excipient in the enclosure of the pharmaceutical drug package, thereby forming a headspace in the enclosure in a portion of the enclosure not occupied by the at least one pharmaceutical excipient, the at least one pharmaceutical excipient having in it, on it, or having a propensity to form, emit, or react with the nitrosating agent and/or N-nitroso compound that is associated with the potential adverse health effect on the patient; and (b) providing an entrained polymer component within the headspace, the entrained polymer component comprising a blended form of a base polymer and an active agent selected from the group consisting of: sodium chloride, ascorbic acid, sodium bicarbonate, vitamin E, calcium carbonate, magnesium carbonate, silica gel, and polymer-based oxygen scavenger;

wherein the entrained polymer component is effective to decrease, mitigate, remove or preclude the formation of the amount of nitrosating agent and/or N-nitroso compound in the headspace and/or in the at least one pharmaceutical excipient, thereby optionally inhibiting the potential adverse health effect on the patient associated with the nitrosating agent or N-nitroso compound.

2S. The embodiment of 1S, wherein the at least one pharmaceutical excipient is selected from the group consisting of: microcrystalline cellulose (MCC), colloidal silicon dioxide, hypromellose (HPMC), povidone, mannitol, talc, sodium lauryl sulfate, polyvinyl alcohol, sodium starch glycolate, hydroxypropyl cellulose, poloxamer, citric acid, sodium chloride, sucrose, magnesium stearate, lactose monohydrate, corn starch, starch, croscarmellose sodium, polyethylene glycol, or crospovidone.

3S. The embodiment of 1S or 2S, wherein the at least one pharmaceutical excipient is in powder or granular form.

EXAMPLES

The invention is further illustrated by the following examples.

Example 1: Materials

Films

Films were manufactured using a twin screw 27 mm extruder to achieve an optimal thickness between 0.3 mm and 1.2 mm. Details on film formulations are provided in the Examples below when appropriate.

Blown Bottles

Blown bottles were manufactured using the formulations listed in Table 1.

TABLE 1

Blown Bottle Formulations (Inner Wall)

| Active Agent | Component | Percentage % (m/m) |
|---|---|---|
| Sodium Chloride | NaCl | 60.00% |
| | LDPE 2692 | 35.00% |
| | EVA-2528 | 5.00% |
| Sodium Bicarbonate | $NaHCO_3$ | 60.00% |
| | LDPE 2692 | 35.00% |
| | RESIN-CARBOWAX PEG4000 SEN NF | 5.00% |

Further properties of blown bottles are provided in Tables 2A-2C. In each case, unless otherwise noted, the middle layer was composed of HDPE 3954, and the inner and outer layers were composed of HDPE 3954 with 2% white pigment.

TABLE 2A

Blown Bottle Formulations for Layers

| | Overall dimensions | | Inner layer | | Middle layer | | Outer layer | |
|---|---|---|---|---|---|---|---|---|
| Active in Inner Layer | Thickness (mm) | Weight (g) | % | Thickness (mm) | % | Thickness (mm) | % | Thickness (mm) |
| None (control) | 1.3 | 22.3 | 20 | 0.26 | 60 | 0.78 | 20 | 0.26 |
| Sodium bicarbonate | 1.6 | 24.5 | 15 | 0.24 | 50 | 0.8 | 35 | 0.56 |
| Sodium Chloride | 1.4 | 25.1 | 25 | 0.35 | 50 | 0.7 | 25 | 0.35 |
| Calcium carbonate I* | 1.3 | 25.2 | 20 | 0.26 | 50 | 0.65 | 30 | 0.39 |

*See Example 12

TABLE 2B

Further Blown Bottle Formulations for Layers

| | Overall dimensions | | Inner layer | Middle layer* | Outer layer |
|---|---|---|---|---|---|
| Active in Inner Layer | Thickness (mm) | Weight (g) | Thickness (mm) | Thickness (mm) | Thickness (mm) |
| T-AC | 1.4 | 22.9 | 0.1168 | 0.3483 | 0.9746 |
| AC | 1.4 | 25.3 | 0.3324 | 0.161 | 0.8635 |
| Visparent | 1.4 | 21.1 | 0.1124 | 0.4096 | 0.6036 |
| Visparent with HDPE 3954 0.1 mm thin liner | 1.3 | 20.5 | 0.1712 + 0.1 mm liner | 0.3595 | 0.5763 |

*Middle layer: EVOH with EVALTM L171B (Kuraray) and adhesive tie layers (Admer)

TABLE 2C

Further Blown Bottle Formulations for Layers

| | Overall dimensions | | Inner layer | | Middle layer | | Outer layer | |
|---|---|---|---|---|---|---|---|---|
| Active in Inner Layer | Thickness (mm) | Weight (g) | % | Thickness (mm) | % | Thickness (mm) | % | Thickness (mm) |
| Calcium Carbonate II* | 1.3 | 25.3 | 20 | 0.26 | 60 | 0.78 | 20 | 0.26 |
| Vitamin E | 1.5 | 25.8 | 20 | 0.3 | 50 | 0.75 | 30 | 0.45 |
| Ascorbic Acid | 1.3 | 25 | 20 | 0.26 | 60 | 0.78 | 20 | 0.26 |

*See Example 12

Example 2: Effect of Active Agent on N-Nitrosamine Concentration from Metformin

A study was performed to examine the effect of the presence of an active agent in a 3-phase entrained polymer film on the concentration of an N-nitrosamine. Samples of the following films (1 $cm^2$): 4 A molecular sieves, L-ascorbic acid ("ascorbic acid"), Visparent, and TRIS modified activated carbon ("T-AC") were added to separate GC vials. The control did not have any film in the GC vial.

TABLE 3

Film Formulations

| Active | Material | Percentage in Film Formulation (wt %) | Thickness |
|---|---|---|---|
| 4A | 4A powder film 1 | 60% | 0.3 mm |
| | EVA-2528 | 3% | |
| | Resin-3040 | 37% | |
| Ascorbic Acid "A" formulation | L-Ascorbic Acid | 37 | 0.6 mm |
| | Elvax 3174 | 21 | |
| | Silica Gel Grade 11 | 15 | |
| | RESIN-3040 | 12 | |
| | Abscents 3000 | 10 | |
| | Carbowax 4000P | 5 | |
| Visparent | Visparent E100 | 17 | 0.3 mm |
| | RESIN-3040 | 35 | |
| | RESIN-HD8960 | 34 | |
| | ABSCENTS 3000 | 10 | |
| | Activator CC1020014 | 3 | |
| | Eval EVOH 0738 | 1 | |
| T-AC | T-AC (Chemsorb 1505-60-G5) | 30 | 0.8 mm |
| | RESIN-3040 | 70 | |

To each vial was then added 2 mL of a metformin forming solution, followed by 0.1 mL of a nitrite conjugate acid solution. Each vial was then quickly crimp sealed and aged in lab conditions at room temperature for 24 hrs.

The assay was performed using the Agilent 7697A Headspace Sampler, 6890GC/MSD System. The method conditions and parameters are given in Tables 4-6, below.

TABLE 4

| Agilent 7697A Headspace Sampler Conditions | |
|---|---|
| Oven Temperature | 130° C. |
| Loop Temperature | 180° C. |
| Transfer Line Temp | 185° C. |
| Vial Equilibration | 15 min |
| Injection duration | 1 min |
| Vial size (ml) | 20 mL |
| Fill Pressure | 15 psi |
| Loop fill mode | default |
| Injection volume | 0.2 μL |

TABLE 5

| Agilent 6890GC parameters | |
|---|---|
| Inlet (Split/Splitless) | Helium |
| Temp | 220° C. |
| Mode | Split |
| Split ratio | 5:1 |
| Equilibration time | 1 min |
| Oven Program | 70° C. for 4 min<br>20° C./min to 240° C.<br>hold for 3.5 min<br>Total cycle time 16.0 mins |

TABLE 5-continued

| Agilent 6890GC parameters | |
|---|---|
| Column | DB Wax UI<br>30 m × 0.250 mm × 0.25 μm<br>p/n 122-7032UI |
| Mode | constant pressure |
| Flow | 1 mL/min |

TABLE 6

| Agilent 5977 GC/MSD Conditions | |
|---|---|
| Source type | Extractor |
| Source Temp | 230° C. |
| Mass filter mode | SIM |
| NDMA m/z | 74 |
| Quad Temp | 150° C. |

Figure 3:
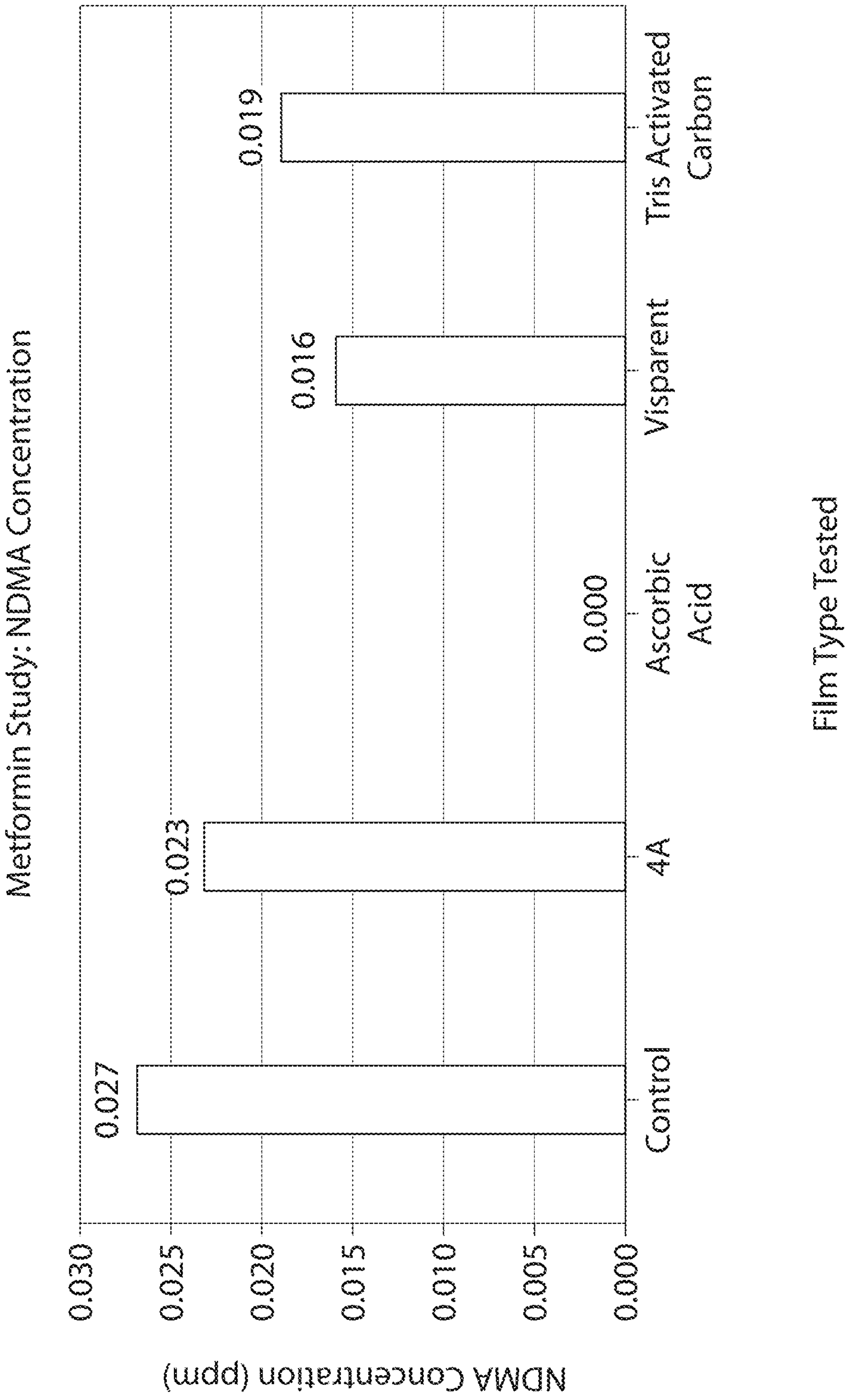
FIG. 3 is a graph that shows the reduction in the concentration of N-nitrosodimethylamine ("NDMA") in the presence of various materials.

The concentration of NDMA in the headspace of each vial was analyzed after one day of aging in lab conditions at room temperature. These results are shown in FIG. 3. The modified version did not use targeted analysis but used the NIST20 library match factor, and calculated an estimated ppm of analyte instead. These results are shown in Table 7.

TABLE 7

NDMA

| Active | NDMA (ppm) |
|---|---|
| Control | 0.027 |
| 4A | 0.023 |
| Ascorbic Acid "A" formulation | 0.000 |
| Visparent | 0.016 |
| T-AC | 0.019 |

The ascorbic acid-A film was the most effective in preventing the formation of NDMA.

Figure 4:
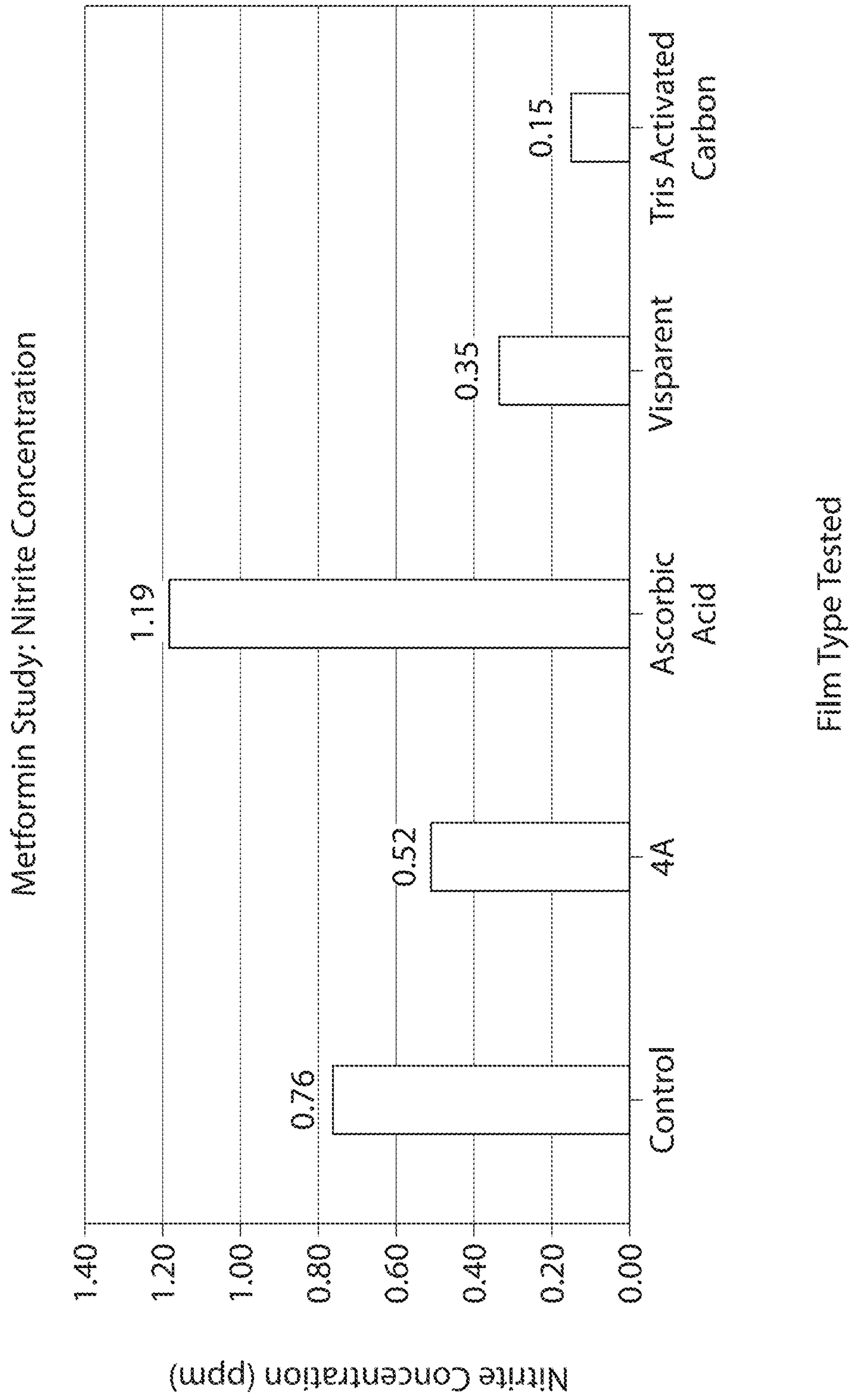
FIG. 4 is a graph that shows the change in the concentration of nitrite in the presence of various materials.
Figure 5:
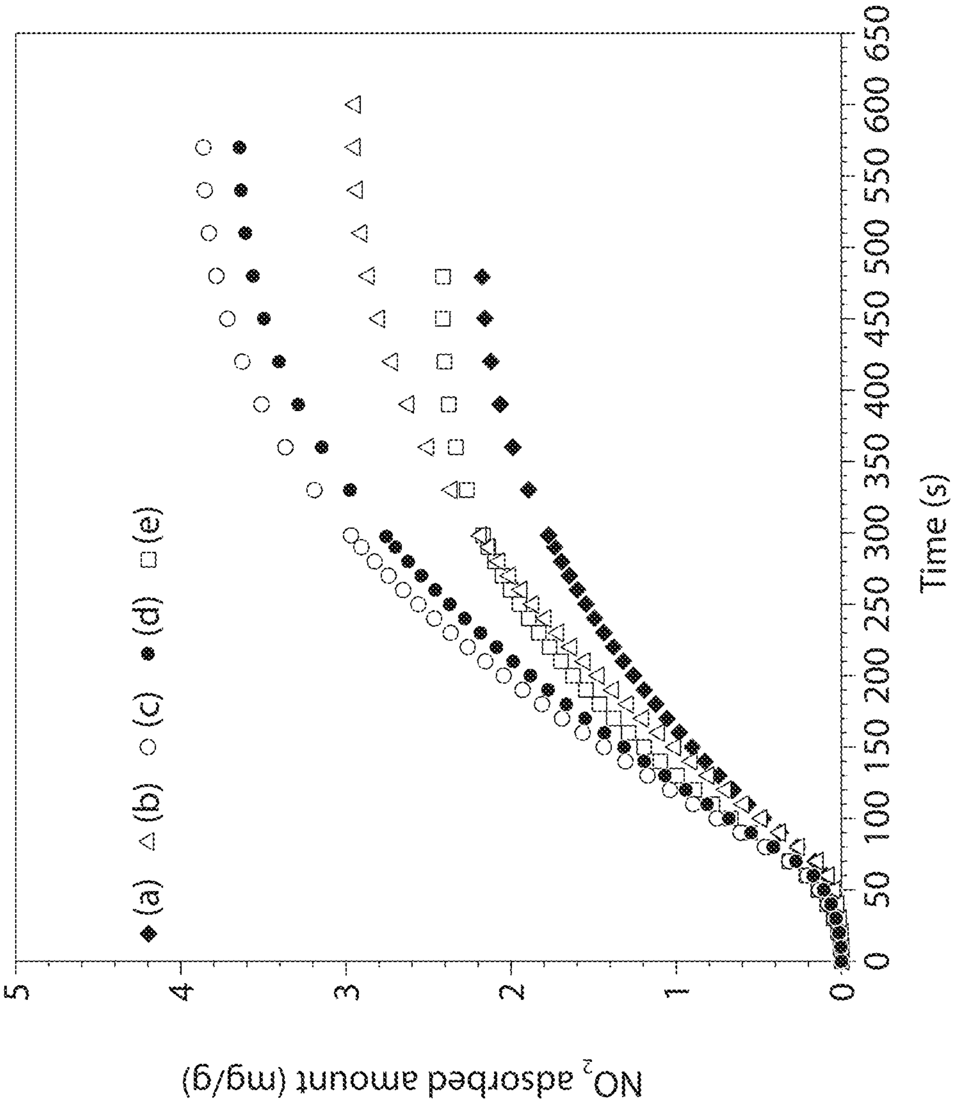
FIG. 5 is a graph that shows $NO_2$ adsorbed amount (mg/g) over time (s) using films with various actives (a) NaCl (b) Vitamin E (c) Ascorbic Acid "B" formulation (d) $NaHCO_3$ Sodium Bicarbonate "A" formulation (e) $NaHCO_3$ Sodium Bicarbonate "B" formulation.
Figure 6:
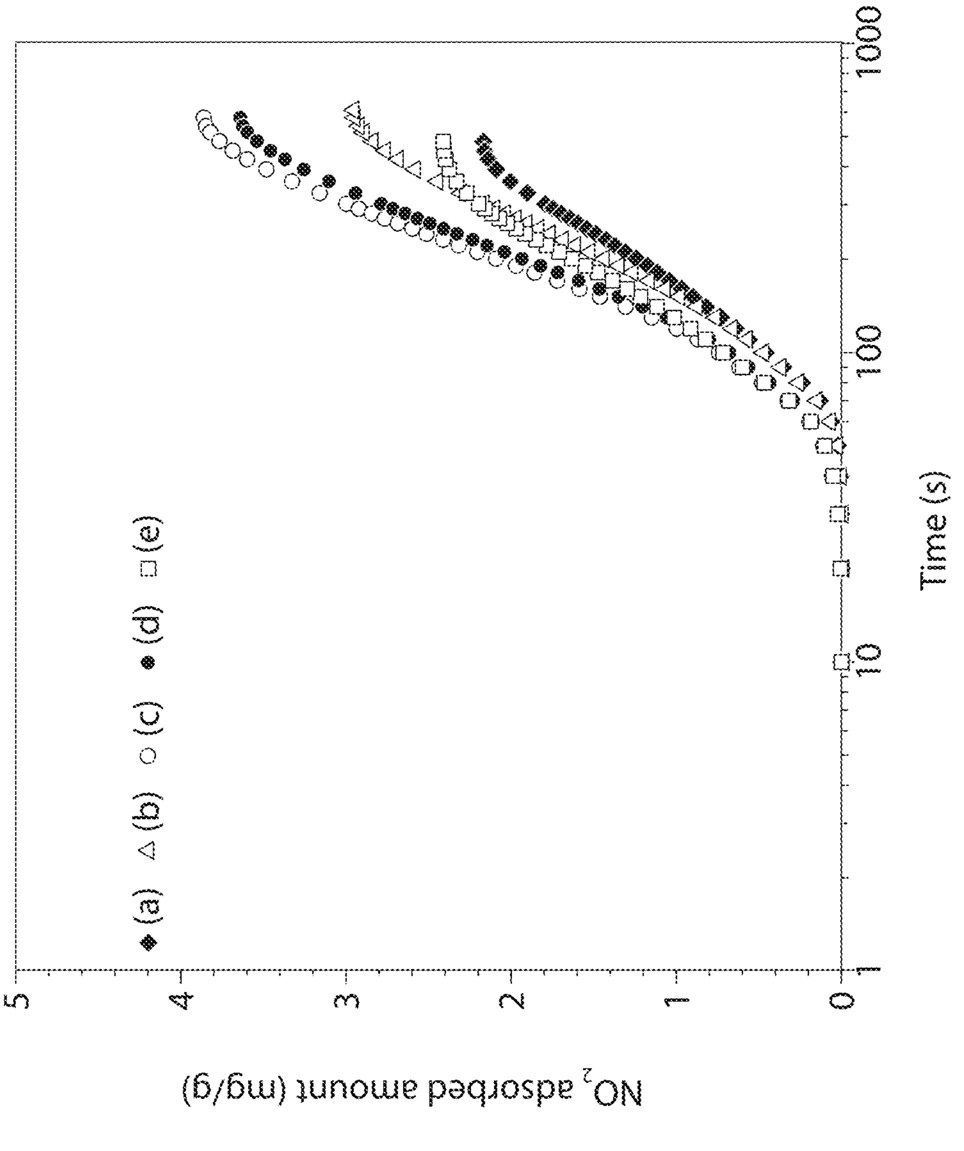
FIG. 6 is a graph that shows $NO_2$ adsorbed amount (mg/g) over log time (s) using film with various actives (a) NaCl (b) Vitamin E (c) Ascorbic Acid "B" formulation (d) $NaHCO_3$ Sodium Bicarbonate "A" formulation (e) $NaHCO_3$ Sodium Bicarbonate "B" formulation.
Figure 7:
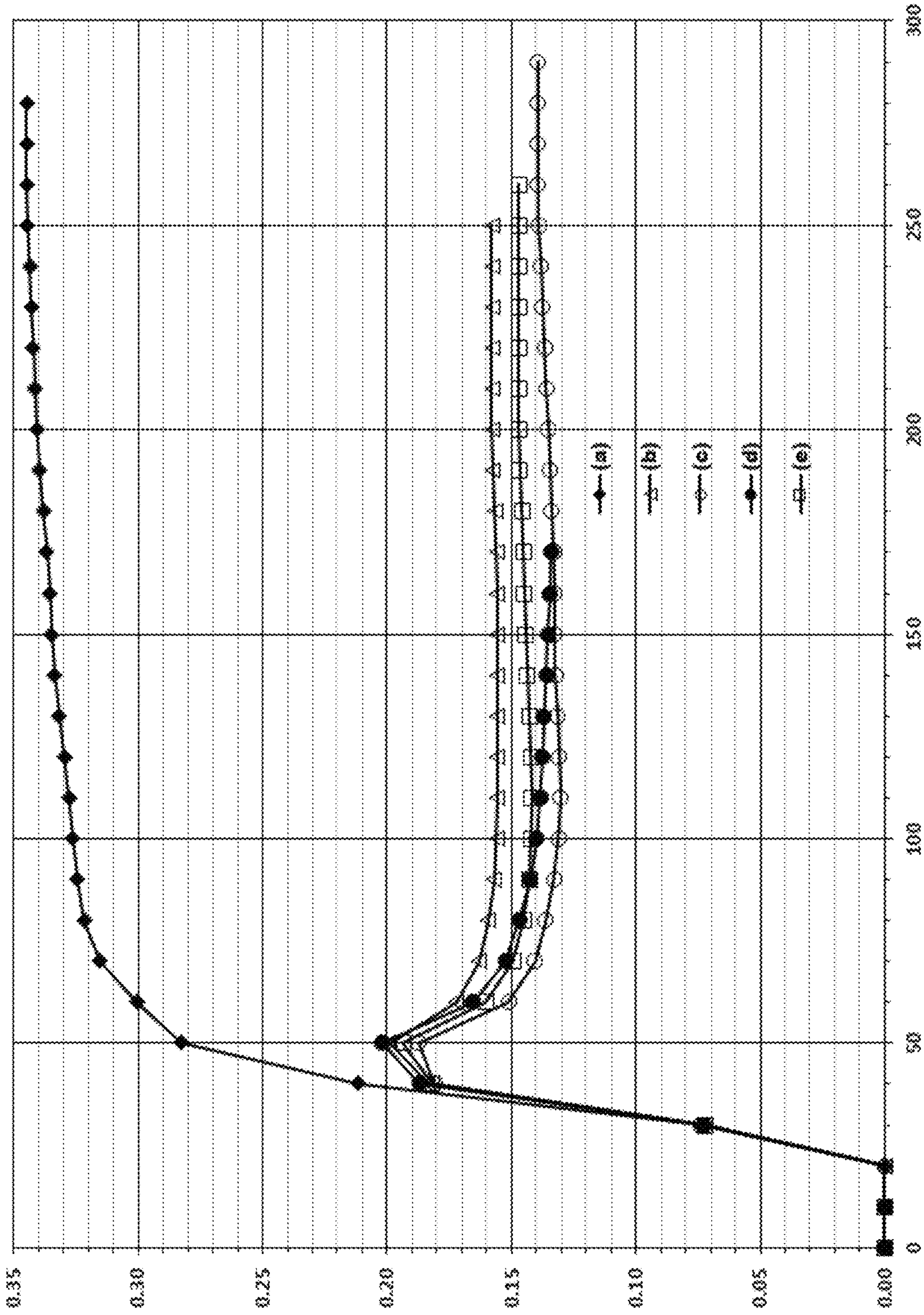
FIG. 7 is a graph that shows the amount of NO adsorbed by raw active agents (a) NaCl (b) vitamin E (c) Ascorbic acid (d) $NaHCO_3$ (e) $CaCO_3$; horizontal axis=time (sec) vertical axis=mg NO adsorption/g active agent.
Figure 8:
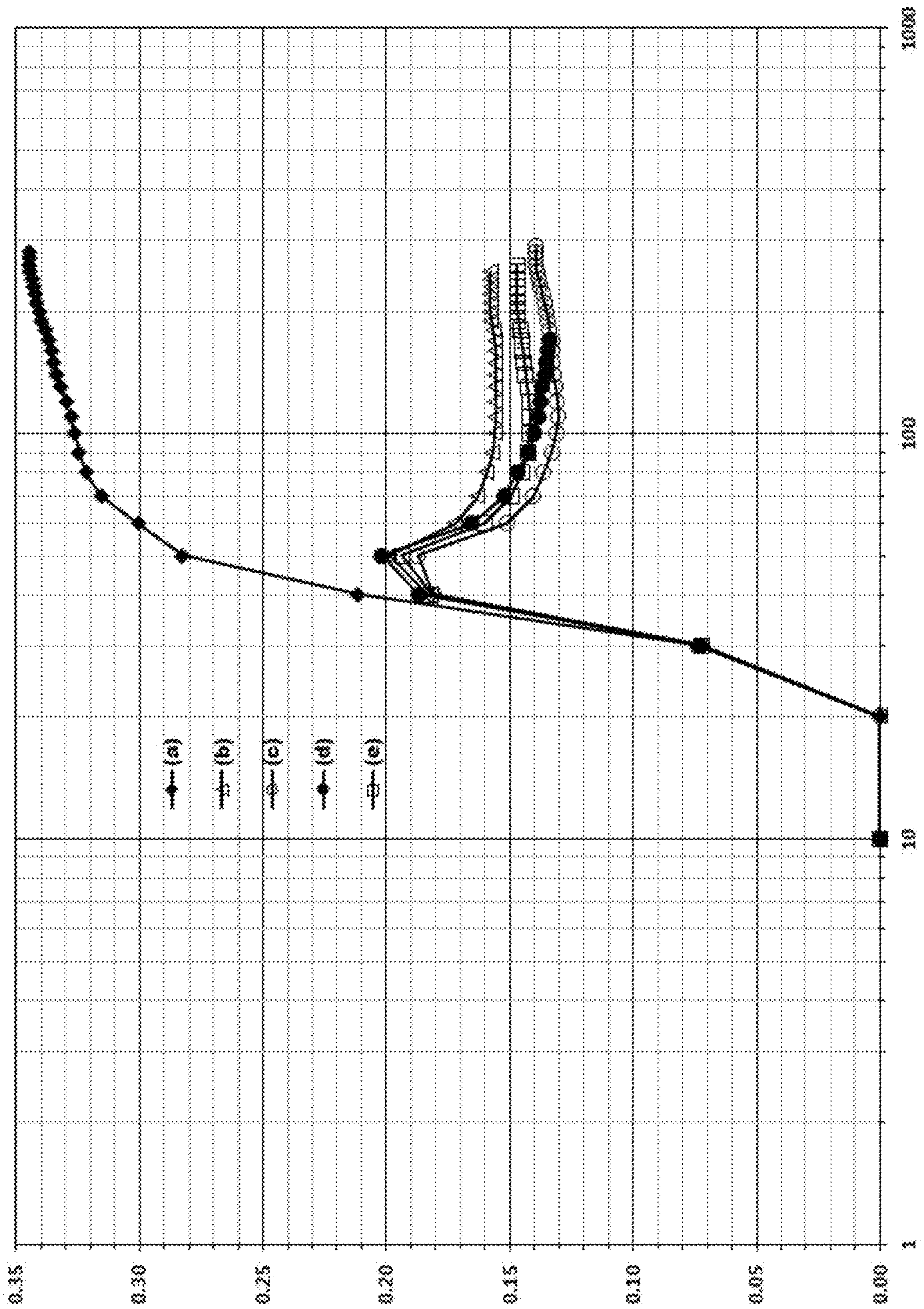
FIG. 8 is a graph that shows the amount of NO adsorbed over log time by raw active agents (a) NaCl (b) vitamin E (c) Ascorbic acid (d) $NaHCO_3$ (e) $CaCO_3$; horizontal axis=time (sec) vertical axis=mg NO adsorption/g active agent.
Figure 9:
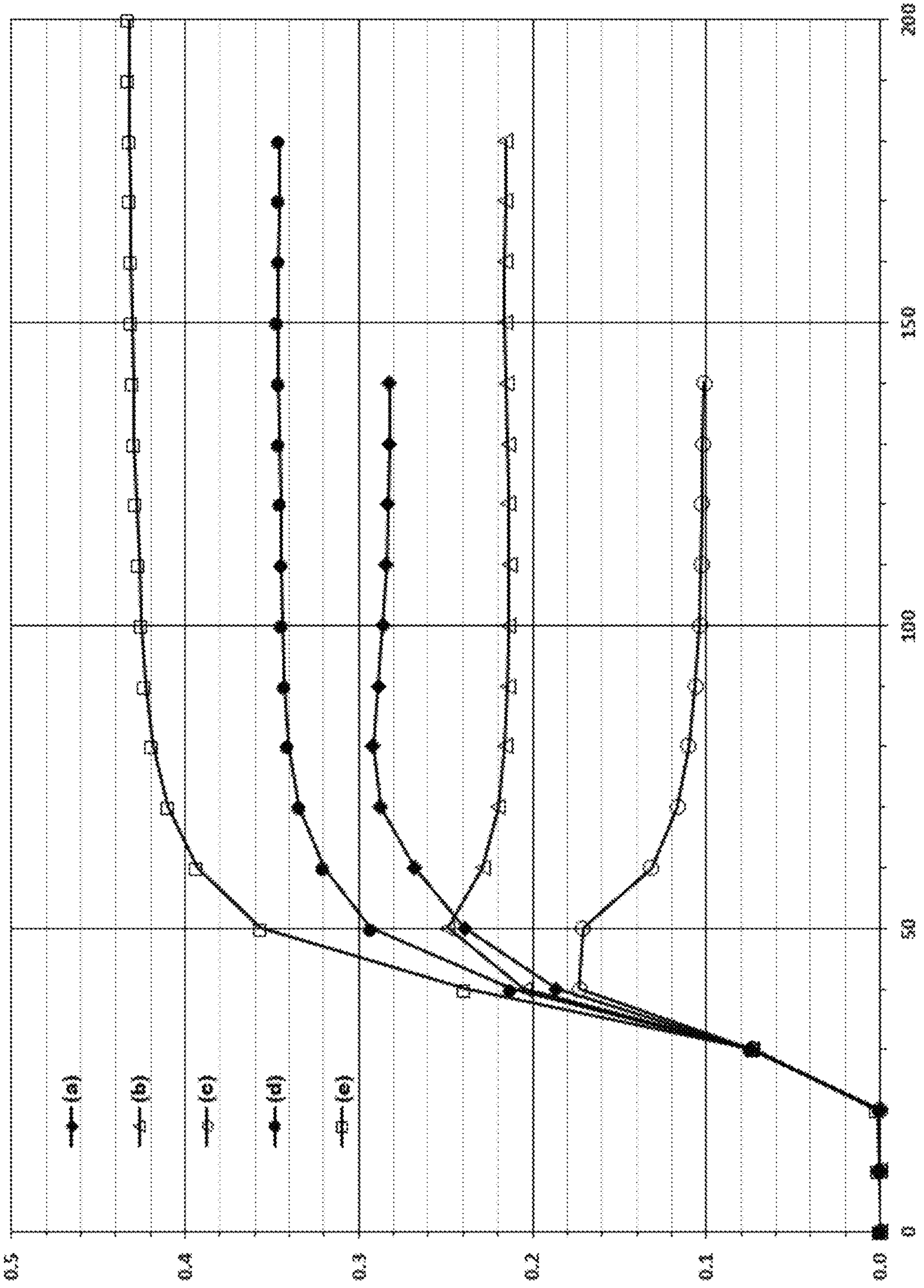
FIG. 9 is a graph that shows the amount of NO adsorbed by films containing active agents (a) NaCl (b) vitamin E (c) Ascorbic acid "B" formulation (d) $NaHCO_3$ Sodium Bicarbonate "A" formulation (e) $CaCO_3$; horizontal axis=time (sec) vertical axis=mg NO adsorption/g active agent.
Figure 10:
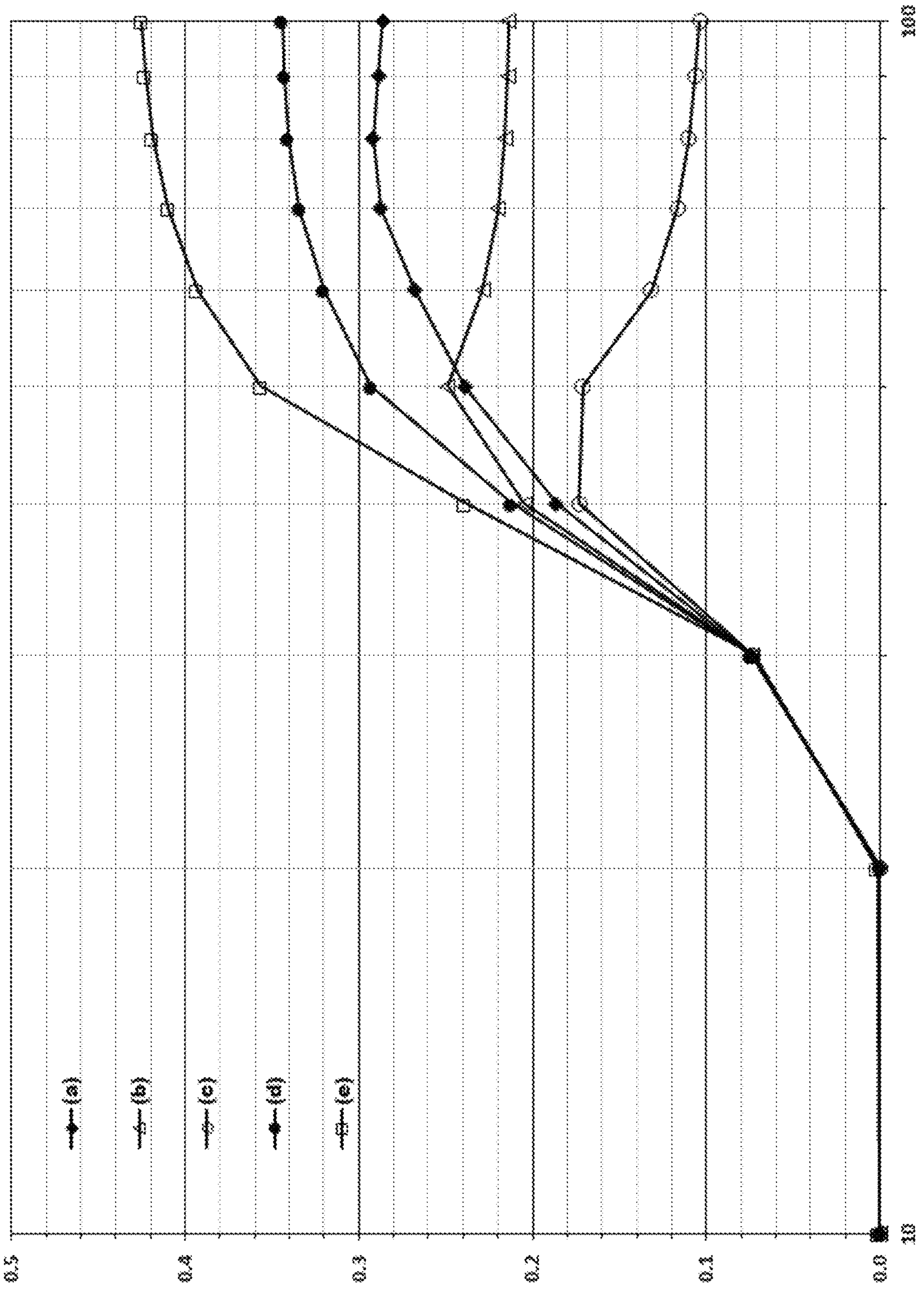
FIG. 10 is a graph that shows the amount of NO adsorbed over log time by films containing active agents (a) NaCl (b) vitamin E (c) Ascorbic acid "B" formulation (d) $NaHCO_3$ Sodium Bicarbonate "A" formulation (e) $CaCO_3$; horizontal axis=time (sec) vertical axis=mg NO adsorption/g active agent.
Figure 11:
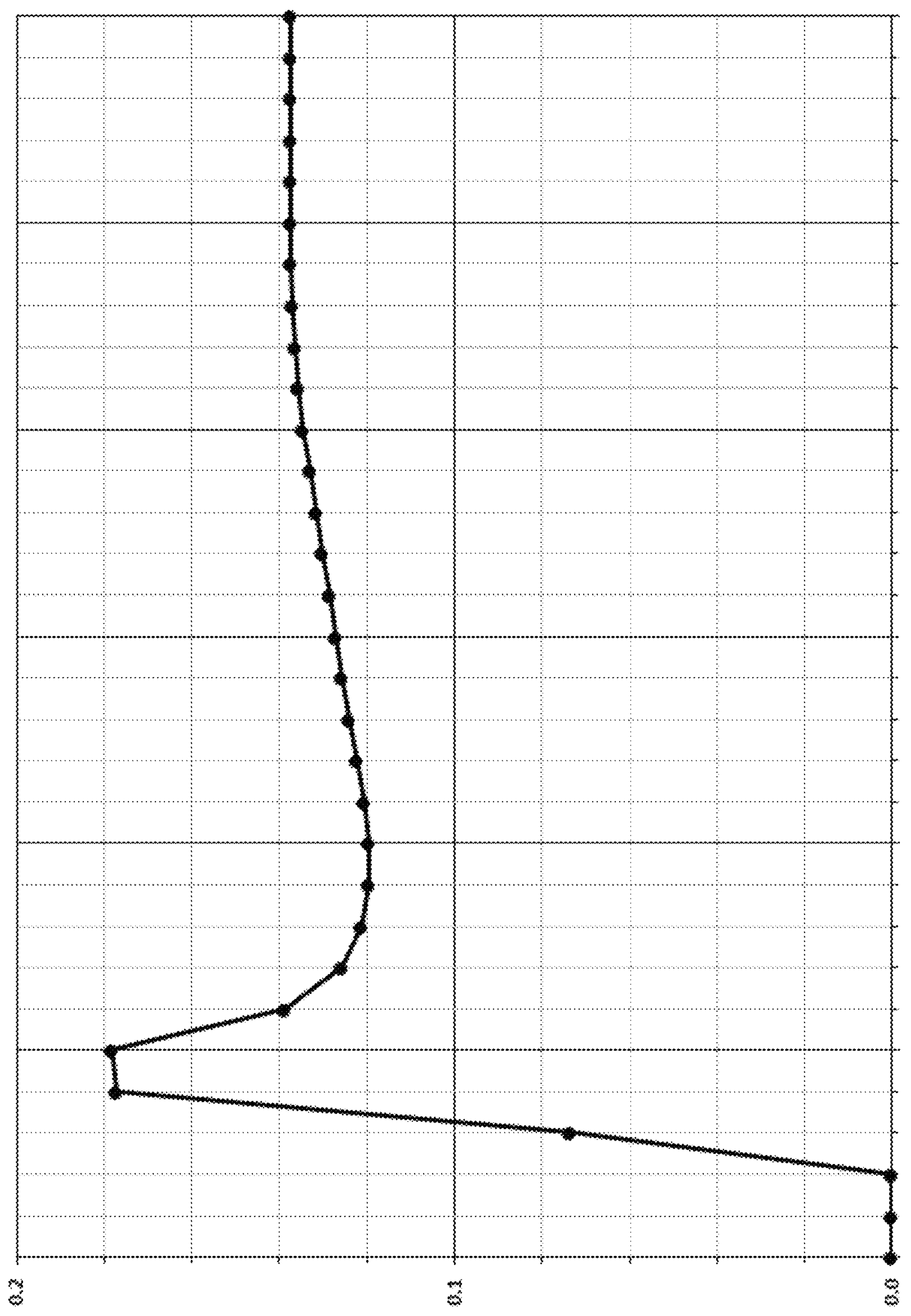
FIG. 11 is a graph that shows the amount of NO adsorbed by virgin Film A; horizontal axis=time (sec) vertical axis=mg NO adsorption/g film.
Figure 12:
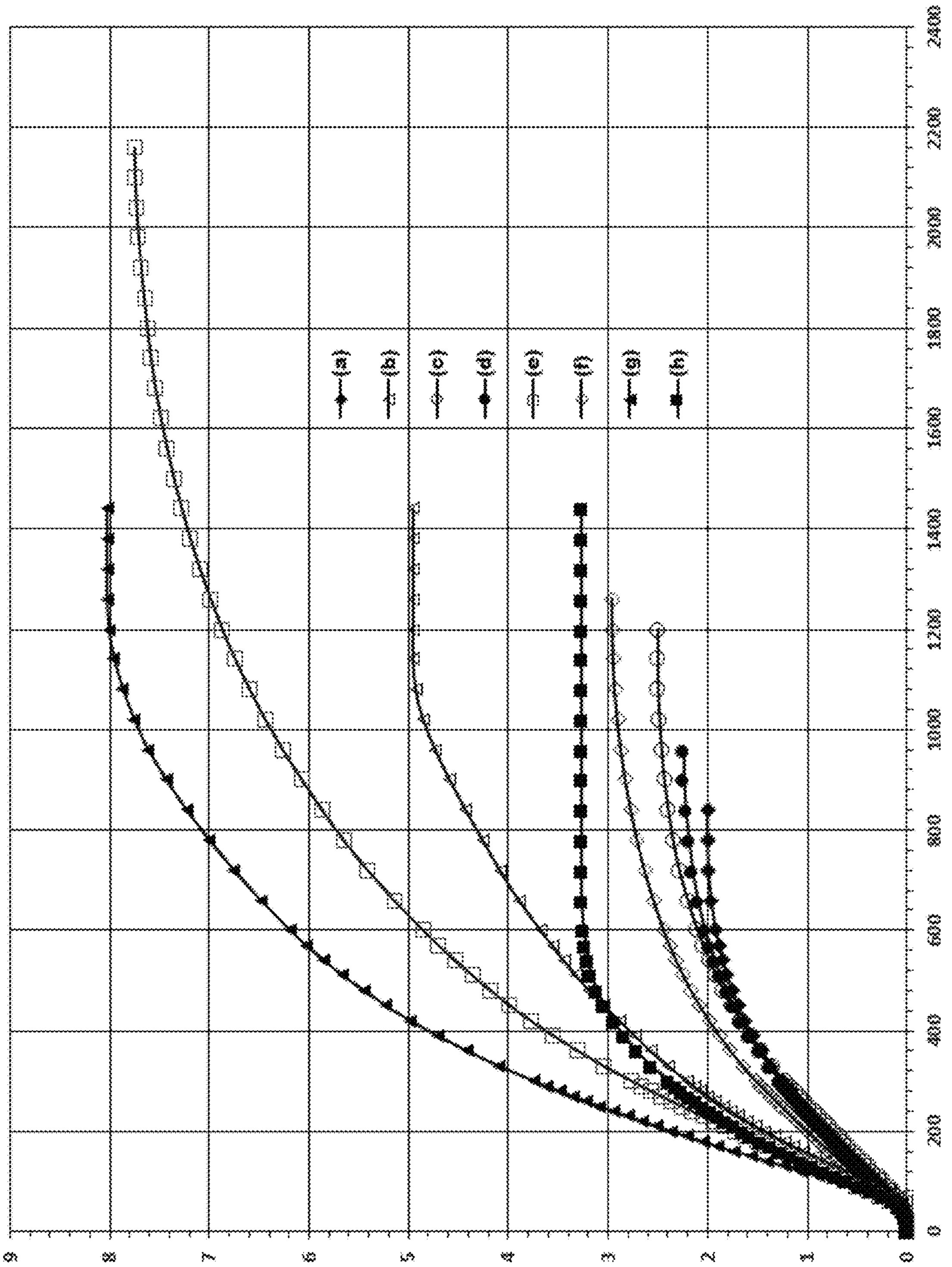
FIG. 12 is a graph that shows the amount of $NO_2$ adsorbed by raw active agents (a) NaCl (b) vitamin E (c) Ascorbic acid (d) $NaHCO_3$ (e) $CaCO_3$ (f) beta-cyclodextrin (g) $MgCO_3$ (h) ferulic acid; horizontal axis=time (sec) vertical axis=mg $NO_2$ adsorption/g active agent.
Figure 13:
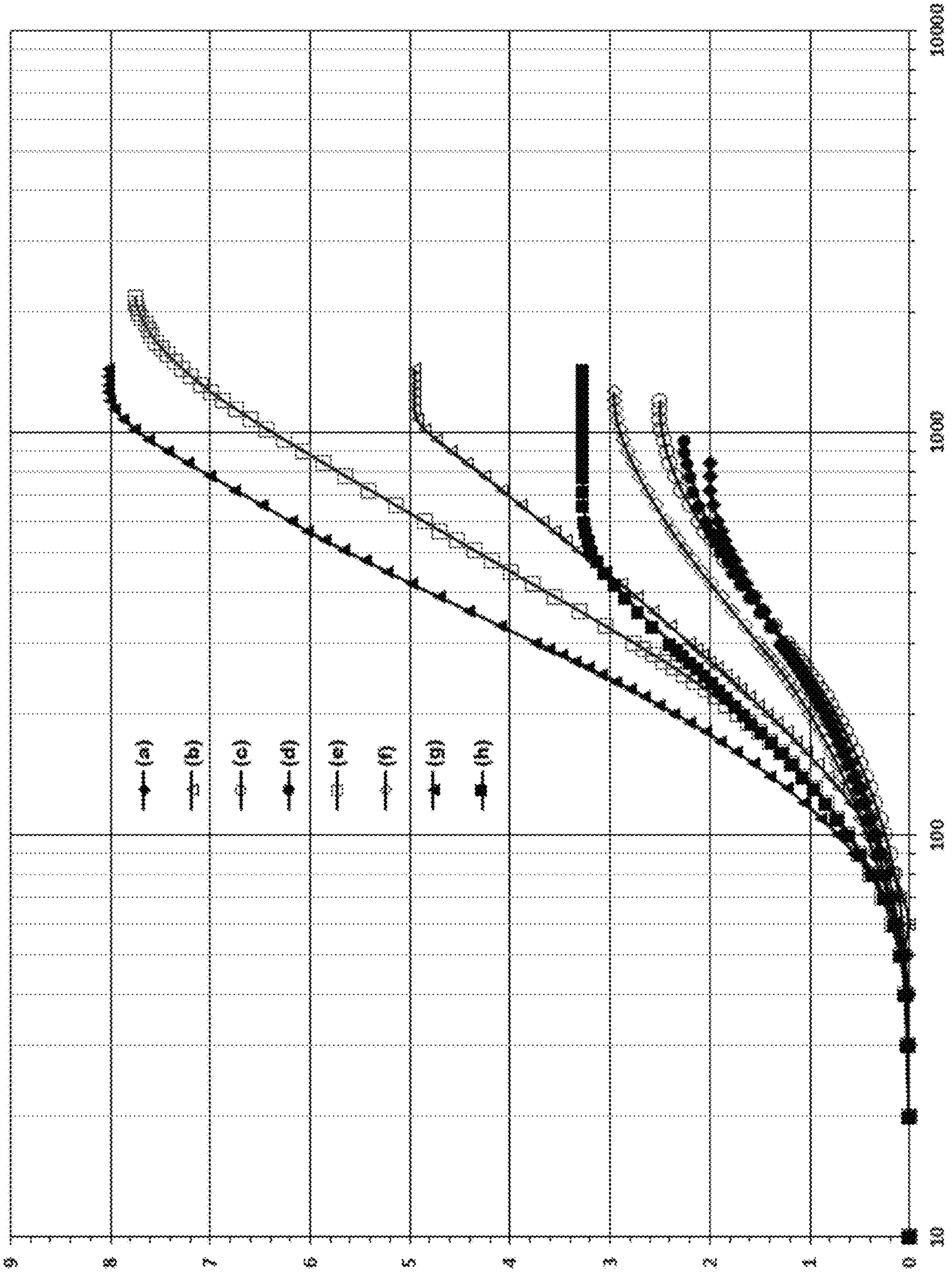
FIG. 13 is a graph that shows the amount of $NO_2$ adsorbed over log time by raw active agents (a) NaCl (b) vitamin E (c) Ascorbic acid (d) $NaHCO_3$ (e) $CaCO_3$ (f) beta-cyclodextrin (g) $MgCO_3$ (h) ferulic acid; horizontal axis=time (sec) vertical axis=mg $NO_2$ adsorption/g active agent.
Figure 14:
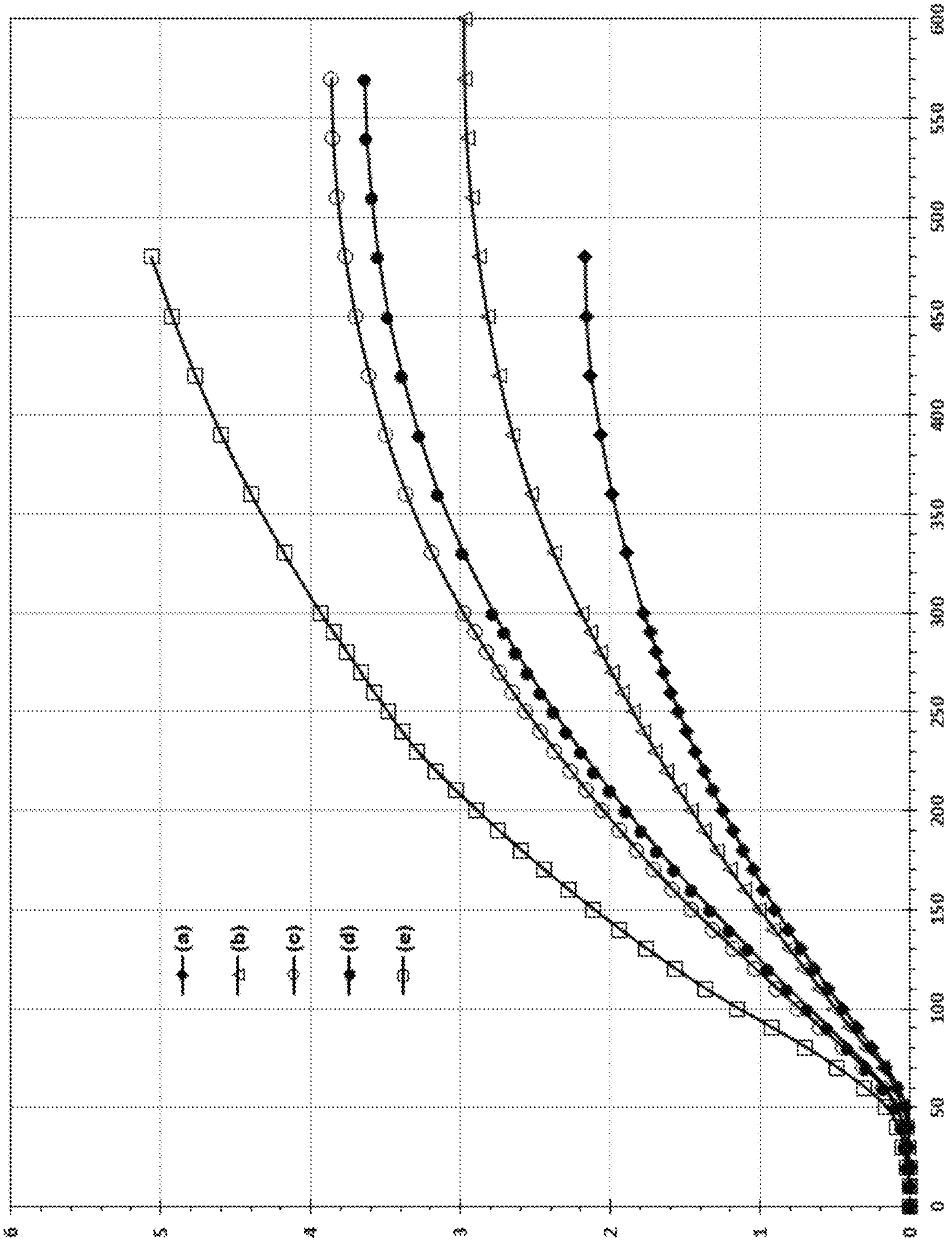
FIG. 14 is a graph that shows the amount of $NO_2$ adsorbed by films containing active agents (a) NaCl (b) vitamin E (c) Ascorbic acid "B" formulation (d) $NaHCO_3$ Sodium Bicarbonate "A" formulation (e) $CaCO_3$; horizontal axis=time (sec) vertical axis=mg $NO_2$ adsorption/g active agent.
Figure 15:
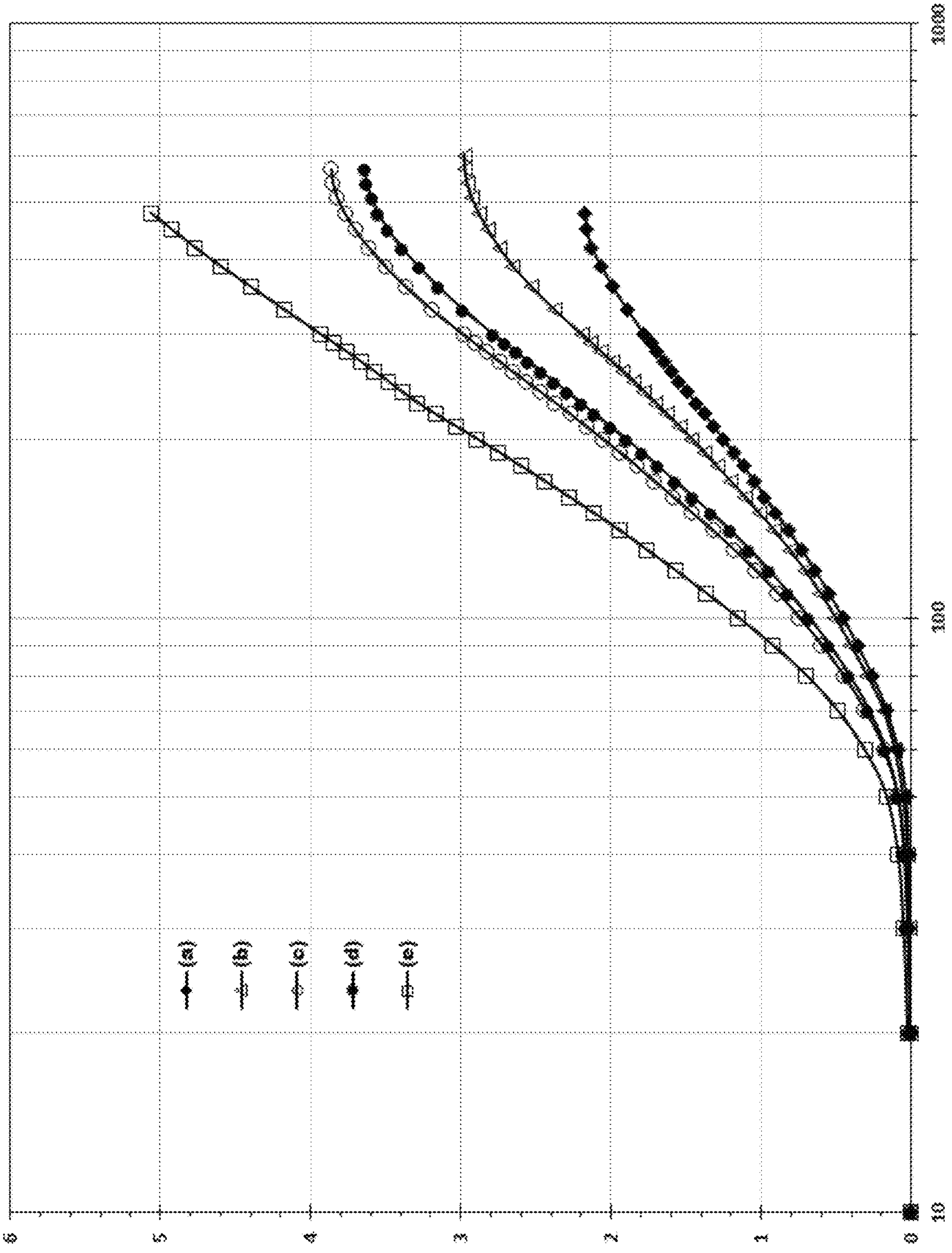
FIG. 15 is a graph that shows the amount of $NO_2$ adsorbed over log time by films containing active agents (a) NaCl (b) vitamin E (c) Ascorbic acid "B" formulation (d) $NaHCO_3$ Sodium Bicarbonate "A" formulation (e) $CaCO_3$; horizontal axis=time (sec) vertical axis=mg $NO_2$ adsorption/g active agent.
Figure 16:
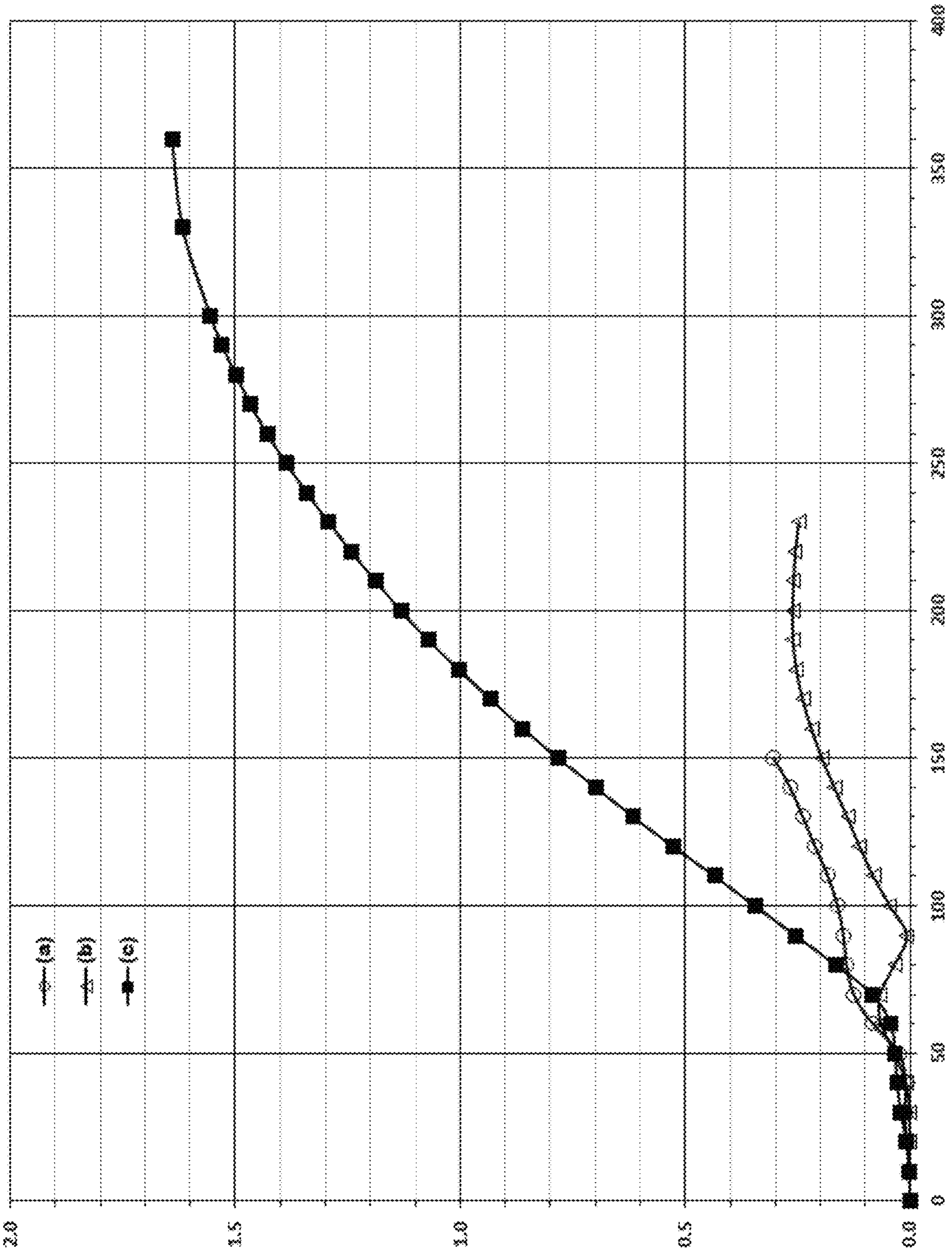
FIG. 16 is a graph that shows the amount of $NO_2$ adsorbed by virgin films (a) Film A (b) polyethylene (c) Film B, described in Table 26C; horizontal axis=time (sec) vertical axis=mg $NO_2$ adsorption/g film.

Additionally, the concentration of nitrite, in the form of nitrous acid $HNO_2$, in the headspace of each vial was analyzed after one day of aging in lab conditions at room temperature. These results are shown FIG. 4 and in Table 8.

TABLE 8

Nitrite

| Active | Nitrite (ppm) |
|---|---|
| Control | 0.76 |
| 4A | 0.52 |
| Ascorbic Acid "A" formulation | 1.19 |
| Visparent | 0.35 |
| T-AC | 0.15 |

The ascorbic acid film did not decrease the concentration of nitrite.

Example 3: Effect of Active Agent on Nitrite Concentration

A 1 inch×0.5 inch tea bag sachet containing 50 mg±2 mg of a potential active agent, or a 1 $cm^2$ film was placed hanging in a GC vial headspace. The control did not have any film in the GC vial; however, the controls for the actives did contain an empty sachet. 1 mL of 1M sulfuric acid solution and 1 mL of potassium nitrite solution (1 g/10 mL) was placed into the GC vial. The film or sachet was placed suspended inside the GC vial, and sealed, and aged for 24 hours at 60° C. GC-MS was conducted on the headspace using the derivative method. The methodology is based on a chemically derivative method that reacts all available NOx or nitrite directly into a measurable compound (cyclohexene) using acidified sodium cyclamate. The reaction is shown below:

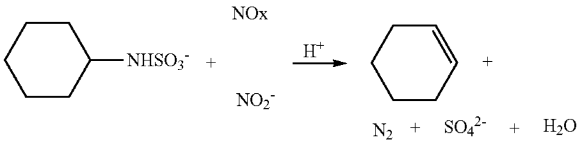

The overall methodology is outlined in "A high-throughput headspace gas chromatographic technique for the determination of nitrite content in water samples", Shu-Xin Zhang, Rong Peng, Ran Jiang, Xin-Sheng Chai, Donald G. Barnes; Journal of Chromatography A, 1538 (2018) 104-107. It will be understood that both the nitrite anion ($NO_2^-$) and nitrous anion ($HNO_2$), with the relative amounts being determined by solution pH, will be quantified by this method, and gaseous NOx can also be quantified, due to its equilibrium with aqueous phase species. For simplicity, results of this test may be described as measuring the amount of nitrite.

Results of the assay are provided in Tables 9-10.

TABLE 9

Active in Sachets Nitrite Percent Decrease

| Active | Nitrite (% decrease) |
|---|---|
| Vitamin E | 89.8 |
| Sodium Chloride | 86.8 |
| Sodium Hydroxide | 67.6 |
| Almond Flour | 66.7 |
| Potassium Hydroxide | 66.3 |
| Ferulic Acid | 61.7 |
| Walnut Powder | 59.0 |
| Sodium Bicarbonate | 57.7 |
| Flaxseed Powder | 56.7 |
| Date Seed Powder | 53.3 |
| Aloe Vera Powder | 49.8 |
| Calcium Carbonate | 46.9 |
| Zeaxanthin | 26.6 |
| Turmeric Powder | 41.6 |
| Ground Cinnamon | 39.5 |
| Anthocyanin (blueberry powder) | 37.8 |
| Coffee | 36.3 |
| Astaxanthin | 35.0 |
| Evergreen (peppermint leaves) | 34.9 |
| Magnesium Carbonate | 33.9 |
| Caffeic Acid | 31.6 |
| Dried Peppermint | 29.0 |
| Spirulina | 28.8 |
| Sodium Alginate | 27.7 |
| Beta Cyclodextrin Powder | 25.6 |
| Acai Powder | 23.9 |
| Lycopene | 23.7 |
| Ascorbic Acid | 23.7 |
| 4A Molecular Sieve | 22.6 |
| Calcium Sulfate | 22.2 |
| Green Tea Extract | 20.9 |
| Grape Seed Powder | 19.6 |
| Polyphenol (pomegranate powder) | 19.3 |

TABLE 9-continued

Active in Sachets Nitrite Percent Decrease

| Active | Nitrite (% decrease) |
|---|---|
| 13Y zeolite | 17.5 |
| Hydrochloric Acid | 14.4 |
| Ferric Oxide | 14.3 |
| Crushed Red Pepper | 14.0 |
| Pumpkin Seed Powder | 11.7 |
| Vitamin A | 11.3 |
| 3A Molecular Sieve | 9.8 |
| Barley Flour | 9.4 |
| Ground Clove | 6.3 |
| Propyl Gallate | 3.2 |
| Beta Carotene | 1.1 |
| Silica Gel | −0.5 |
| Garlic Extract | −4.6 |
| Coenzyme Q10 | −7.8 |
| Beet Root Powder | −11.6 |
| Magnesium Chloride | −15.7 |
| Olive Leaf Extract | −48.0 |

TABLE 10

Active Film Nitrite Percent Decrease

| Active | Nitrite (% decrease) |
|---|---|
| Ascorbic Acid "A" formulation | 16.3 |
| Ascorbic Acid "B" formulation | 53.4 |
| AC Film | 44.9 |
| T-AC Film | 24.7 |
| Visparent Film | 19.5 |
| Green Tea Film | 33.0 |

TABLE 11

Film Formulations

| Active | Material | Percentage in Film Formulation (wt %) | Thickness |
|---|---|---|---|
| Ascorbic Acid "A" formulation | L-Ascorbic Acid | 37 | 0.6 mm |
| | Elvax 3174 | 21 | |
| | Silica Gel Grade 11 | 15 | |
| | RESIN-3040 | 12 | |
| | Abscents 3000 | 10 | |
| | Carbowax 4000P | 5 | |
| Ascorbic Acid "B" formulation | L-Ascorbic Acid | 50 | 1.2 mm |
| | RESIN-3040 | 47 | |
| | RESIN-CARBOWAX PEG4000 SEN NF | 3 | |
| AC | AC (Chemsorb 1000-60-G5) | 35 | 0.3-0.6 mm |
| | RESIN-3040 | 64 | |
| | Carbowax | 1 | |
| T-AC | T-AC (Chemsorb 1505-60-G5) | 30 | 0.8 mm |
| | RESIN-3040 | 70 | |
| Visparent | Visparent E100 | 17 | 0.3 mm |
| | RESIN-3040 | 35 | |
| | RESIN-HD8960 | 34 | |
| | ABSCENTS 3000 | 10 | |
| | Activator CC1020014 | 3 | |
| | Eval EVOH 0738 | 1 | |
| Green Tea | Green Tea | 35 | 0.3 mm |
| | RESIN-3040 | 65 | |

Example 4: Effect of Active Agent Films on Nitrosamine and Nitrite in Blister Packs Containing Ranitidine Capsules Capsules comprising ranitidine were made using the formulation shown in the table below.

TABLE 12

| Capsule Formation | |
|---|---|
| Raw Material | Percentage by Mass (m/m) |
| Ranitidine hydrochloride | 10% |
| Microcrystalline cellulose | 41.75% |
| Lactose monohydrate | 41.75% |
| Sodium starch glycolate | 5% |
| Silicon dioxide | 0.5% |
| Magnesium stearate | 1% |

Ranitidine capsules (approximately 290 mg/capsule) were stored in blister packs made with active agent films: sodium chloride, ascorbic acid, sodium bicarbonate, vitamin E. The formulations of the films are shown in Table 21, below. The control did not have any active agent. The samples were aged at 60° C. at 40% relative humidity (RH) for 1, 4, 8, 12, 18 or 24 weeks and were assayed on a headspace using GC-MSD.

TABLE 13

Ranitidine in Blister Packs NDMA and Nitrite Week 1

| Active | NDMA (% decrease) | Nitrite (% decrease) |
|---|---|---|
| Ascorbic Acid | 59 | 15 |
| "B" formulation | | |
| Sodium Bicarbonate | 30 | 15 |
| "A" formulation | | |
| Sodium Chloride | 5 | 8 |
| Vitamin E | 30 | 14 |

TABLE 14

Ranitidine in Blister Packs NDMA and Nitrite Week 4

| Active | NDMA (% decrease) | Nitrite (% decrease) |
|---|---|---|
| Ascorbic Acid | 19 | 26 |
| "B" formulation | | |
| Sodium Bicarbonate | 29 | 7 |
| "A" formulation | | |
| Sodium Chloride | −25 | −18 |
| Vitamin E | 45 | −13 |

TABLE 15

Ranitidine in Blister Packs NDMA and Nitrite Week 8

| Active | NDMA (% decrease) | Nitrite (% decrease) |
|---|---|---|
| Ascorbic Acid | 57 | 21 |
| "B" formulation | | |
| Sodium Bicarbonate | 36 | 16 |
| "A" formulation | | |
| Sodium Chloride | 20 | −4 |
| Vitamin E | 49 | 14 |

TABLE 16A

Ranitidine in Blister Packs NDMA and Nitrite Week 12

| Active | NDMA (% decrease) | Nitrite (% decrease) |
|---|---|---|
| Ascorbic Acid | 60.33 | 29 |
| "B" formulation | | |
| Sodium Bicarbonate | 16.12 | 9 |
| "A" formulation | | |
| Sodium Chloride | 13.32 | 2 |
| Vitamin E | 35.75 | −2 |

TABLE 16B

Ranitidine in Blister Packs NDMA and Nitrite Week 18

| Active | NDMA (% decrease) | Nitrite (% decrease) |
|---|---|---|
| Ascorbic Acid | 66 | 29 |
| "B" formulation | | |
| Sodium Bicarbonate | 25 | −2 |
| "A" formulation | | |
| Sodium Chloride | −30 | 4 |
| Vitamin E | 12 | −1 |

NDMA was measured using GC-MS directly on the headspace using a calibration curve for NDMA. Nitrite was measured using the cyclohexene derivative method on the headspace.

Example 5: Effect of Raw Active on Nitrite

Raw active (50 mg) was added to a GC vial. 1 mL of 1M sulfuric acid solution and 1 mL of potassium nitrite solution (1 g/10 mL) was placed into the GC vial. The active sachet was placed inside the GC vial and sealed and aged for 24 hours at 60° C. Controls only contained the liquid. GC was conducted on the headspace using a modified version of the FDA protocol for GC-MS/MS to detect nitrite. See "Combined Headspace N-Nitrosodimethylamine (NDMA), N-Nitrosodiethylamine (NDEA), N-Nitrosoethylisopropylamine (NEIPA), and N-Nitrosodiisopropylamine (NDIPA) impurity assay by GC-MS/MS" U.S. Food & Drug Administration (FDA), Apr. 29, 2019, published online. The modified version did not use targeted analysis but used the NIST20 library match factor, and calculated an estimated ppm of nitrous acid instead.

TABLE 17

Raw Active Nitrite

| Active | Nitrite (ppm) |
|---|---|
| Control | 7.16 |
| 4A | 7.03 |
| Activated Carbon | 7.26 |
| Ascorbic Acid | 0.08 |
| Green Tea | 3.88 |

Ascorbic acid was the most effective raw active at decreasing the level of nitrite, in the form of nitrous acid, in the headspace.

Example 6: Effect of Film Comprising Active on Nitrite

Film (1 $cm^2$) comprising the active to be tested was suspended in a GC vial. The control did not have any film in the GC vial. 1 mL of 1M sulfuric acid solution and 1 mL of potassium nitrite solution (1 g/10 mL) was added to the vial. Samples were aged at 60° C. for 1 or more days as shown in Table 18. GC-MS was conducted on the headspace using the cyclohexene derivative method for nitrite.

TABLE 18

Film Nitrite Percent Decrease

| Active | Decrease (%) Day 1 | Day 3 | Day 7 |
|---|---|---|---|
| Sodium Bicarbonate "A" formulation | 90 | 99 | 100 |
| Magnesium Carbonate | 38 | N/A | 97 |
| Sodium Chloride | 63 | 40 | 97 |
| Vitamin E | 60 | 74 | 93 |

N/A: not available.

The results show that all actives tested resulted in 93% or more decrease in nitrite after 7 days. However, decrease in nitrite was seen even after only 1 day.

Statistical Testing

Film (1 $cm^2$) comprising the active to be tested was suspended in a GC vial. 1 mL of 1M sulfuric acid solution and 1 mL of potassium nitrite solution (1 g/10 mL) was added to the vial. Samples were aged at 60° C. for 7 days as shown in Table 19 below. GC-MS was conducted on the headspace using the cyclohexene derivative method for nitrite. Both the total NOx decrease, in ppm, over the 7-day period, and the average NOx decrease, in ppm, per day are provided.

Film formulations are shown in Table 21.

TABLE 19

Film Nitrite Percent Decrease and Standard Deviation

| Active | Avg % Decrease | Std. Dev. % | Count | NOx decrease (ppm/ 7 day) | NOx decrease rate (ppm/day) |
|---|---|---|---|---|---|
| Sodium Bicarbonate "A" formulation | 99.9 | 0.2 | 27 | 9.618 | 1.374 |
| Magnesium Carbonate | 68.9 | 21.08 | 29 | 6.638 | 0.948 |
| Sodium Chloride | 71.2 | 31.2 | 30 | 6.857 | 0.980 |
| Vitamin E | 91.1 | 12.1 | 30 | 8.775 | 1.254 |
| Sodium Bicarbonate "B" formulation | 98.5 | 6.0 | 30 | 9.548 | 1.364 |

The results show that all active-containing films tested resulted in 68.900 or more decrease in nitrite after 7 days.

Example 7: Film and Sachet Comparison in Monolayer Bottles

Raw actives and films were prepared as shown in the table below.

TABLE 20

Film and Sachet Actives

| Active | Percentage in Film Formulation (wt %) | Mass for Testing (g) |
|---|---|---|
| Sodium Chloride | 50 | 1.8 |
| Ascorbic Acid | 50 | 4.9 |
| Sodium Bicarbonate | 60 | 2.2 |
| Vitamin E | 55.3 | 1.5 |
| Activated Carbon | 30 | 0.6 |

For raw active samples, the appropriate mass was weighed as shown in Table 20 and was placed in a sachet which was closed. Films were cut to 120 mm×65 mm. Film thickness was from about 0.3 mm to about 1.2 mm. Film formulations are shown in the table below. The control did not have any sachet or film in the bottle.

TABLE 21

Film Formulations

| Active | Material | Percentage in Film Formulations (wt %) | Thickness |
|---|---|---|---|
| Sodium Chloride | NaCl | 50 | 0.3-0.8 mm |
| | RESIN-3040 | 47 | |
| | RESIN-CARBOWAX PEG4000 SEN NF | 3 | |
| Ascorbic Acid "B" formulation | L-Ascorbic Acid | 50 | 0.8-1.2 mm |
| | RESIN-3040 | 47 | |
| | RESIN-CARBOWAX PEG4000 SEN NF | 3 | |
| Sodium Bicarbonate "A" formulation | $NaHCO_3$ | 60 | 0.3-0.8 mm |
| | RESIN-3040 | 37 | |
| | RESIN-CARBOWAX PEG4000 SEN NF | 3 | |
| Vitamin E | Vitamin E | 55.29 | 0.3-0.8 mm |
| | RESIN-3040 | 14.12 | |
| | RESIN-CARBOWAX PEG4000 SEN NF | 5.88 | |
| | EVA-2528 | 24.71 | |
| Activated Carbon | Activated Carbon | 30 | 0.3-0.6 mm |
| | RESIN-3040 | 70 | |
| Magnesium Carbonate | $MgCO_3$ (Anhydrous) | 60 | 0.3 mm |
| | RESIN-3040 | 37 | |
| | RESIN-CARBOWAX PEG4000 SEN NF | 3 | |
| Sodium Bicarbonate "B" formulation | $NaHCO_3$ | 60 | 0.33 mm |
| | LDPE 2692 | 35 | |
| | EVA-2528 | 5 | |
| Calcium Carbonate | CaCO3 | 60 | 0.33 mm |
| | LDPE 2692 | 35 | |
| | EVA-2528 | 5 | |

A 20 mL scintillation vial was placed in each bottle. 3.5 mL of potassium nitrite and 3.5 mL of sulfuric acid were added to the scintillation vial. GC-MS was conducted on the headspace using the cyclohexene derivative method for nitrite. Samples were aged at 60° C. and 40% RH for 6 days.

TABLE 22

Raw Active Nitrite Percent Decrease

| Active | Nitrite (% Decrease) |
|---|---|
| Ascorbic Acid | −111.1 |
| Activated Carbon | −13.1 |
| Sodium Bicarbonate | 72.8 |
| Sodium Chloride | 99.9 |
| Vitamin E | 31.6 |

Sodium chloride and sodium bicarbonate raw actives in sachets decreased nitrite by more than 70%.

Without wishing to be bound by theory, the increase in nitrite shown in some instances, such as in Tables 22 and 23, for ascorbic acid may be due to nitrosation of the ascorbic acid.

TABLE 23

| Film with Active Nitrite Percent Decrease | |
|---|---|
| Active | Nitrite (% Decrease) |
| Ascorbic Acid "B" formulation | −102.1 |
| Activated Carbon | 12.4 |
| Sodium Bicarbonate "A" formulation | 69.4 |
| Sodium Chloride | 100 |
| Vitamin E | 67.5 |

The results showed that films decreased more nitrite than raw active sachets.

Example 8: Blow-Molded Bottles

Blow-molded bottles were made with each active: calcium carbonate, sodium bicarbonate, sodium chloride, AC, T-AC, Visparent and Visparent without inside liner, as described in Example 1. A 20 mL scintillation vial was placed in each bottle. 4.25 mL of potassium nitrite and 4.25 mL of sulfuric acid were added to the scintillation vial. Samples were aged at room temperature for 1 week at 100% RH. GC-MS was conducted on the headspace using the cyclohexene derivative method for nitrite.

TABLE 24

| Blow-molded Bottles with Active Nitrite Percent Decrease | |
|---|---|
| Active | Nitrite (% Decrease) |
| Sodium Bicarbonate | 99.6 |
| Sodium Chloride | 55.1 |
| AC | 26.8 |
| T-AC | 33.1 |
| Visparent | −129 |
| Visparent without inside liner | −52.3 |

The results showed that sodium bicarbonate blow-molded bottles decreased nitrite by 99.6% and sodium chloride blow-molded bottles decreased nitrite by 55.1%.

Example 9: NO and $NO_2$ Adsorption by Raw Active and Film

NO and $NO_2$ adsorption experiments were conducted within a fixed bed reactor at 22° C. In each experimental run, 250 mg of the sample was meticulously deposited onto a fused silica frit positioned within a vertical quartz reactor, which boasted an internal diameter of 6 mm. Prior to each experiment, the system underwent a thorough purge using nitrogen (N) to eliminate any residual gases and ensure a clean starting point. Following the purge, calibration procedures were meticulously carried out to guarantee the accuracy of the concentration measurements. This involved precisely calibrating the ROSEMOUNT NGA 2000 detector to establish a reliable baseline for the subsequent experiments. The experimental setup involved injecting a gas containing 505 ppm of $NO_2$ through the fixed bed column of the sample. To maintain consistent conditions, a constant gas flow rate of 50 NL $h^{-1}$ was carefully controlled using BROOKS 5850 mass flow controllers sourced from Seattle, WA, USA. Throughout the experiments, the concentrations of outlet gases, namely NO and $NO_2$, were continuously monitored. This real-time analysis was facilitated by the highly sensitive ROSEMOUNT NGA 2000 detector (St. Louis, MO, USA). To account for any background signals or potential interferences, a blank experiment was conducted using an empty reactor. The obtained results from this blank experiment were subtracted from the measurements of the sample, ensuring that the recorded concentrations accurately reflected the adsorption behavior of $NO_2$ by the sample. This meticulous approach enhances the reliability and precision of the experimental findings.

TABLE 25

| Raw Active NO and $NO_2$ Adsorption | | |
|---|---|---|
| Active | NO Adsorbed Amount (mg/g) | $NO_2$ Adsorbed Amount (mg/g) |
| Sodium Chloride | 0.34 | 2.00 |
| Ascorbic Acid | 0.14 | 2.50 |
| Beta-Cyclodextrin | N/A | 2.96 |
| Sodium Bicarbonate | 0.14 | 2.24 |
| Calcium Carbonate | 0.15 | 7.75 |
| Magnesium Carbonate | N/A | 8.03 |
| Vitamin E | 0.16 | 4.95 |
| Ferulic Acid | N/A | 3.27 |

N/A: not available

TABLE 26A

| Film NO Adsorption | | | |
|---|---|---|---|
| Active | Total NO Adsorbed Amount (mg NO/g of film) | NO adsorbed corrected after removal of polymer contribution (mg $NO_2$/g of film) | NO adsorbed per grams of active materials present in films (mg $NO_2$/g of active material in film) |
| Sodium Chloride | 0.28 | 0.21 | 0.42 |
| Vitamin E | 0.22 | 0.16 | 0.28 |
| Ascorbic Acid "B" formulation | 0.10 | 0.03 | 0.06 |
| Sodium Bicarbonate "A" formulation | 0.35 | 0.29 | 0.49 |
| Sodium Bicarbonate "B" formulation | N/A | N/A | N/A |
| Calcium Carbonate | 0.43 | 0.43 | 0.72 |
| No Active in film A | 0.14 | — | — |
| No Active in film B | 0.00 | — | — |

N/A: not available

TABLE 26B

| Film $NO_2$ Adsorption | | | |
|---|---|---|---|
| Active | Total $NO_2$ Adsorbed Amount (mg $NO_2$/g of film) | $NO_2$ adsorbed corrected after removal of polymer contribution (mg $NO_2$/g of film) | $NO_2$ adsorbed per grams of active materials present in films (mg $NO_2$/g of active material in film) |
| Sodium Chloride | 2.17 | 2.03 | 4.07 |
| Vitamin E | 2.97 | 2.24 | 4.05 |
| Ascorbic Acid "B" formulation | 3.86 | 3.72 | 7.45 |
| Sodium Bicarbonate "A" formulation | 3.64 | 3.53 | 5.89 |
| Sodium Bicarbonate "B" formulation | 2.42 | N/A | N/A |
| Calcium Carbonate | 5.49 | 4.06 | 8.06 |
| No Active in film A | 0.27 | — | — |
| No Active in film B | 1.64 | — | — |
| No Active in film C | 0.25 | — | — |

N/A: not available

TABLE 26C

| Formulations of Films Without Active | | |
|---|---|---|
| Name | Material | Percentage in Film Formulation (wt %) |
| Film A | RESIN-3040 | 97 |
| | RESIN-CARBOWAX PEG4000 SEN NF | 3 |
| Film B | RESIN-3040 | 97 |
| | EVA-2528 | 3 |
| Film C | Polyethylene | 100 |

Films shown in Tables 26A-B with active correspond to those in Table 21, above. Films shown in Tables 26A-B without active correspond to those in Table 26C. The results show that calcium carbonate was the most effective $NO_2$ adsorber from amongst the raw actives tested, and ascorbic acid was the most effective film tested. The results also show that for a specific active, the film with active was more effective than the raw active, when correcting for any contribution made by the film itself, and when corrected for grams of active.

Without wishing to be bound by theory, the additional porosity generated by the presence of active material in the polymer matrix may be used as a reservoir for additional NO or $NO_2$ scavenging. Another possibility is that the active materials in contact with the polymer matrix create another species which possesses higher scavenging capacities for NO and $NO_2$ than the raw active. A third possibility is that the active material may be more preserved in the polymer matrix than in raw form. A combination of any of these possibilities may also be envisaged.

FIGS. 5-16 are graphs that show NO and $NO_2$ adsorption results with raw active, film with active, or virgin film.

Example 10: Excipient Tablets without API

Excipient tablets without API were used to test actives. The tablets contain approximately 66% microcrystalline cellulose (MCC), which is a source of nitrite. MCC and lactose are mixed in a 2:1 ratio with small levels of lubricant as required for manufacture.

Three MCC tablets with or without film (2×2 inch) were added to a 2.5×2.5 inch foil bag and sealed. Samples were aged at 60° C. for 6 days with or without film. GC-MS was conducted on the headspace using the derivative method. Results of the assay are provided in Table 27 below.

TABLE 27

| Absorption of Nitrite Released by Excipient Tablets Without API | | | | | | |
|---|---|---|---|---|---|---|
| Film Tested | Response | Avg PPM | % Decrease | PPM Std Dev | % Std Dev | Count |
| Control | 3867357 | 53.5 | | 33.23 | | 10 |
| Ascorbic Acid "B" formulation | 978644 | 13.3 | 75.1 | 19.73 | 36.88 | 12 |
| AC | 659594 | 8.9 | 83.4 | 6.35 | 11.88 | 14 |
| Visparent | 1182109 | 16.2 | 69.8 | 1.63 | 3.05 | 15 |
| Vitamin E | 1176091 | 16.1 | 69.9 | 2.14 | 4.00 | 12 |

Results shown in Table 27 indicate that Ascorbic Acid film resulted in a decrease of 75.1% in nitrite, Activated Carbon film resulted in a decrease of 83.4% in nitrite, Visparent film resulted in a decrease in 69.8% in nitrite and Vitamin E film resulted in a decrease in 69.9% in nitrite.

Example 11: Foil Bag, Drop-In and Blown Bottle (Blow-Molded Bottle) Studies with Ranitidine Ranitidine capsules were used to test Actives. The capsules contain ranitidine hydrochloride (same capsules used in Example 4), MCC, lactose monohydrate, sodium starch glycolate, silicon dioxide and magnesium stearate.

Foil Bag

Two ranitidine capsules with or without film (2×2 inch) were added to a 3×3 inch foil bag containing filter paper impregnated with 0.5 mL of water and sealed. Samples were aged at 60° C. for 7 days with or without film. GC-MS was conducted on the headspace using the derivative method. Results of the assay are provided in Table 28 below.

TABLE 28

| Film Nitrite Percent Decrease and Standard Deviation | | | | |
|---|---|---|---|---|
| Active | % Reduction | Count | Std Dev | Std Dev % |
| Ascorbic Acid "B" formulation | 82.8 | 9 | 5.62 | 6.8 |
| Sodium Bicarbonate "A" formulation | −84.2 | 10 | 92.10 | −109.4 |
| Sodium Chloride | 47.5 | 10 | 23.06 | 48.5 |
| Vitamin E | 35.4 | 9 | 34.26 | 96.7 |
| Sodium Bicarbonate "B" formulation | −21.3 | 10 | 64.91 | −304.7 |

Results shown in Table 28 indicate that Ascorbic Acid film resulted in a decrease of 82.8% in nitrite, Sodium Chloride film resulted in a decrease of 47.5% in nitrite, and Vitamin E film resulted in a decrease in 35.4% in nitrite.

TABLE 29

| Film NDMA Percent Decrease and Standard Deviation | | | | |
|---|---|---|---|---|
| Active | % Reduction | Count | Std Dev | Std Dev % |
| Ascorbic Acid "B" formulation | 83.7 | 10 | 7.26 | 8.7 |
| Sodium Bicarbonate "A" formulation | 56.7 | 10 | 41.85 | 73.8 |
| Sodium Chloride | −70.9 | 10 | 67.23 | −94.9 |
| Vitamin E | 10.4 | 10 | 42.10 | 404.9 |
| Sodium Bicarbonate "B" formulation | 66.9 | 10 | 23.59 | 35.3 |

Results shown in Table 29 indicate that Ascorbic Acid film resulted in a decrease of 83.7% in NDMA, Sodium Bicarbonate "A" formulation film resulted in a decrease of 56.7% in NDMA, Vitamin E film resulted in a decrease in 10.4% in NDMA, and Sodium Bicarbonate "B" formulation film resulted in a decrease of 66.9% in NDMA.

Drop-In

Twenty-five ranitidine capsules with or without film (2×2 inch) were added to a bottle containing a suspended water impregnated sponge (1×1 cm) and sealed. Samples were aged at approx. 22° C. for 4 weeks at 100% RH with or without film. 4 capsules from each bottle were tested: 2 for nitrite testing and 2 for NDMA testing.

GC-MS was conducted on the headspace using the derivative method for nitrite. Results of the assay are provided in Table 30 below.

TABLE 30

Film Nitrite Percent Decrease and Standard Deviation

| Active | % Reduction | Count | Std Dev | Std Dev % |
|---|---|---|---|---|
| Ascorbic Acid "B" formulation | −6.96 | 5 | 44.20 | −635.2 |
| Sodium Bicarbonate "A" formulation | 11.92 | 5 | 40.57 | 340.3 |
| Sodium Chloride | 15.80 | 5 | 44.44 | 281.3 |
| Vitamin E | −0.37 | 5 | 42.68 | −11477.4 |
| Sodium Bicarbonate "B" formulation | −10.70 | 5 | 42.26 | −395.0 |

Results shown in Table 30 indicate that Sodium Bicarbonate "A" formulation film and Sodium Chloride film reduced Nitrite by 11.92% and 15.80% respectively.

Blown Bottle (Blow-Molded Bottle)

Twenty-five ranitidine capsules were added to a bottle made with or without active, containing a suspended water impregnated sponge (1×1 cm) and sealed. Samples were aged at approx. 22° C. (room temperature) at 100% RH for 6 weeks. 1 capsule from each bottle was tested for nitrite and 1 capsule from each bottle was tested for NDMA.

GC-MS was conducted on the headspace using the derivative method for nitrite. GC-MS was conducted on the headspace for NDMA. Results of the assay are provided in Tables 31 and 32 below.

TABLE 31

Blown Bottle Nitrite Percent Decrease and Standard Deviation

| Active | % Reduction | Count | Std Dev | Std Dev % |
|---|---|---|---|---|
| Sodium Chloride | −47.81 | 5 | 26.97 | −56 |
| Calcium Carbonate I* | −45.47 | 5 | 32.79 | −72 |
| Sodium Bicarbonate | 0.89 | 5 | 24.81 | 2781 |

*See Example 12, Table 33C

TABLE 32

Blown Bottle NDMA Percent Decrease and Standard Deviation

| Active | % Reduction | Count | Std Dev | Std Dev % |
|---|---|---|---|---|
| Sodium Chloride | −15.67 | 5 | 40.64 | −259 |
| Calcium Carbonate I* | −7.26 | 5 | 34.01 | −469 |
| Sodium Bicarbonate | 13.69 | 5 | 21.44 | 157 |

*See Example 12, Table 33C

Results shown in Table 31 indicate that Sodium Bicarbonate blown bottles reduced nitrite by 0.89%. Results shown in Table 32 indicate that Sodium Bicarbonate reduced NDMA by 13.69%. Without wishing to be bound by theory, lack of success by blown bottles with Calcium Carbonate I formulation at decreasing nitrite or NDMA may be explained by their pre-blending (i.e., being formed in a masterbatch) before being compounded and extruded. The pre-blending may have diminished the effectiveness of the Calcium Carbonate.

Example 12: Blown Bottle (Blow-Molded Bottle)-Short Term Studies 4.25 mL of 1M sulfuric acid solution and 4.25 mL of potassium nitrite solution (1 g/10 mL) was placed into the GC vial. No ranitidine capsules were included in the blown bottle short-term studies. Samples were aged at approx. 22° C. for 7 days.

GC-MS was conducted on the headspace using the derivative method for nitrite. Results of the assay are provided in Tables 33A and 33B below. Formulations for Calcium Carbonate I and Calcium Carbonate II blown bottles are shown in Table 33C.

TABLE 33A

Blown Bottle Nitrite Percent Decrease and Standard Deviation

| Active | % Reduction | Count | Std Dev | Std Dev % |
|---|---|---|---|---|
| Calcium Carbonate I | −12.6 | 13 | 50.82 | −402.4 |
| Sodium Bicarbonate | 99.6 | 14 | 0.19 | 0.2 |
| Sodium Chloride | 51.1 | 14 | 58.29 | 114.2 |

TABLE 33B

Blown Bottle Nitrite Percent Decrease and Standard Deviation

| Active | % Reduction | Count | Std Dev | Std Dev % |
|---|---|---|---|---|
| Ascorbic Acid | −27 | 7 | 36.32 | −135 |
| Calcium Carbonate II | 54 | 7 | 9.34 | 17 |
| Vitamin E | 99 | 7 | 1.04 | 1 |

TABLE 33C

Blown Bottle Formulations Calcium Carbonate

| Formula | Base Polymer | Active | Channeling Agent |
|---|---|---|---|
| Calcium Carbonate I | 20 LDPE 2692 | 75 Masterbatch* | 5 EVA-2528 |
| Calcium Carbonate II | 20, Exact 3040 | 75 | 5 PEG Carbowax 4000 SEN NF |

*Masterbatch: PC81, PC81-1 (PlastiCal, Alabama)

Results shown in Table 33A indicate that Sodium Bicarbonate blown bottles reduced nitrite by 99.6% and Sodium Chloride blown bottles reduced nitrite by 51.1%. Results shown in Table 33B indicate that Calcium Carbonate II blown bottles reduced nitrite by 54% and Vitamin E blown bottles reduced nitrite by 99%.

Example 13: Blown Film Nitrite Studies 500 mg of blown film was suspended above 2 ml nitrous acid solution in a GC vial and was aged for 7 days at 60° C.

Blown film formulations are provided below:

TABLE 34

| Blown Film Formulations | |
|---|---|
| Composition | Extrusion parameters |
| L-Ascorbic Acid 50% | 80 rpm |
| RESIN-CARBOWAX PEG4000 SEN NF 3% | 255 extrusion temperature 255° F. |
| RESIN-3040 47% | 270 melt temperature 270° F.<br>1300 rpm cool air flow |
| Sodium Chloride 60% | 55 rpm |
| LDPE 2692 35% | melt temperature 270° F. |
| EVA-2528 5% | extrusion temperature 255° F.<br>1300 rpm air flow |
| Sodium Bicarbonate 60% | 75 rpm |
| LDPE 2692 35% | 270F extrusion temperature 270° F. |
| EVA-2528 5% | 302F melt temperature 302° F.<br>1300 rpm cool air flow. |

GC-MS was conducted on the headspace using the derivative method. Results of the assay are provided in Table 35 below.

TABLE 35

| Blown Film Nitrite Percent Decrease and Standard Deviation | | | | |
|---|---|---|---|---|
| Active | % Reduction | Count | Std Dev | Std Dev % |
| Ascorbic Acid | 82.3 | 14 | 13.7 | 17 |
| Sodium Chloride | 74.8 | 14 | 15.3 | 21 |
| Sodium Bicarbonate | 99.0 | 13 | 1.4 | 1 |

Results shown in Table 35 indicate that Ascorbic Acid blown film resulted in a decrease of 82.3% in nitrite, Sodium Chloride blown film resulted in a decrease of 74.8% in nitrite, and Sodium Bicarbonate blown film resulted in a decrease in 99.0% in nitrite.

Example 14: Raw Active and Film Studies with Propranolol

Raw active or film with active were tested in 250 ml bottles with 1 g of propranolol (beads), to measure formation of Nitroso-propranolol (NPO). When present, the film (2 pieces of A2×2 inches) was wrapped inside bottle(s). Raw active (5 g) was placed in a pouch inside bottle(s).

Aging was conducted at 50° C./75% RH for 4 weeks.

Humidity was provided by vials containing a salt solution: ASAPprime™ vials (FreeThink Technologies, Branford CT, USA). A screw cap was used, with no induction seal.

NPO was directly measured by LC-MS (liquid chromatography-mass spectroscopy). The detection limit is approximately 1% of the results reported.

TABLE 36

| Raw Active NPO Percent Decrease | |
|---|---|
| Active | NPO (% Decrease) |
| Ascorbic Acid | 9 |
| Sodium Ascorbate | 9 |
| L-cysteine | 2 |
| 4-aminobenzonic acid | 7 |

Ascorbic Acid and Sodium Ascorbate raw actives in sachets decreased NPO by 9%.

TABLE 37

| Film with Active NPO Percent Decrease | |
|---|---|
| Active | NPO (% Decrease) |
| Vitamin E | −4 |
| Sodium Bicarbonate “A” formulation | 19 |
| Sodium Chloride | 5 |
| Magnesium Carbonate | 3 |
| Ascorbic Acid | 28 |
| Visparent | 24 |

The results showed that films decreased NPO more than raw active sachets. Ascorbic Acid film (corresponding to 1.722 g total Ascorbic Acid) decreased NPO by 28%, whereas raw Ascorbic Acid (5 g) decreased NPO by 9%. Decreasing the amount of Ascorbic Acid by roughly a factor of three going from raw to film format resulted in a threefold increase in the effectiveness of NPO adsorption. The overall effect is thus roughly a ninefold increase in effectiveness of the film when compared to the raw active.

Example 15: Phenylephrine Capsules in Blisters

Phenylephrine Capsules

Capsules comprising phenylephrine were made using the formulation shown in the table below.

TABLE 38

| Phenylephrine Capsule Formulation | |
|---|---|
| Raw Material | Percentage by Mass (m/m) |
| Phenylephrine tablet powder | 99.95% |
| Sodium nitrite | 0.05% |

Phenylephrine tablet powder was obtained from purchased phenylephrine HCl tablets (10 mg) (Gencare, New Brunswick NJ, US).

Phenylephrine capsules (approximately 540 mg/capsule) were stored in blister packs made with active agent films: Tris-Activated Carbon, Ascorbic Acid, Sodium Bicarbonate, Vitamin E. The formulations of the films are shown in Table 21, above. The control did not have any active agent. The samples were aged at 60° C. at 40% RH humidity for 4 or 12 weeks and were assayed on a headspace using GC-MSD. Aging for 4 weeks at 60° C. at 40% RH humidity is predictive of 1 year at 23° C. Aging for 12 weeks at 60° C. at 40% RH humidity is predictive of 3 years at 23° C. See ASTM standard F1980-21, available at astm.org/f1980-21.

A calibration curve was created for N-nitroso-phenylephrine (NNP) using LC-QTOF.

Nitrite was measured using the derivative method on the headspace using GC.

TABLE 39A

| Phenylephrine in Blister Packs NNP Week 4 | | | | |
|---|---|---|---|---|
| Active | NNP (ppm) | % Decrease NNP | Std Dev | Std Dev % |
| Control | 76.97 | — | 35 | 45 |
| Ascorbic Acid "B" formulation | 73.68 | 4 | 36 | 49 |
| Sodium Bicarbonate "A" formulation | 54.31 | 29 | 26 | 48 |
| Tris-Activated Carbon | 50.69 | 34 | 20 | 39 |
| Vitamin E | 55.09 | 28 | 20 | 36 |

Results show that use of Sodium Bicarbonate "A" formulation film resulted in a 29% decrease, Tris-Activated Carbon film resulted in 34% decrease, and Vitamin E film resulted in 28% decrease of NNP formed.

TABLE 39B

| Phenylephrine in Blister Packs NNP Week 12 | | | | |
|---|---|---|---|---|
| Active | NNP (ppm) | % Decrease NNP | Std Dev | Std Dev % |
| Control | 60.99 | — | 31 | 50 |
| Ascorbic Acid "B" formulation | 50.00 | 18 | 21 | 41 |
| Sodium Bicarbonate "A" formulation | 66.08 | −8 | 26 | 39 |
| Tris-Activated Carbon | 40.67 | 33 | 53 | 131 |
| Vitamin E | 31.62 | 48 | 32 | 72 |

Results show that use of Tris-Activated Carbon film resulted in 33% decrease, and Vitamin E film resulted in 48% decrease of NNP formed.

TABLE 39C

| Phenylephrine in Blister Packs Nitrite Week 12 | | | | |
|---|---|---|---|---|
| Active | NNP (ppm) | % Decrease NNP | Std Dev | Std Dev % |
| Control | 0.92 | — | 0.51 | 55 |
| Ascorbic Acid "B" formulation | 0.94 | −2 | 0.19 | 20 |
| Sodium Bicarbonate "A" formulation | 0.74 | 20 | 0.03 | 4 |
| Tris-Activated Carbon | 1.46 | −62 | 0.56 | 39 |
| Vitamin E | 0.69 | 25 | 0.12 | 18 |

Results show that use of Sodium bicarbonate "A" formulation film resulted in 20% decrease, and Vitamin E film resulted in 2500 decrease of Nitrite formed.

Example 16: Modified Dry Excipient Tablets

Modified dry excipient tablets were prepared as outlined below.

TABLE 40A

| Tablet Dedication by Time Point | | | |
|---|---|---|---|
| | Formulation | Quantity/Time Point | |
| Tablet Formulation Drug | ID | Week 0 | Week 12 |
| Ranitidine Hydrochloride | 1A | 5 | 21 |
| 4-Phenylpiperidine Hydrochloride | 2A | 5 | 21 |
| 4-Hydroxy-4-Phenylpiperidine | 3A | 5 | 21 |
| 4-Hydroxy-4-Phenylpiperidine Hydrochloride | 4A | 5 | 21 |
| Ranitidine Hydrochloride spiked with Sodium Nitrite | 1B | 5 | 21 |
| 4-Phenylpiperidine Hydrochloride spiked with Sodium Nitrite | 2B | 5 | 21 |
| 4-Hydroxy-4-Phenylpiperidine spiked with Sodium Nitrite | 3B | 5 | 21 |
| 4-Hydroxy-4-Phenylpiperidine Hydrochloride spiked with Sodium Nitrite | 4B | 5 | 21 |
| Total | | 40 | 168 |

TABLE 40B

| Compositions (g) Formulations 1A, 1B, 2A and 2B | | | | |
|---|---|---|---|---|
| Component | Formulation 1A | Formulation 1B | Formulation 2A | Formulation 2B |
| Ranitidine hydrochloride | 4.4890 | 4.4909 | — | — |
| 4-phenylpiperdine hydrochloride | — | — | 4.5012 | 4.5075 |
| Microcrystalline cellulose (MCC) | 18.7916 | — | 18.7872 | — |
| MCC spiked with 0.0024% sodium nitrite | — | 18.8385 | — | 18.6777 |
| Lactose monohydrate | 18.7867 | 18.7887 | 18.7905 | 18.7714 |
| Sodium starch glycolate | 2.2595 | 2.2508 | 2.2511 | 2.2596 |

TABLE 40B-continued

| Compositions (g) Formulations 1A, 1B, 2A and 2B | | | | |
|---|---|---|---|---|
| Component | Formulation 1A | Formulation 1B | Formulation 2A | Formulation 2B |
| Silicon dioxide | 0.2265 | 0.2247 | 0.2265 | 0.2257 |
| Magnesium stearate* | 0.4374 | 0.4343 | 0.4312 | 0.4311 |

*Quantities of magnesium stearate were calculated based upon actual yield of screened dried granulate

TABLE 40C

| Compositions (g) Formulations 3A, 3B, 4A and 4B | | | | |
|---|---|---|---|---|
| Component | Formulation 3A | Formulation 3B | Formulation 4A | Formulation 4B |
| 4-phenylpiperdin-4-ol free base | 9.9046 | 9.9398 | — | — |
| 4-phenylpiperdin-4-ol hydrochloride | — | — | 12.6208 | 12.6270 |
| Microcrystalline cellulose (MCC) | 25.7410 | 25.8225 | 26.6818 | 26.8222 |
| Lactose monohydrate | 25.8603 | 25.8450 | 26.7984 | 26.7853 |
| Calcium phosphate dibasic | 25.8787 | 25.9376 | 26.5642 | 26.5539 |
| Sodium starch glycolate | 4.4655 | 4.4837 | 4.6634 | 4.6625 |
| Polyvinylpyrrolidone | 4.4839 | 4.4714 | 4.6202 | 4.6375 |
| Silicon dioxide | 0.9029 | 0.8888 | 0.9326 | 0.9267 |
| Magnesium stearate* | 0.8707 | 0.8888 | 0.9006 | 0.8963 |
| Sodium stearyl fumarate* | 0.8781 | 0.8844 | 0.9053 | 0.9087 |
| Sodium nitrite | — | 0.0495 | — | 0.0526 |

*Quantities of magnesium stearate and sodium stearyl fumarate were calculated based upon actual yield of screened dried granulate.

Maximum daily dose (MVID) for each drug and acceptable intake (AI) for each nitrosamine formed by each drug is shown in Table 40D below.

TABLE 40D

| MDD and AI | |
|---|---|
| Ranitidine | |
| AI NDMA/day | 96 ng |
| MDD | 320 mg |
| AI (ppm) | 0.3 ppm |
| Phenylephrine | |
| AI 1-nitroso-phenylephrine/day | 100 ng |
| MDD | 60 mg |
| AI (ppm) | 1.67 ppm |
| 4-Phenylpiperdine (CPCA Calculated) | |
| AI 1-nitroso-4-phenylpiperdine/day | 400 ng |
| MDD (pethidine) | 400 mg |
| AI (ppm) | 1 ppm |
| 4-Phenylpiperdine (CPCA Calculated) | |
| AI 1-nitroso-4-phenylpiperdine/day | 400 ng |
| MDD (meperide) | 600 mg |
| AI (ppm) | 0.67 ppm |
| 4-Phenylpiperdine (CPCA Calculated) | |
| AI 1-nitroso-4-phenylpiperdine/day | 400 ng |
| MDD (ketophrofen) | 200 mg |
| AI (ppm) | 2 ppm |

CPCA: Carcinogenic Potency Categorization Approach. See Kruhlak et al. *Regulatory Toxicology and Pharmacology* 150 (2024) 105640.

The average AI for 1-nitroso-4-phenylpiperdine was calculated to be 1.2 ppm based on the results in Table 40C.

Ranitidine hydrochloride was obtained from Sigma Aldrich, US. 4-phenylpiperidine hydrochloride was obtained from Chem-Impex, US. 4-phenylpiperidin-4-ol free base was obtained from TCI, US. 4-phenylpiperdin-4-ol hydrochloride was obtained from Enamine, US.

Films tested were Ascorbic Acid "B" formulation, Visparent, Sodium Bicarbonate "A" formulation, Vitamin E, Sodium Chloride, and Sodium Bicarbonate "B" formulation. See formulations in Table 21 above.

Samples were set up in triplicate for each formulation and for each film, per each timepoint. One test tablet was added to a 20 mL GC vial and added to a 60° C./40% RH environmental chamber for an initial overnight "bake" for about 16 hours. All tablets were autoclaved at 135° C. Film (1 $cm^2$) was dropped in each vial and crimp sealed. Samples were placed in the environmental chamber described above for aging.

A calibration curve was created for each component tested using LC-QTOF method modified from "N-Nitrosamine Formation in Pharmaceutical Solid Drug Products: Experimental Observations" by Moser et al. Journal Pharmaceutical Sciences (2023) 112 (5):1255-1267. The LC-QTOF test samples were prepared as follows:

4 mL of diluent was added via a pipette into each of the GC vials.

Vials were placed in the sonicator for a dedicated 2 hours.

An aliquot of solution (1.5 mL) was transferred to a 2 mL Eppendorf centrifuge tube and centrifuge for 10 min at 13,500 rpm.

0.5 mL of the solution was added to amber HPLC vials for analysis.

NDMA

NDMA did not form after 12 weeks in tablets 1A or 1B.

1-nitroso-4-phenylpiperdine

TABLE 41

| 1-nitroso-4-phenylpiperdine after 12 weeks | | | |
|---|---|---|---|
| Film Tested | Avg PPM | % Decrease | % Std Dev |
| 2A tablet formulation: | | | |
| Control | 3.30 | | 0.94 |
| Ascorbic Acid "B" formulation | 1.10 | 67% | 83.58 |
| Sodium Bicarbonate "B" formulation | 0.89 | 73% | 4.63 |
| Sodium Chloride | 3.21 | 3% | 23.31 |
| Visparent | 3.22 | 2% | 0.20 |
| Vitamin E | 1.69 | 49% | 28.87 |
| Sodium Bicarbonate "A" formulation | 1.42 | 57% | 2.51 |
| 2B tablet formulation: | | | |
| Control | 2.74 | | 27.20 |
| Ascorbic Acid "B" formulation | 2.31 | 16% | 45.61 |
| Sodium Bicarbonate "B" formulation | 1.34 | 51% | 32.42 |
| Sodium Chloride | 2.68 | 2% | 18.88 |
| Visparent | 2.60 | 5% | 8.09 |
| Vitamin E | 2.05 | 25% | 11.88 |
| Sodium Bicarbonate "A" formulation | 1.84 | 33% | 22.98 |

Sodium Bicarbonate "A" formulation and Sodium Bicarbonate "B" formulation reduced the level of 1-nitroso-4-phenylpiperdine by 57% and 73% respectively in 2A formulation tablets, and by 33% and 51% respectively in 2B formulation tablets after 12 weeks.

1-nitroso-4-phenylpiperdin-4-ol

TABLE 42

| 1-nitroso-4-phenylpiperdin-4-ol after 12 weeks | | | |
|---|---|---|---|
| Film Tested | Avg PPM | % Decrease | % Std Dev |
| 3A tablet formulation: | | | |
| Control | 8.72 | | 10.22 |
| Ascorbic Acid "B" formulation | 9.40 | −8% | 1.57 |
| Sodium Bicarbonate "B" formulation | 4.94 | 43% | 54.06 |
| Sodium Chloride | 9.28 | −6% | 3.67 |
| Visparent | 9.42 | −8% | 0.13 |
| Vitamin E | 6.65 | 24% | 44.86 |
| Sodium Bicarbonate "A" formulation | 8.14 | 7% | 2.42 |
| 3B tablet formulation: | | | |
| Control | 31.50 | | 5.32 |
| Ascorbic Acid "B" formulation | 30.51 | 3% | 19.02 |
| Sodium Bicarbonate "B" formulation | 18.03 | 43% | 88.29 |
| Sodium Chloride | 26.12 | 17% | 7.31 |
| Visparent | 25.32 | 20% | 25.16 |
| Vitamin E | 29.24 | 7% | 33.21 |
| Sodium Bicarbonate | 30.59 | 3% | 19.49 |

TABLE 42-continued

| 1-nitroso-4-phenylpiperdin-4-ol after 12 weeks | | | |
|---|---|---|---|
| Film Tested | Avg PPM | % Decrease | % Std Dev |
| "A" formulation | | | |
| 4A tablet formulation: | | | |
| Control | 3.46 | | 31.84 |
| Ascorbic Acid "B" formulation | 3.83 | −11% | 9.31 |
| Sodium Bicarbonate "B" formulation | 1.96 | 43% | 38.36 |
| Sodium Chloride | 4.38 | −27% | 19.84 |
| Visparent | 3.91 | −13% | 4.79 |
| Vitamin E | 3.33 | 4% | 0.41 |
| Sodium Bicarbonate "A" formulation | 3.79 | −10% | 42.95 |
| 4B tablet formulation: | | | |
| Control | 3.94 | | 6.69 |
| Ascorbic Acid "B" formulation | 3.43 | 13% | 21.09 |
| Sodium Bicarbonate "B" formulation | 4.47 | −13% | 28.17 |
| Sodium Chloride | 5.61 | −42% | 18.39 |
| Visparent | 4.45 | −13% | 45.87 |
| Vitamin E | 4.14 | −5% | 20.30 |
| Sodium Bicarbonate "A" formulation | 3.69 | 6% | 14.04 |

Vitamin E and Ascorbic Acid "B" formulation reduced the level of 1-nitroso-4-phenylpiperdin-4-ol by 240% and 4300 respectively in the 3A tablet formulation.

Vitamin E and Ascorbic Acid "B" formulation reduced the level of 1-nitroso-4-phenylpiperdin-4-ol by 70% and 4300 respectively in the 3B tablet formulation. Visparent and sodium chloride reduced it by 2000 and 170% respectively in the 3B tablet formulation.

Vitamin E and Ascorbic Acid "B" formulation reduced the level of 1-nitroso-4-phenylpiperdin-4-ol by 400 and 4300 respectively in the 4A tablet formulation.

Example 17: Film Mitigations-Ranitidine Tablets-NOx, Nitrite and Nitrosamine Measured 900 tablets with ranitidine were made with the formulation shown in Table 43.

TABLE 43

| Ranitidine Tablet Formation | |
|---|---|
| Raw Material | Percentage by Mass (m/m) |
| Ranitidine hydrochloride | 10% |
| Microcrystalline cellulose | 41.75% |
| Lactose monohydrate | 41.75% |
| Sodium starch glycolate | 5% |
| Silicon dioxide | 0.5% |
| Magnesium stearate | 1% |

Films tested (1 $cm^2$ hanging in a GC vial) were Visparent, Tris Activated Carbon, Ascorbic Acid, Sodium Bicarbonate "A" formulation, and Sodium Bicarbonate "B" formulation. See formulations in Table 21 above.

One ranitidine tablet was placed in each GC vial. Samples were aged at 60° C. for the allotted time (1, 8, 12 or 16 weeks).

NDMA was measured using GC-MS directly on the headspace using a calibration curve for NDMA. Nitrite was measured using the cyclohexene derivative method on the headspace. NOx was also measured by the cyclohexene derivative method. For the NOx samples, 0.9 mL of water was added to the test vial. Using a dedicated gas tight 25 μL syringe, a 25 μL aliquot of gas was pulled from the aged vial and delivered into a new vial for testing using the derivative method.

TABLE 44

| Nitrite Week 1 | | | | |
|---|---|---|---|---|
| Active | % Decrease | Count | Std Dev | Std Dev % |
| Visparent | 10.50 | 10 | 20.52 | 195 |
| Tris Activated Carbon | 15.50 | 10 | 29.99 | 193 |
| Ascorbic Acid "B" formulation | 12.01 | 10 | 11.29 | 94 |
| Sodium Bicarbonate "A" formulation | 12.14 | 10 | 26.34 | 217 |
| Sodium Bicarbonate "B" formulation | 19.20 | 10 | 25.19 | 131 |

Results show that Sodium Bicarbonate "B" formulation resulted in the greatest percent decrease in Nitrite after one week.

TABLE 45

| NOx Week 1 | | | | |
|---|---|---|---|---|
| Active | % Decrease | Count | Std Dev | Std Dev % |
| Visparent | 97 | 9 | 6.92 | 7 |
| Tris Activated Carbon | 100 | 10 | 0.00 | 0 |
| Ascorbic Acid "B" formulation | 100 | 9 | 0.00 | 0 |
| Sodium Bicarbonate "A" formulation | 100 | 10 | 0.00 | 0 |
| Sodium Bicarbonate "B" formulation | 100 | 10 | 0.00 | 0 |

Results show that all the films tested were highly effective in decreasing NOx after one week.

TABLE 46

| NDMA Week 1 | | | | |
|---|---|---|---|---|
| Active | % Decrease | Count | Std Dev | Std Dev % |
| Visparent | 63 | 9 | 12.60 | 20 |
| Tris Activated Carbon | 47 | 10 | 34.18 | 73 |
| Ascorbic Acid "B" formulation | 29 | 10 | 31.74 | 109 |
| Sodium Bicarbonate "A" formulation | 58 | 10 | 16.58 | 29 |
| Sodium Bicarbonate "B" formulation | 42 | 10 | 34.92 | 83 |

Results show that all films tested decreased NDMA by at least 2900 after one week.

TABLE 47

| Nitrite Week 8 | | | | |
|---|---|---|---|---|
| Active | % Decrease | Count | Std Dev | Std Dev % |
| Visparent | 10.01 | 9 | 38.76 | 387 |
| Tris Activated Carbon | −11.91 | 8 | 50.26 | −422 |
| Ascorbic Acid "B" formulation | 22.99 | 9 | 37.62 | 164 |
| Sodium Bicarbonate "A" formulation | −33.08 | 9 | 63.27 | −191 |
| Sodium Bicarbonate "B" formulation | −26.03 | 9 | 53.99 | −207 |

Results show that Ascorbic Acid "B" formulation resulted in the greatest percent decrease in Nitrite after 8 weeks.

TABLE 48

| NDMA Week 8 | | | | |
|---|---|---|---|---|
| Active | % Decrease | Count | Std Dev | Std Dev % |
| Visparent | 15.45 | 9 | 16.23 | 105 |
| Tris Activated Carbon | 66.10 | 10 | 9.63 | 15 |
| Ascorbic Acid "B" formulation | 22.40 | 10 | 14.44 | 64 |
| Sodium Bicarbonate "A" formulation | 34.56 | 9 | 14.57 | 42 |
| Sodium Bicarbonate "B" formulation | 46.53 | 10 | 13.50 | 29 |

Results show that all films tested decreased NDMA by at least 1500 after 8 weeks.

TABLE 49

| Nitrite Week 12 | | | | |
|---|---|---|---|---|
| Active | % Decrease | Count | Std Dev | Std Dev % |
| Visparent | −23.76 | 8 | 36.16 | −152 |
| Tris Activated Carbon | −6.19 | 8 | 15.58 | −252 |
| Ascorbic Acid "B" formulation | 34.71 | 9 | 33.38 | 96 |
| Sodium Bicarbonate "A" formulation | −16.51 | 9 | 37.83 | −229 |

Results show that Ascorbic Acid "B" formulation resulted in the greatest percent decrease in Nitrite after 12 weeks.

TABLE 50

| NDMA Week 12 | | | | |
|---|---|---|---|---|
| Active | % Decrease | Count | Std Dev | Std Dev % |
| Visparent | −18.81 | 10 | 57.87 | −308 |
| Tris Activated Carbon | 100 | 9 | 0 | 0 |
| Ascorbic Acid "B" formulation | −13.87 | 9 | 77.13 | −556 |
| Sodium Bicarbonate "A" formulation | 17.79 | 9 | 56.92 | 320 |

Results show that Tris Activated Carbon resulted in the greatest percent decrease in NDMA after 12 weeks.

TABLE 51

| NDMA Week 16 | | | | |
|---|---|---|---|---|
| Active | % Decrease | Count | Std Dev | Std Dev % |
| Visparent | 29.14 | 6 | 20.31 | 70 |
| Tris Activated Carbon | 89.64 | 7 | 13.63 | 15 |
| Ascorbic Acid "B" formulation | −7.55 | 7 | 25.34 | −336 |
| Sodium Bicarbonate "A" formulation | 37.52 | 6 | 27.05 | 72 |

Results show that Tris Activated Carbon resulted in the greatest percent decrease in NDMA after 16 weeks.

Example 18: Film Capacity Testing

1 $cm^2$ film was placed hanging in a GC vial headspace. Sodium Bicarbonate "A" formulation, Sodium Chloride and Vitamin E films were tested. Film formulations are as shown in Table 21. The control did not have any film in the GC vial. 1 mL of 1M sulfuric acid solution and 1 mL of potassium nitrite solution (Dg/v mL) was placed into the GC vial. Samples were prepared in sets of five (5). The film was placed suspended inside the GC vial, and sealed, and aged for 7 days at 60° C. GC-MS was conducted on the headspace using the derivative method.

For capacity testing, the film samples from the previous aging were reused to determine the total capacity of NOx absorption/reaction.

Samples were re-prepared in sets of five (5) on the same day as sampling.

The testing lasted 24 weeks. Results are shown in Table 52 below.

Total NOx was estimated to be 328 ppm, i.e. 0.328 mg.

TABLE 52

| Film Capacity Testing-All weeks (24) averaged | | | | | | | |
|---|---|---|---|---|---|---|---|
| Film | Conc. (ppm) | Std Dev | Std Dev % | Count | Ppm/ day | Std Dev | Std Dev % |
| Control | 13.50 | 6.33 | 47 | 93 | — | — | — |
| Sodium Bicarbonate "A" formulation | 1.13 | 1.49 | 132 | 97 | 1.77 | 0.21 | 12.0 |
| Sodium Chloride | 0.63 | 1.05 | 166 | 96 | 1.84 | 0.15 | 8.2 |
| Vitamin E | 0.82 | 1.26 | 154 | 86 | 1.81 | 0.18 | 9.9 |

All three films tested were highly effective in absorbing NOx. Film with Sodium Chloride was the most effective in absorbing NOx, followed by Vitamin E and Sodium Bicarbonate "A" formulation.

Example 19: Excipient Testing

Tablets with various excipients and without a drug were made with the formulations shown in Tables 53A-53D.

TABLE 53A

| Control Tablet Formulation | |
|---|---|
| Raw Material | Percentage by Mass (m/m) |
| Microcrystalline cellulose | 66% |
| Lactose monohydrate | 33% |

TABLE 53A-continued

| Control Tablet Formulation | |
|---|---|
| Raw Material | Percentage by Mass (m/m) |
| Magnesium stearate | 1% |
| Total | 100% |

TABLE 53B

| Spiked Control Tablet Formulation | |
|---|---|
| Raw Material | Percentage by Mass (m/m) |
| Microcrystalline cellulose | 65.97% |
| Lactose monohydrate | 33% |
| Magnesium stearate | 1% |
| Sodium nitrite | 0.03% |
| Total | 100% |

TABLE 53C

| Croscarmellose Tablet Formulation | |
|---|---|
| Raw Material | Percentage by Mass (m/m) |
| Microcrystalline cellulose | 61% |
| Lactose monohydrate | 33% |
| Croscarmellose sodium | 5% |
| Magnesium stearate | 1% |
| Total | 100% |

TABLE 53D

| Croscarmellose Spiked Tablet Formulation | |
|---|---|
| Raw Material | Percentage by Mass (m/m) |
| Microcrystalline cellulose | 60.95% |
| Lactose monohydrate | 33% |
| Croscarmellose sodium | 5% |
| Magnesium stearate | 1% |
| Sodium nitrite | 0.03% |
| Total | 100% |

Films tested (1 $cm^2$ hanging in a GC vial) were Visparent, Tris Activated Carbon, Ascorbic Acid, and Vitamin E. See film formulations in Table 21 above.

One tablet was placed in each GC vial. Samples were aged at 60° C. for 1 week and were assayed on a headspace using GC-MSD. Nitrite was assayed using the derivative method.

Nitrite in the headspace was not above the level of the no-film control for any of the films tested for the Control tablet formulation of Table 53A.

TABLE 54A

| Nitrite Week 1, Spiked Control Tablets | | | | |
|---|---|---|---|---|
| Active | % Decrease | Count | Std Dev | Std Dev % |
| Visparent | 100 | 10 | 0 | 0 |
| Tris Activated Carbon | 36 | 10 | 47 | 130 |
| Ascorbic Acid "B" formulation | 100 | 8 | 0 | 0 |
| Vitamin E | 41 | 9 | 27 | 66 |

Results show that Visparent and Ascorbic Acid "B" formulation films resulted in the greatest percent decrease in nitrite. All films resulted in at least 36% decrease in nitrite.

Nitrite in the headspace was not above the level of the no-film control for any of the films tested for the Croscarmellose tablet formulation of Table 53C.

TABLE 54B

| Nitrite Week 1, Spiked Croscarmellose Tablets | | | | |
|---|---|---|---|---|
| Active | % Decrease | Count | Std Dev | Std Dev % |
| Visparent | 68 | 10 | 52 | 76 |
| Tris Activated Carbon | 50 | 10 | 37.54 | 75 |
| Ascorbic Acid "B" formulation | 89 | 10 | 13.33 | 15 |
| Vitamin E | 35 | 10 | 50.53 | 143 |

Results show that Visparent and Ascorbic Acid "B" formulation films resulted in the greatest percent decrease in nitrite. All films resulted in at least 35% decrease in nitrite.

Example 20: Ritonavir Tablets Blister Packs

Tablets with ritonavir were made and were placed in blister packs without film (control) or in blister packs containing film with a formulation as shown in Table 54 below or with a Vitamin E formulation as described in Table 21 above. N-nitroso ritonavir (NNO) was detected by HPLC.

TABLE 55

| Film Formulations | | | |
|---|---|---|---|
| Active | Material | Percentage in Film Formulation (wt %) | Thickness |
| Silica Gel | Silica Gel | 60 | 0.3-0.8 mm |
| | EVA-2528 | 3 | |
| | RESIN-3040 | 37 | |
| K360 (3A molecular sieve) | K360 SYLOSIV | 60 | 0.3-0.8 mm |
| | EVA-2528 | 3 | |
| | RESIN-3040 | 37 | |

TABLE 56

| NNO concentration (ng/day) for Tablets at 30° C. 65% RH | | | | |
|---|---|---|---|---|
| Time (days) | Control no film NNO ng/day | Silica Gel film NNO ng/day | K360 film NNO ng/day | Vit E film NNO ng/day |
| 0 | 22 | 18 | 16 | 20 |
| 7 | 22 | 21 | 23 | 22 |
| 14 | 18 | 17 | 17 | 19 |
| 28 | 19 | 18 | 18 | 22 |
| 42 | 19 | 17 | 18 | 21 |
| 67 | 23 | 20 | 19 | 23 |

All values in the table are approximate. Time 0 corresponds to when the tablets were placed in the blisters. The NNO concentration for tablets in blisters with silica gel film was always lower than that of the control. Silica gel and K360 films were the most effective at reducing NNO concentration.

Results for NNO concentration for tablets at 50° C. ambient humidity are shown in Table 57 below. On day 28, some of the blisters were opened and those tablets were left in the same stability conditions as the tablets that remained inside closed blisters. The tablets from the open blisters were assayed at 64 days and 77 days and corresponding entries in Table 57 below are labeled "open blister". All other entries correspond to tablets that remained inside closed blisters.

TABLE 57

| NNO concentration (ng/day) for Tablets at 50° C. Ambient Humidity | | | | |
|---|---|---|---|---|
| Time (days) | Control no film NNO ng/day | Silica Gel film NNO ng/day | K360 film NNO ng/day | Vit E film NNO ng/day |
| 0 | 22 | 18 | 16 | 20 |
| 7 | 24 | 22 | 22 | 25 |
| 14 | 22 | 20 | 18 | 23 |
| 22 | 26 | 18 | 21 | 24 |
| 28 | 26 | 22 | 24 | 25 |
| 64 (open blister) | 42 | 22 (open blister) | 28 (open blister) | 39 (open blister) |
| 67 | 44 | 23 | 27 | 42 |
| 77 | 41 | 20 | 27 | 38 |
| 77 (open blister) | 42 | 21 (open blister) | 26 (open blister) | 38 (open blister) |

All values in the table are approximate. Time 0 corresponds to when the tablets were placed in the blisters. The NNO concentration for tablets in blisters with silica gel film or for K360 film was always lower than that of the control. Silica gel and K360 films were the most effective at reducing NNO concentration.

Tablets that were removed from the open blisters did not show a significant increase in NNO concentration compared to tablets that remained in the closed blisters. NNO formation in blisters with silica gel film seems to have been mitigated the most overall, emphasizing the effectiveness of the silica gel film.

Example 21: Ranitidine and 1-nitroso-4-phenylpiperdin-4-ol Tablets

Tablets with ranitidine and tablets with 4-phenylpiperdin-4-ol were made with the formulations shown the tables below.

TABLE 58

| Ranitidine Tablet Formulation | |
|---|---|
| Raw Material | Percentage by Mass (m/m) |
| Ranitidine hydrochloride | 10% |
| Microcrystalline cellulose | 41.73% |
| Lactose monohydrate | 41.72% |
| Sodium starch glycolate | 5% |
| Silicon dioxide | 0.5% |
| Magnesium stearate | 1% |
| Sodium nitrite | 0.05% |
| Total | 100% |

TABLE 59

| 4-phenylpiperdin-4-ol Tablet Formulation | |
|---|---|
| Raw Material | Percentage by Mass (m/m) |
| 4-phenylpiperdin-4-ol hydrochloride | 12.06% |
| Microcrystalline cellulose | 25.48% |
| Lactose monohydrate | 25.48% |
| Calcium phosphate, dibasic | 25.49% |
| Sodium starch glycolate | 4.4% |
| Polyvinylpyrrolidone | 4.4% |

TABLE 59-continued

| 4-phenylpiperdin-4-ol Tablet Formulation | |
|---|---|
| Raw Material | Percentage by Mass (m/m) |
| Silicon dioxide | 0.88% |
| Magnesium stearate | 0.88% |
| Sodium stearyl fumarate | 0.88% |
| Sodium nitrite | 0.05% |
| Total | 100% |

Ranitidine tablets were pressed and placed in blister cards. 4-phenylpiperdin-4-ol tablets were autoclaved at 135° C. and placed in blister cards with film that had been heat staked to lidding foil.

Films tested were Sodium chloride, Ascorbic Acid, and Sodium Bicarbonate "A" formulation. See formulations in Table 21 above.

Samples were aged at the temperature and relative humidity indicated, for the allotted time. NDMA and 1-nitroso-4-phenylpiperdin-4-ol were detected by LC-QTOF.

TABLE 60

| NDMA | | |
|---|---|---|
| Temperature/RH | Film | Total Nitrosamine (ppm-weeks) |
| 50/35 | Control | 414.97 |
| | Sodium Chloride | 444.84 |
| | Sodium Bicarbonate | 404.01 |
| | Ascorbic Acid | 330.85 |
| 50/50 | Control | 393.33 |
| | Sodium Chloride | 411.98 |
| | Sodium Bicarbonate | 356.20 |
| | Ascorbic Acid | 325.18 |
| 50/75 | Control | 318.79 |
| | Sodium Chloride | 333.43 |
| | Sodium Bicarbonate | 312.02 |
| | Ascorbic Acid | 268.71 |
| 70/35 | Control | 192.31 |
| | Sodium Chloride | 179.77 |
| | Sodium Bicarbonate | N/A |
| | Ascorbic Acid | 165.50 |
| 70/50 | Control | 118.49 |
| | Sodium Chloride | 138.77 |
| | Sodium Bicarbonate | N/A |
| | Ascorbic Acid | 105.81 |
| 70/75 | Control | 80.28 |
| | Sodium Chloride | 7.89 |
| | Sodium Bicarbonate | 53.15 |
| | Ascorbic Acid | 32.06 |

N/A: not available

TABLE 61

| 1-nitroso-4-phenylpiperdin-ol | | |
|---|---|---|
| Temperature/RH | Film | Total Nitrosamine (ppm-weeks) |
| 50/35 | Control | 117.72 |
| | Sodium Chloride | 118.48 |
| | Sodium Bicarbonate | 87.61 |
| | Ascorbic Acid | 98.41 |
| 50/50 | Control | 127.83 |
| | Sodium Chloride | 131.00 |
| | Sodium Bicarbonate | 99.82 |
| | Ascorbic Acid | 110.36 |
| 50/75 | Control | 93.44 |
| | Sodium Chloride | 89.62 |
| | Sodium Bicarbonate | 75.37 |
| | Ascorbic Acid | 85.63 |

TABLE 61-continued

| 1-nitroso-4-phenylpiperdin-ol | | |
|---|---|---|
| Temperature/RH | Film | Total Nitrosamine (ppm-weeks) |
| 60/35 | Control | 104.93 |
| | Sodium Chloride | 105.22 |
| | Sodium Bicarbonate | 89.74 |
| | Ascorbic Acid | 123.54 |
| 60/50 | Control | 89.39 |
| | Sodium Chloride | 97.24 |
| | Sodium Bicarbonate | 81.39 |
| | Ascorbic Acid | 86.87 |
| 60/75 | Control | 85.19 |
| | Sodium Chloride | 100.13 |
| | Sodium Bicarbonate | 81.10 |
| | Ascorbic Acid | 97.51 |
| 70/35 | Control | 115.63 |
| | Sodium Chloride | 96.60 |
| | Sodium Bicarbonate | 99.10 |
| | Ascorbic Acid | 89.00 |
| 70/50 | Control | 100.61 |
| | Sodium Chloride | 103.00 |
| | Sodium Bicarbonate | 106.09 |
| | Ascorbic Acid | 97.91 |
| 70/75 | Control | 89.29 |
| | Sodium Chloride | 101.21 |
| | Sodium Bicarbonate | 94.63 |
| | Ascorbic Acid | 91.92 |

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for treating a patient having a medical condition with a pharmaceutical dosage form, the pharmaceutical dosage form comprising or forming an N-nitroso compound contaminant, the method being configured to mitigate a potential adverse effect on a patient associated with the N-nitroso compound contaminant, the method comprising:

a) providing a package comprising:
   i. an enclosure;
   ii. the pharmaceutical dosage form housed within the enclosure, wherein a headspace is formed within a volume of the enclosure that is not occupied by the pharmaceutical dosage form; and
   iii. an entrained polymer comprising a blended form of a base polymer and an active agent, the active agent consisting essentially of sodium bicarbonate in a granular, particulate or powdered form, the entrained polymer being provided in an amount within the headspace that is effective in decreasing a rate of formation of, or decreasing an amount of, the N-nitroso compound contaminant;
b) opening the enclosure to dispense the pharmaceutical dosage form; and
c) administering the pharmaceutical dosage form to provide a therapeutically effective amount of drug to the patient for treating the medical condition with improved patient safety by reducing the potential adverse effect associated with the pharmaceutical dosage form on account of the entrained polymer decreasing the rate of formation of, or the amount of, the N-nitroso compound contaminant.

2. The method of claim 1, wherein the entrained polymer is effective in decreasing a rate of formation of, or an amount of, a nitrosating agent in the enclosure, thereby decreasing the rate of formation of, or decreasing the amount of, the N-nitroso compound contaminant.

3. The method of claim 2, wherein the nitrosating agent is nitrite or $NO_x$.

4. The method of claim 3, wherein the N-nitroso compound contaminant is selected from the group consisting of NDMA, NMBA, NDEA, NMPA, NIPEA and NDIPA.

5. The method of claim 4, wherein the entrained polymer is effective such that the amount of N-nitroso compound contaminant ingested by the patient does not exceed 96 ng/day for NDMA or NMBA, or 26.5 ng/day for NDEA, NMPA, NIPEA or NDIPA.

6. The method of claim 1, wherein the base polymer is selected from one or more of the group consisting of: polypropylene, polyethylene, polyisoprene, polybutadiene, polybutene, polysiloxane, polycarbonate, polyamide, ethylene-vinyl acetate copolymer, ethylene-methacrylate copolymer, poly(vinylchloride), polystyrene, polyester, polyanhydride, polyacrylonitrile, polysulfone, polyacrylic ester, acrylic, polyurethane and polyacetal and copolymers thereof.

7. The method of claim 6, wherein:

the entrained polymer comprises a polymeric channeling agent that is present in a range of from 1% to 25% by weight with respect to total weight of the entrained polymer, and the polymeric channeling agent forms interconnecting channels through the entrained polymer.

8. The method of claim 1, wherein the active agent is present in a range of 30% to 70% by weight with respect to the total weight of the entrained polymer.

9. The method of claim 1, wherein the package is a blister package.

10. The method of claim 9, wherein:

the entrained polymer is an extruded or cast film, the blister package comprises a backing and a cover attached to the backing, the cover and backing in combination form the enclosure in the form of a blister cavity, and the film is chemically bonded to an inner wall of the enclosure by a heat seal, without a separate adhesive between the film and the inner wall.

11. The method of claim 1, wherein the pharmaceutical dosage form comprises an active pharmaceutical ingredient or a pharmaceutically acceptable salt and/or enantiomer thereof selected from the group consisting of: Almotriptan, Metformin, Ranitidine, Amitriptyline, Nortriptyline, Betahistine, Chloropyramine, Citalopram, Sumatriptan, Lamisil, Terbisil, Zostavax, Bedaquiline, Brompheniramine, Cabergoline, Carbinoxamine, Chlophedianol, Chlorpheniramine, Chlorpromazine, Clarithromycin, Clomipramine, Clozapine, Cyclobenzaprine, Demeclocycline, Dexbrompheniramine, Dexchlorpheniramine, Diltiazem, Diphenhydramine, Doxepin, Doxycycline, Doxylamine, Eravacycline, Erythromycin, Escitalopram, Imipramine, Maralixibat, Masitinib, Methadone, Methylene Blue, Mifepristone, Minocycline, Olopatadine, Omadacycline, Padimate O, Pheniramine, Phenyltoloxamine, Promethazine, Propoxyphene, Pyrilamine, Quinupristin, Rivastigmine, Rizatriptan, Sarecycline, Sildenafil, Spinosad, Tamoxifen, Tapentadol, Telithromycin, Tetracycline, Thonzylamine, Tigecycline, Tramadol, Trimethobenzamide, Trimipramine, Ulipristal Acetate, Venlafaxine, Zolmitriptan, Tripelennamine, Desvenlafaxine, Orphenadrine, Terbinafine, Ethylisopropylamine, Sitagliptin, Losartan, Valsartan, Atomoxetine, Lidocaine, Azelastine, Duloxetine, Fluoxetine, Chloropyramine, Phenylephrine, Rasagiline, Reboxetine, Aripiprazole, Mitapivat, Rifampicin, Alogliptin, Ranolazine, Rotigotine, Azacyclonol, Quetiapine, Cinacalcet, Desloratadine, Nintedanib, Sildenafil, Landiolol, Mirabegron, Mirtazapine, Valaciclovir, Pramipexole, Ranolazine, Ribociclib, Tetracaine, Trimetazidine, Varenicline, Vortioxetine, Methylphenidate, Paroxetine, Piperidine, Moxifloxacin, Daridorexant, Rotigotine, Ropivacaine, Ambroxol, Atenolol, Benazepril, Betaxolol, Bisoprolol, Bumetanide, Bupropion, Celiprolol, Cilazapril, Ciprofloxacin, Dabigatran Etexilate, Trimebutine, Diclofenac, Dorzolamide, Enalapril, Esmolol, Isosorbide mononitrate, Imatinib, Isosorbide mononitrate, Indapamide, Ketamine, Labetalol, Leniolisib, Levofloxacin, Lisinopril, Metoprolol, Moxifloxacin, Nebivolol, Perindopril, Arpraziquantel, Propranolol, Pseudoephedrine, Quetiapine, Ramipril, Rivaroxaban, Salbutamol, Sertraline, Sotalol, Tamsulosin, Ticagrelor, Urapidil, Vildagliptin, Gliclazide, Mefenamic acid, Azithromycin, Calcium folinate, Calcium levofolinate, Hydrochlorothiazide, Quinapril and Ritonavir.

12. A method of decreasing a rate of formation of, or decreasing an amount of, an N-nitroso compound contaminant in an enclosure of a pharmaceutical drug package to inhibit a potential adverse health effect on a patient associated with the N-nitroso compound contaminant, the method comprising:

(a) providing at least one pharmaceutical dosage form unit in the enclosure of the pharmaceutical drug package, thereby forming a headspace in the enclosure in a portion of the enclosure not occupied by the at least one pharmaceutical dosage form unit, the at least one pharmaceutical dosage form unit comprising or forming the N-nitroso compound contaminant; and (b) providing an entrained polymer within the headspace, the entrained polymer comprising a blended form of a base polymer and an active agent, the active agent consisting essentially of sodium bicarbonate in a granular, particulate, or powdered form;

wherein the entrained polymer is provided in an amount that is effective in decreasing the rate of formation of, or decreasing the amount of, the N-nitroso compound contaminant, thereby inhibiting the potential adverse health effect on the patient associated with the N-nitroso compound contaminant.

13. The method of claim 12, wherein the entrained polymer is effective in decreasing a rate of formation of, or an amount of, a nitrosating agent in the enclosure, thereby decreasing the rate of formation of, or decreasing the amount of, the N-nitroso compound contaminant.

14. The method of claim 13, wherein the nitrosating agent is nitrite or $NO_x$.

15. The method of claim 12, wherein the N-nitroso compound contaminant is selected from the group consisting of NDMA, NMBA, NDEA, NMPA, NIPEA, and NDIPA.

16. The method of claim 15, wherein the entrained polymer is effective such that the amount of N-nitroso compound contaminant ingested by the patient does not exceed 96 ng/day for NDMA or NMBA, or 26.5 ng/day for NDEA, NMPA, NIPEA or NDIPA.

17. The method of claim 12, wherein the base polymer is selected from one or more of the group consisting of: polypropylene, polyethylene, polyisoprene, polybutadiene, polybutene, polysiloxane, polycarbonate, polyamide, ethylene-vinyl acetate copolymer, ethylene-methacrylate copolymer, poly(vinylchloride), polystyrene, polyester, polyanhydride, polyacrylonitrile, polysulfone, polyacrylic ester, acrylic, polyurethane and polyacetal and copolymers thereof.

18. The method of claim 17, wherein:

the entrained polymer comprises a polymeric channeling agent that is present in a range of from 1% to 25% by weight with respect to total weight of the entrained polymer, and the polymeric channeling agent forms interconnecting channels through the entrained polymer.

19. The method of claim 12, wherein the active agent is present in a range of 30% to 70% by weight with respect to the total weight of the entrained polymer.

20. The method of claim 12, wherein the package is a blister package.

21. The method of claim 20, wherein:

the entrained polymer is an extruded or cast film, the blister package comprises a backing and a cover attached to the backing, the cover and backing in combination form the enclosure in the form of a blister cavity, and the film is chemically bonded to an inner wall of the enclosure by a heat seal, without a separate adhesive between the film and the inner wall.

22. The method of claim 12, wherein the at least one pharmaceutical dosage form unit comprises an active pharmaceutical ingredient or a pharmaceutically acceptable salt and/or enantiomer thereof selected from the group consisting of: Almotriptan, Metformin, Ranitidine, Amitriptyline, Nortriptyline, Betahistine, Chloropyramine, Citalopram, Sumatriptan, Lamisil, Terbisil, Zostavax, Bedaquiline, Brompheniramine, Cabergoline, Carbinoxamine, Chlophedianol, Chlorpheniramine, Chlorpromazine, Clarithromycin, Clomipramine, Clozapine, Cyclobenzaprine, Demeclocycline, Dexbrompheniramine, Dexchlorpheniramine, Diltiazem, Diphenhydramine, Doxepin, Doxycycline, Doxylamine, Eravacycline, Erythromycin, Escitalopram, Imipramine, Maralixibat, Masitinib, Methadone, Methylene Blue, Mifepristone, Minocycline, Olopatadine, Omadacycline, Padimate O, Pheniramine, Phenyltoloxamine, Promethazine, Propoxyphene, Pyrilamine, Quinupristin, Rivastigmine, Rizatriptan, Sarecycline, Sildenafil, Spinosad, Tamoxifen, Tapentadol, Telithromycin, Tetracycline, Thonzylamine, Tigecycline, Tramadol, Trimethobenzamide, Trimipramine, Ulipristal Acetate, Venlafaxine, Zolmitriptan, Tripelennamine, Desvenlafaxine, Orphenadrine, Terbinafine, Ethylisopropylamine, Sitagliptin, Losartan, Valsartan, Atomoxetine, Lidocaine, Azelastine, Duloxetine, Fluoxetine, Chloropyramine, Phenylephrine, Rasagiline, Reboxetine, Aripiprazole, Mitapivat, Rifampicin, Alogliptin, Ranolazine, Rotigotine, Azacyclonol, Quetiapine, Cinacalcet, Desloratadine, Nintedanib, Sildenafil, Landiolol, Mirabegron, Mirtazapine, Valaciclovir, Pramipexole, Ranolazine, Ribociclib, Tetracaine, Trimetazidine, Varenicline, Vortioxetine, Methylphenidate, Paroxetine, Piperidine, Moxifloxacin, Daridorexant, Rotigotine, Ropivacaine, Ambroxol, Atenolol, Benazepril, Betaxolol, Bisoprolol, Bumetanide, Bupropion, Celiprolol, Cilazapril, Ciprofloxacin, Dabigatran Etexilate, Trimebutine, Diclofenac, Dorzolamide, Enalapril, Esmolol, Isosorbide mononitrate, Imatinib, Isosorbide mononitrate, Indapamide, Ketamine, Labetalol, Leniolisib, Levofloxacin, Lisinopril, Metoprolol, Moxifloxacin, Nebivolol, Perindopril, Arpraziquantel, Propranolol, Pseudoephedrine, Quetiapine, Ramipril, Rivaroxaban, Salbutamol, Sertraline, Sotalol, Tamsulosin, Ticagrelor, Urapidil, Vildagliptin, Gliclazide, Mefenamic acid, Azithromycin, Calcium folinate, Calcium levofolinate, Hydrochlorothiazide, Quinapril and Ritonavir.

23. A drug delivery system for mitigating a potential adverse effect on a patient that is associated with an N-nitroso compound contaminant, the system comprising:

a package comprising:

i. an enclosure;

ii. at least one pharmaceutical dosage form unit housed within the enclosure, wherein a headspace is formed within a volume of the enclosure that is not occupied by the at least one pharmaceutical dosage form unit; and iii. an entrained polymer comprising a blended form of a base polymer and an active agent, the active agent consisting essentially of sodium bicarbonate in a granular, particulate, or powdered form, the entrained polymer being provided in an amount within the headspace that is effective in decreasing a rate of formation of, or an amount of, the N-nitroso compound contaminant in the headspace and/or in the at least one pharmaceutical dosage form unit, thereby mitigating the potential adverse effect on the patient associated with the N-nitroso compound contaminant.

24. The system of claim 23, wherein the entrained polymer is effective in decreasing a rate of formation of, or an amount of, a nitrosating agent in the enclosure, thereby decreasing the rate of formation of, or decreasing the amount of, the N-nitroso compound contaminant.

25. The system of claim 24, wherein the nitrosating agent is chosen from nitrite and $NO_x$.

26. The system of claim 23, wherein the base polymer is selected from one or more of the group consisting of: polypropylene, polyethylene, polyisoprene, polybutadiene, polybutene, polysiloxane, polycarbonate, polyamide, ethylene-vinyl acetate copolymer, ethylene-methacrylate copolymer, poly(vinylchloride), polystyrene, polyester, polyanhydride, polyacrylonitrile, polysulfone, polyacrylic ester, acrylic, polyurethane and polyacetal and copolymers thereof.

27. The system of claim 23, wherein:

the entrained polymer comprises a polymeric channeling agent that is present in a range of from 1% to 25% by weight with respect to total weight of the entrained polymer, and the polymeric channeling agent forms interconnecting channels through the entrained polymer.

28. The system of claim 23, wherein the active agent is present in a range of 30% to 70% by weight with respect to the total weight of the entrained polymer.

29. The system of claim 23, wherein:

the package is a blister package, the entrained polymer is an extruded or cast film, the blister package comprises a backing and a cover attached to the backing, the cover and backing in combination form the enclosure in the form of a blister cavity, and the film is chemically bonded to an inner wall of the enclosure by a heat seal, without a separate adhesive between the film and the inner wall.

30. The system of claim 23, wherein the at least one pharmaceutical dosage form unit comprises an active pharmaceutical ingredient or a pharmaceutically acceptable salt and/or enantiomer thereof selected from the group consisting of: Almotriptan, Metformin, Ranitidine, Amitriptyline, Nortriptyline, Betahistine, Chloropyramine, Citalopram, Sumatriptan, Lamisil, Terbisil, Zostavax, Bedaquiline, Brompheniramine, Cabergoline, Carbinoxamine, Chlophedianol, Chlorpheniramine, Chlorpromazine, Clarithromycin, Clomipramine, Clozapine, Cyclobenzaprine, Demeclocycline, Dexbrompheniramine, Dexchlorpheniramine, Diltiazem, Diphenhydramine, Doxepin, Doxycycline, Doxylamine, Eravacycline, Erythromycin, Escitalopram, Imipramine, Maralixibat, Masitinib, Methadone, Methylene Blue, Mifepristone, Minocycline, Olopatadine, Omadacycline, Padimate O, Pheniramine, Phenyltoloxamine, Promethazine, Propoxyphene, Pyrilamine, Quinupristin, Rivastigmine, Rizatriptan, Sarecycline, Sildenafil, Spinosad, Tamoxifen, Tapentadol, Telithromycin, Tetracycline, Thonzylamine, Tigecycline, Tramadol, Trimethobenzamide, Trimipramine, Ulipristal Acetate, Venlafaxine, Zolmitriptan, Tripelennamine, Desvenlafaxine, Orphenadrine, Terbinafine, Ethylisopropylamine, Sitagliptin, Losartan, Valsartan, Atomoxetine, Lidocaine, Azelastine, Duloxetine, Fluoxetine, Chloropyramine, Phenylephrine, Rasagiline, Reboxetine, Aripiprazole, Mitapivat, Rifampicin, Alogliptin, Ranolazine, Rotigotine, Azacyclonol, Quetiapine, Cinacalcet, Desloratadine, Nintedanib, Sildenafil, Landiolol, Mirabegron, Mirtazapine, Valaciclovir, Pramipexole, Ranolazine, Ribociclib, Tetracaine, Trimetazidine, Varenicline, Vortioxetine, Methylphenidate, Paroxetine, Piperidine, Moxifloxacin, Daridorexant, Rotigotine, Ropivacaine, Ambroxol, Atenolol, Benazepril, Betaxolol, Bisoprolol, Bumetanide, Bupropion, Celiprolol, Cilazapril, Ciprofloxacin, Dabigatran Etexilate, Trimebutine, Diclofenac, Dorzolamide, Enalapril, Esmolol, Isosorbide mononitrate, Imatinib, Isosorbide mononitrate, Indapamide, Ketamine, Labetalol, Leniolisib, Levofloxacin, Lisinopril, Metoprolol, Moxifloxacin, Nebivolol, Perindopril, Arpraziquantel, Propranolol, Pseudoephedrine, Quetiapine, Ramipril, Rivaroxaban, Salbutamol, Sertraline, Sotalol, Tamsulosin, Ticagrelor, Urapidil, Vildagliptin, Gliclazide, Mefenamic acid, Azithromycin, Calcium folinate, Calcium levofolinate, Hydrochlorothiazide, Quinapril and Ritonavir.

* * * * *